(12) United States Patent
Nakatani et al.

(10) Patent No.: US 8,993,124 B2
(45) Date of Patent: Mar. 31, 2015

(54) POLYMER COMPOUND COMPRISING ARYL REPEATING UNITS WITH CROSSLINKING PENDENT GROUPS AND LIGHT-EMITTING ELEMENT USING SAME

(75) Inventors: Tomoya Nakatani, Tsukuba (JP); Keiko Kawaguchi, Karatsu (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 566 days.

(21) Appl. No.: 13/056,227

(22) PCT Filed: Jul. 29, 2009

(86) PCT No.: PCT/JP2009/063456
§ 371 (c)(1),
(2), (4) Date: Jan. 27, 2011

(87) PCT Pub. No.: WO2010/013723
PCT Pub. Date: Feb. 4, 2010

(65) Prior Publication Data
US 2011/0127516 A1     Jun. 2, 2011

(30) Foreign Application Priority Data

Jul. 29, 2008  (JP) .................................. 2008-194522
Feb. 20, 2009  (JP) .................................. 2009-037660

(51) Int. Cl.
| | |
|---|---|
| H01L 51/54 | (2006.01) |
| C08G 73/02 | (2006.01) |
| C08L 39/00 | (2006.01) |
| C07C 25/22 | (2006.01) |
| C07C 17/275 | (2006.01) |
| C07C 17/23 | (2006.01) |

(Continued)

(52) U.S. Cl.
CPC ............ H01L 51/0036 (2013.01); C07C 25/22 (2013.01); C07C 25/24 (2013.01); C07C 309/65 (2013.01); C08G 61/02 (2013.01); C08G 61/12 (2013.01); C08G 61/124 (2013.01); C08L 65/00 (2013.01); H01L 51/0035 (2013.01); H01L 51/0039 (2013.01); C09K 11/06 (2013.01); C07C 2102/06 (2013.01); C07C 2103/18 (2013.01); C08G 2261/135 (2013.01); C08G 2261/148 (2013.01); C08G 2261/3142 (2013.01); C08G 2261/316 (2013.01); C08G 2261/3241 (2013.01); C08G 2261/411 (2013.01); C08G 2261/76 (2013.01); C08G 2261/92 (2013.01); H01L 51/5048 (2013.01); C08G 2261/124 (2013.01); Y02E 10/549 (2013.01); C09K 2211/1416 (2013.01); C09K 2211/1425 (2013.01); C09K 2211/145 (2013.01); C09K 2211/1458 (2013.01); C09K 2211/1466 (2013.01); Y10S 428/917 (2013.01)

USPC ...... 428/690; 428/917; 257/40; 257/E51.027; 313/504; 528/8; 524/610

(58) Field of Classification Search
None
See application file for complete search history.

(56) References Cited

U.S. PATENT DOCUMENTS

| | | |
|---|---|---|
| 5,708,130 A | 1/1998 | Woo et al. |
| 5,962,631 A | 10/1999 | Woo et al. |

(Continued)

FOREIGN PATENT DOCUMENTS

| | | |
|---|---|---|
| EP | 2067805 A1 | 6/2009 |
| JP | 11-510535 A | 9/1999 |

(Continued)

OTHER PUBLICATIONS

Extended European Search Report issued Mar. 7, 2013 in European Patent Application No. 09802965.6 to Sumitomo Chemical Co., Ltd.

(Continued)

Primary Examiner — Andrew K Bohaty
(74) Attorney, Agent, or Firm — Sughrue Mion, PLLC

(57) ABSTRACT

A polymer compound including: the repeating unit shown in the following formula (I) (wherein: $Ar^1$ represents an arylene group, a divalent heterocyclic group, or a divalent aromatic amine; $J^1$ and $J^2$ each represent a direct bond, an alkylene group, or a phenylene group, and $X^1$ represents an oxygen atom or a sulfur atom; i is an integer from 0 to 3; j is 0 or 1; m is 1 or 2; and $R^1$ represents a hydrogen atom, an alkyl group, an alkoxy group, or the like) and the repeating unit shown in the following formula (II) (wherein: Ar2 represents a fluorene-diyl group; $J^3$ and $J^4$ each represent a direct bond, an alkylene group, or a phenylene group; $X^2$ represents an oxygen atom or a sulfur atom; k is an integer from 0 to 3; l is 0 or 1; and n is 1 or 2).

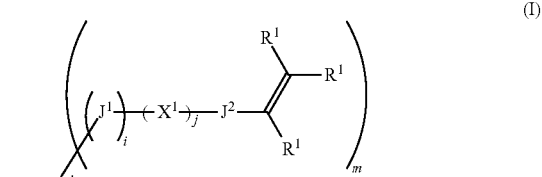

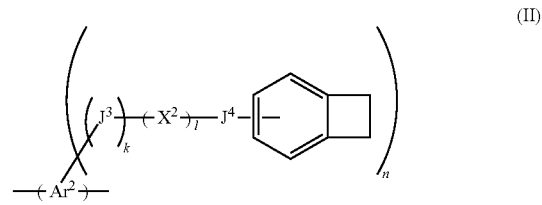

20 Claims, No Drawings

(51) Int. Cl.
*H01L 51/00* (2006.01)
*C07C 25/24* (2006.01)
*C07C 309/65* (2006.01)
*C08G 61/02* (2006.01)
*C08G 61/12* (2006.01)
*C08L 65/00* (2006.01)
*C09K 11/06* (2006.01)
*H01L 51/50* (2006.01)

(56) References Cited

U.S. PATENT DOCUMENTS

| | | | |
|---|---|---|---|
| 7,956,350 B2 * | 6/2011 | Inbasekaran et al. | 257/40 |
| 2004/0106758 A1 | 6/2004 | Nishiguchi et al. | |
| 2005/0146263 A1 * | 7/2005 | Kelly et al. | 313/504 |
| 2005/0176909 A1 | 8/2005 | Nishiguchi et al. | |
| 2005/0186106 A1 | 8/2005 | Li et al. | |
| 2007/0063191 A1 | 3/2007 | Inbasekaran et al. | |
| 2007/0102695 A1 | 5/2007 | Inbasekaran et al. | |
| 2008/0113176 A1 | 5/2008 | Nishiguchi et al. | |
| 2009/0315453 A1 | 12/2009 | Kobayashi et al. | |

FOREIGN PATENT DOCUMENTS

| | | |
|---|---|---|
| JP | 2004-300314 A | 10/2004 |
| JP | 2004300314 A | 10/2004 |
| JP | 2007-528916 A | 10/2007 |
| JP | 2008-106241 A | 5/2008 |
| JP | 2009-196982 A | 9/2009 |
| JP | 2009196982 A | 9/2009 |
| WO | 02/083610 A1 | 10/2002 |
| WO | 2005/035221 A1 | 4/2005 |
| WO | 2005/049689 A2 | 6/2005 |
| WO | 2005052027 A1 | 6/2005 |
| WO | 2008/038747 A1 | 4/2008 |

OTHER PUBLICATIONS

Office Action issued Jul. 3, 2012 in Chinese Patent Application No. 200980135694.7 to Sumitomo Chemical Co., Ltd. with English translation.

Klarner G. et al., "Cross-linkable Polymers Based on Dialkylfluorenes," *Chem. Mater.*, vol. 11, 1999, pp. 1800-1805.

* cited by examiner

POLYMER COMPOUND COMPRISING ARYL REPEATING UNITS WITH CROSSLINKING PENDENT GROUPS AND LIGHT-EMITTING ELEMENT USING SAME

CROSS REFERENCE TO RELATED APPLICATIONS

This application is a National Stage of International Application No. PCT/JP2009/063456 filed on Jul. 29, 2009, which claims priority from Japanese Patent Application Nos. 2008-194522, filed Jul. 29, 2008 and 2009-037660 filed Feb. 20, 2009, the contents of all of which are incorporated herein by reference in their entirety

TECHNICAL FIELD

The present invention relates to a light-emitting device using a polymer compound (particularly, a fluorene polymer compound) and a light-emitting device using the same.

BACKGROUND ART

A high molecular-weight light-emitting material and a charge transport material are useful as e.g., a material for use in an organic layer of a light-emitting device and thus have been studied in various ways. In particular, to produce a layered light-emitting device, a polymer compound, which has a benzocyclobutene residue alone as a crosslinking group, capable of intra-molecularly/inter-molecularly crosslinking to harden the organic layer (Patent Literatures 1 and 2) has been proposed.

CITATION LIST

Patent Literature

Patent Literature 1: International Publication No. WO2005/035221
Patent Literature 2: JP 2008-106241 A

SUMMARY OF INVENTION

Technical Problem

However, the aforementioned polymer compound is insufficient in harden ability.
In the circumstances, an object of the present invention is to provide a polymer compound showing a sufficient harden ability.

Solution to Problem

The present invention firstly provides a polymer compound comprising a repeating unit represented by the following formula (I):

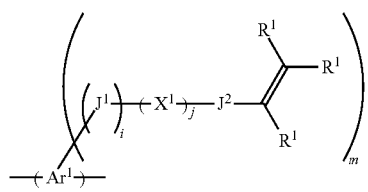

(I)

wherein $Ar^1$ represents an arylene group, a divalent heterocyclic group or a divalent aromatic amine; $J^1$ and $J^2$ each independently represent a direct bond, an alkylene group or a phenylene group; $X^1$ represents an oxygen atom or a sulfur atom; i is an integer of 0 to 3, j is 0 or 1 and m is 1 or 2; $R^1$ represents a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an acid imide group, a monovalent heterocyclic group, a carboxyl group, a substituted carboxyl group, a cyano group or a nitro group; a plurality of $R^1$ may be the same or different; and a plurality of $J^1$, $J^2$, $X^1$, i and j each may be the same or different, and a repeating unit represented by the following formula (II)

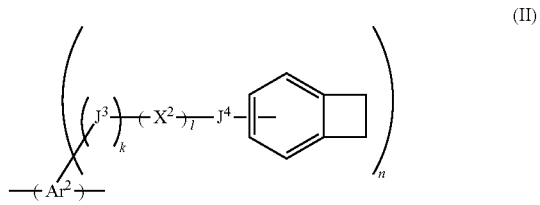

(II)

wherein $Ar^2$ represents a fluorene-diyl group; $J^3$ and $J^4$ each independently represent a direct bond, an alkylene group or a phenylene group; $X^2$ represents an oxygen atom or a sulfur atom; k is an integer of 0 to 3; l is 0 or 1; n is 1 or 2; a plurality of $J^3$, $J^4$, $X^2$, k and l each may be the same or different.

The present invention secondly provides a composition comprising the aforementioned polymer compound.

The present invention thirdly provides a liquid composition comprising the aforementioned polymer compound and a solvent.

The present invention fourthly provides a film comprising the aforementioned polymer compound and a film formed by crosslinking the aforementioned polymer compound.

The present invention fifthly provides a light-emitting device having electrodes comprising an anode and a cathode, a light-emitting layer provided between the electrodes and comprising the aforementioned polymer compound and/or a charge transport layer provided between the electrodes and comprising the aforementioned polymer compound, and a light-emitting device having electrodes comprising an anode and a cathode, a light-emitting layer provided between the electrodes and formed by crosslinking the aforementioned polymer compound and/or a charge transport layer provided between the electrodes and formed by crosslinking the aforementioned polymer compound.

The present invention sixthly provides a surface light source and a display having the aforementioned light-emitting device.

The present invention seventhly provides an organic transistor and organic photoelectric transducer formed by using the aforementioned polymer compound.

The present invention eighthly provides a compound represented by the following formula (XII):

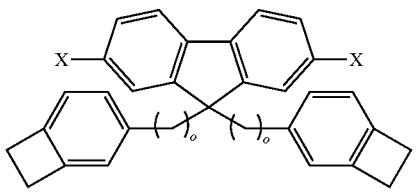

(XII)

wherein X represents a halogen atom, an alkylsulfonate group, an arylsulfonate group, an arylalkylsulfonate group, a boric acid residue or a boric acid ester residue; o is an integer of 4 to 10; two o may be the same or different; and two x may by the same or different.

The present invention ninthly provides a method for producing a compound represented by the above formula (XII), comprising reacting, in a base, a compound represented by the following formula (XIII):

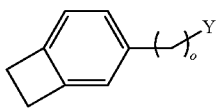

(XIII)

wherein Y represents a halogen atom; and o is the same as defined above, and a compound represented by the following formula (XIV):

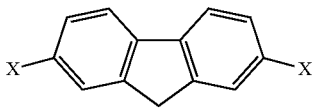

(XIV)

wherein X is the same as defined above.

The present invention tenthly provides a compound represented by the following formula (XV):

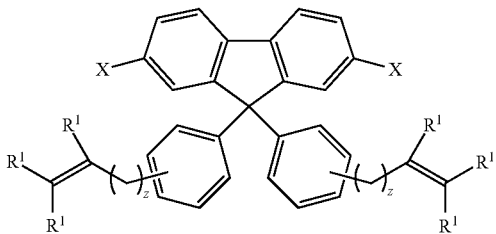

(XV)

wherein z represents an integer of 1 to 10; and X and $R^1$ are the same as defined above.

The present invention eleventhly provides a method for producing a compound represented by the following formula (XV):

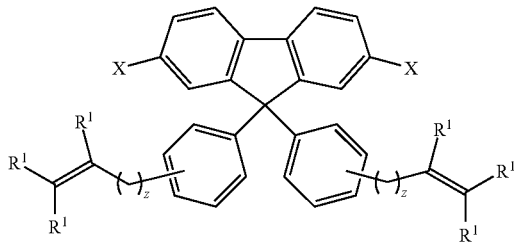

(XV)

wherein z represents an integer of 1 to 10; and X and $R^1$ are the same as defined above, comprising reacting, in a base, a compound represented by the following formula (XVI):

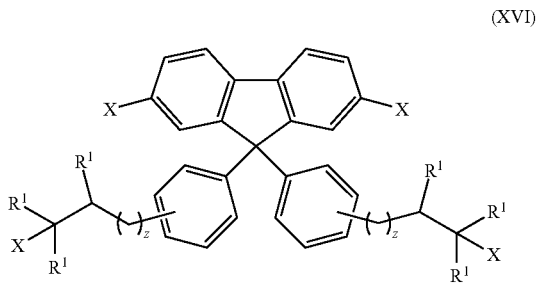

(XVI)

wherein X, $R^1$ and z are the same as defined above.

Advantageous Effects of Invention

The polymer compound of the present invention is a polymer compound having excellent harden ability (for example, thermosetting property). Furthermore, according to a preferable embodiment, the compound of the present invention is a polymer compound having an excellent life.

DESCRIPTION OF EMBODIMENTS

The polymer compound of the present invention is a polymer compound comprising a repeating unit represented by the above formula (I) and a repeating unit represented by the above formula (II). The repeating units represented by the above formula (I) and the repeating units represented by the above formula (II) each may be contained singly or as a mixture of two or more types.

<Polymer Compound>

The compound of the present invention, which is a polymer compound comprising repeating units represented by the above formula (I) and compound (II), may have, in view of harden ability, two or more repeating units represented by the above formula (I) and two or more repeating units represented by the above formula (II).

—A Repeating Unit Represented by the Formula (I)—

In the above formula (I), $Ar^1$ is preferably an arylene group in view of durability; in view of charge transport property, a divalent heterocyclic group is preferred, and in view of hole transport, a divalent aromatic amine is preferred.

In the above formula (I), the arylene group represented by $Ar^1$, is an atomic group obtained by removing two hydrogen atoms from an aromatic hydrocarbon. Examples thereof include an arylene group having a condensed ring and an arylene group to which an independent benzene ring or two or more condensed rings are bonded directly or via a vinylene group or the like. The arylene group may have a substituent. Examples of the substituent include an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an aryloxy group, an imine residue, a carbamoyl group, an acid imide group, a monovalent heterocyclic group, a carboxyl group, a substituted carboxyl group, a cyano group and a nitro group. In view of solubility, fluorescence property, easiness of synthesis of the compound to be obtained and characteristics of the device to be obtained, etc. an alkyl group, an alkoxy group, an aryl group, an aryloxy group, an arylalkyl group, an arylalkoxy group, a halogen atom and a cyano group is preferable.

In the arylene group represented by $Ar^1$, the number of carbon atoms of a moiety excluding a substituent is usually 6 to 60 and preferably 6 to 20, and the total number of carbon atoms of a moiety including the substituent is usually 6 to 100.

Examples of the arylene group represented by $Ar^1$ include a phenylene group (as shown in the following formulas 1 to 3), a naphthalenediyl group (as shown in the following formulas 4 to 13), an anthracene-diyl group (as shown in the following formulas 14 to 19), a biphenyl-diyl group (as shown in the following formulas 20 to 25), a terphenyl-diyl group (as shown in the following formulas 26 to 28), a condensed ring compound group (as shown in the following formulas 29 to 35), a fluorene-diyl group (as shown in the following formulas 36 to 38) and a benzofluorene-diyl (as shown in the following formulas 39 to 46). In view of durability, a phenylene group, a naphthalenediyl group, an anthracene-diyl group, a biphenyl-diyl group, a fluorene-diyl group and a benzofluorene-diyl group are preferable; a naphthalenediyl group, an anthracene-diyl group, a biphenyl-diyl group, a fluorene-diyl group and a benzofluorene-diyl group are more preferable; a naphthalenediyl group, an anthracene-diyl group, a fluorene-diyl group and a benzofluorene-diyl group are further preferable; a fluorene-diyl group and a benzofluorene-diyl group are particularly preferable; and a fluorene-diyl group is the most preferable. Furthermore, as the arylene group represented by $Ar^1$, in view of easiness of synthesizing the compound to be obtained, a phenylene group and a fluorene-diyl group are preferable, p-phenylene, m-phenylene and 2,7-fluorene-diyl groups are more preferable, and p-phenylene and 2,7-fluorene-diyl groups are particularly preferable. Note that the following groups may have a substituent.

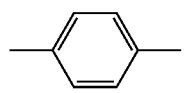

1

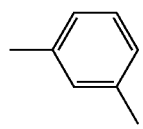

2

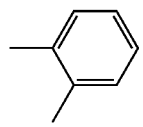

3

-continued

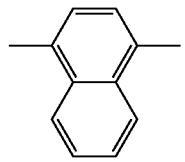

4

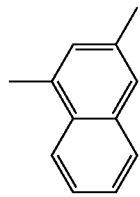

5

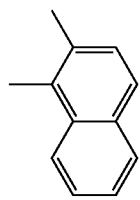

6

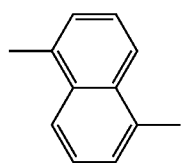

7

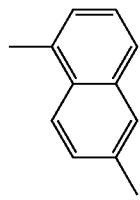

8

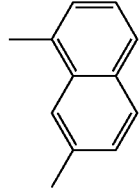

9

10

11

12
13
14
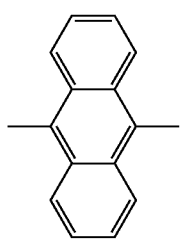
15
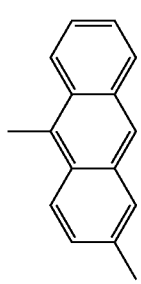
16
17
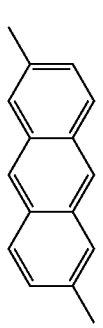
18
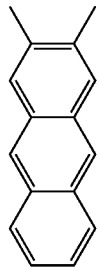
19
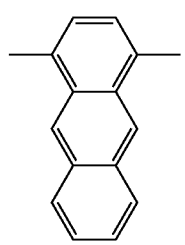
20
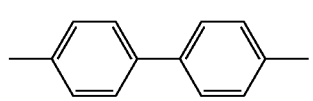
21
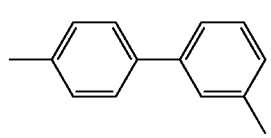
22
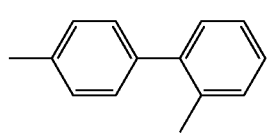
23
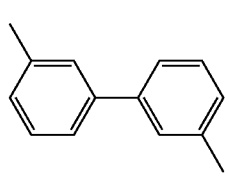
24
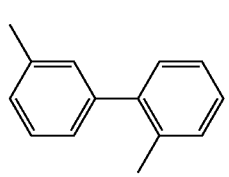
25
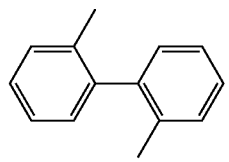
26
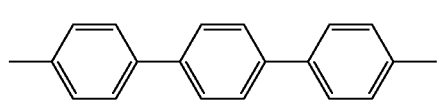

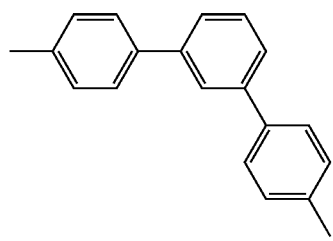
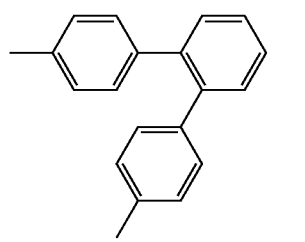
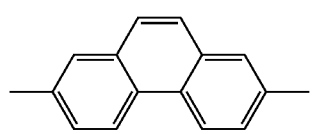
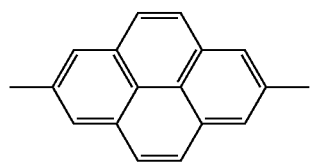
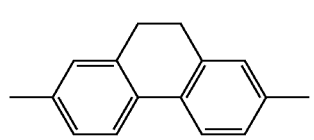
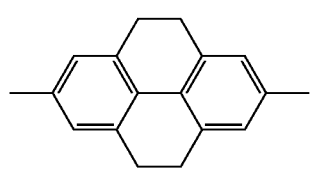
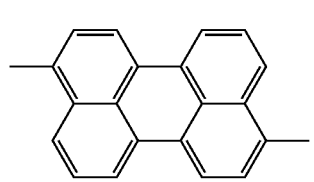
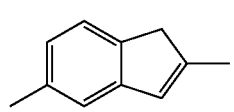
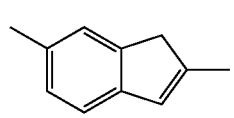
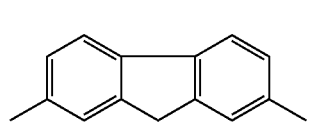
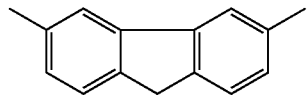
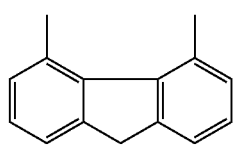
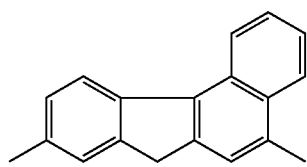
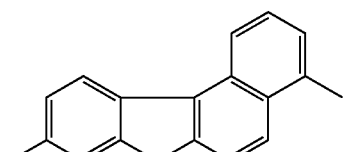
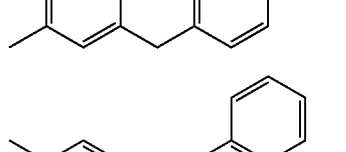
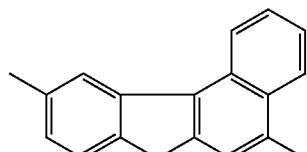
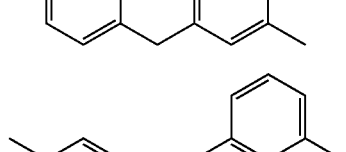
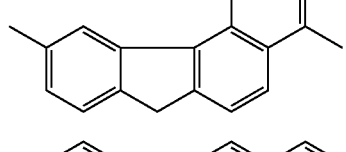
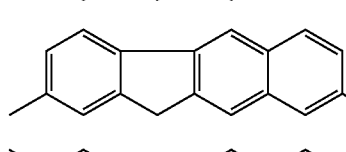
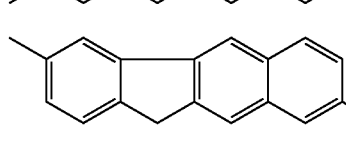
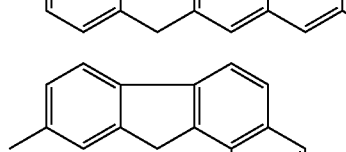
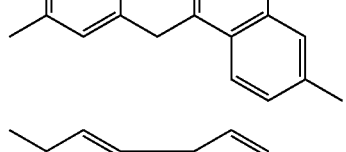
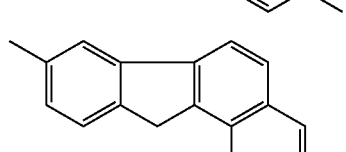
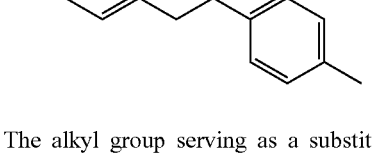
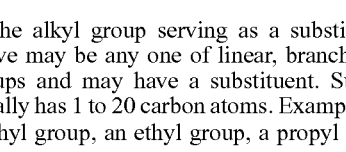
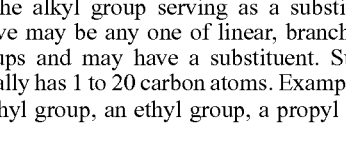
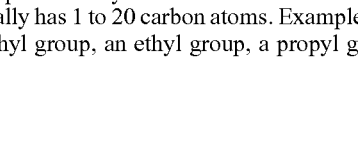
The alkyl group serving as a substituent as mentioned above may be any one of linear, branched and cyclic alkyl groups and may have a substituent. Such an alkyl group usually has 1 to 20 carbon atoms. Examples thereof include a methyl group, an ethyl group, a propyl group, an isopropyl group, a butyl group, an isobutyl group, a t-butyl group, a pentyl group, a hexyl group, a cyclohexyl group, a heptyl group, an octyl group, a 2-ethylhexyl group, a nonyl group, a decyl group, a 3,7-dimethyloctyl group, a lauryl group, a trifluoromethyl group, a pentafluoroethyl group, a perfluorobutyl group, a perfluorohexyl group and a perfluorooctyl group.

The alkoxy group serving as a substituent as mentioned above may be any one of linear, branched and cyclic alkoxy groups and may have a substituent. Such an alkoxy group usually has 1 to 20 carbon atoms. Examples thereof include a methoxy group, an ethoxy group, a propyloxy group, an isopropyloxy group, a butoxy group, an isobutoxy group, a t-butoxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, a lauryloxy group, a trifluoromethoxy group, a pentafluoroethoxy group, a perfluorobutoxy group, a perfluorohexyloxy group, a perfluorooctyloxy group, a methoxymethyloxy group and a 2-methoxyethyloxy group.

The alkylthio group serving as a substituent as mentioned above may be any one of linear, branched and cyclic alkylthio groups and may have a substituent. Such an alkylthio group usually has about 1 to 20 carbon atoms. Specific examples thereof include a methylthio group, an ethylthio group, a propylthio group, an isopropylthio group, a butylthio group, an isobutylthio group, a t-butylthio group, a pentylthio group, a hexylthio group, a cyclohexylthio group, a heptylthio group, an octylthio group, a 2-ethylhexylthio group, a nonylthio group, a decylthio group, a 3,7-dimethyloctylthio group, a laurylthio group and a trifluoromethylthio group.

The aryl group serving as a substituent as mentioned above is an atomic group, which is obtained by removing a single hydrogen atom from an aromatic hydrocarbon, includes an aryl group having a condensed ring, an aryl group to which an independent benzene ring or two or more condensed rings are bonded directly or via a vinylene group or the like. The aryl group usually has 6 to 60 carbon atoms and preferably 7 to 48 carbon atoms. Examples thereof include a phenyl group, a $C_1$ to $C_{12}$ alkoxyphenyl group ("$C_1$ to $C_{12}$ alkoxy" means that the number of carbon atoms of the alkoxy moiety is 1 to 12. The same is applied hereinafter), a $C_1$ to $C_{12}$ alkylphenyl group ("$C_1$ to $C_{12}$ alkyl" means that the number of carbon atoms of the alkyl moiety is 1 to 12. The same is applied hereinafter), a 1-naphthyl group, a 2-naphthyl group, a 1-anthracenyl group, a 2-anthracenyl group, a 9-anthracenyl group and a pentafluorophenyl group; and preferably a $C_1$ to $C_{12}$ alkoxyphenyl group and a $C_1$ to $C_{12}$ alkylphenyl group.

Examples of the $C_1$ to $C_{12}$ alkoxyphenyl group include a methoxyphenyl group, an ethoxyphenyl group, a propyloxyphenyl group, an isopropyloxyphenyl group, a butoxyphenyl group, an isobutoxyphenyl group, a t-butoxyphenyl group, a pentyloxyphenyl group, a hexyloxyphenyl group, a cyclohexyloxyphenyl group, a heptyloxyphenyl group, an octyloxyphenyl group, a 2-ethylhexyloxyphenyl group, a nonyloxyphenyl group, a decyloxyphenyl group, a 3,7-dimethyloctyloxyphenyl group and a lauryloxyphenyl group.

Examples of the $C_1$ to $C_{12}$ alkylphenyl group include a methylphenyl group, an ethylphenyl group, a dimethylphenyl group, a propylphenyl group, a mesityl group, a methylethylphenyl group, an isopropylphenyl group, a butylphenyl group, an isobutylphenyl group, a t-butylphenyl group, a pentylphenyl group, an isoamylphenyl group, a hexylphenyl group, a heptylphenyl group, an octylphenyl group, a nonylphenyl group, a decylphenyl group and a dodecylphenyl group.

The aryloxy group serving as a substituent as mentioned above usually has 6 to 60 carbon atoms and preferably 7 to 48 carbon atoms. Examples of the aryloxy group include a phenoxy group, a $C_1$ to $C_{12}$ alkoxyphenoxy group, a $C_1$ to $C_{12}$ alkylphenoxy group, a 1-naphthyloxy group, a 2-naphthyloxy group and a pentafluorophenyloxy group; and preferably a $C_1$ to $C_{12}$ alkoxyphenoxy group and a $C_1$ to $C_{12}$ alkylphenoxy group.

Examples of the $C_1$ to $C_{12}$ alkoxyphenoxy group include a methoxyphenoxy group, an ethoxyphenoxy group, a propyloxyphenoxy group, an isopropyloxyphenoxy group, a butoxyphenoxy group, an isobutoxyphenoxy group, a t-butoxyphenoxy group, a pentyloxyphenoxy group, a hexyloxyphenoxy group, a cyclohexyloxyphenoxy group, a heptyloxyphenoxy group, an octyloxyphenoxy group, a 2-ethylhexyloxyphenoxy group, a nonyloxyphenoxy group, a decyloxyphenoxy group, a 3,7-dimethyloctyloxyphenoxy group and a lauryloxyphenoxy group.

Examples of the $C_1$ to $C_{12}$ alkylphenoxy group include a methylphenoxy group, an ethylphenoxy group, a dimethylphenoxy group, a propylphenoxy group, a 1,3,5-trimethylphenoxy group, a methylethylphenoxy group, an isopropylphenoxy group, a butylphenoxy group, an isobutylphenoxy group, a t-butylphenoxy group, a pentylphenoxy group, an isoamylphenoxy group, a hexylphenoxy group, a heptylphenoxy group, an octylphenoxy group, a nonylphenoxy group, a decylphenoxy group and a dodecylphenoxy group.

The arylthio group serving as a substituent as mentioned above may have a substituent on the aromatic ring and usually has about 3 to 60 carbon atoms. Specific examples thereof include a phenylthio group, a $C_1$ to $C_{12}$ alkoxyphenylthio group, a $C_1$ to $C_{12}$ alkylphenylthio group, a 1-naphthylthio group, a 2-naphthylthio group and a pentafluorophenylthio group.

The arylalkyl group serving as a substituent as mentioned above may have a substituent and usually has about 7 to 60 carbon atoms. Specific examples thereof include a phenyl-$C_1$ to $C_{12}$ alkyl group, a $C_1$ to $C_{12}$ alkoxyphenyl-$C_1$ to $C_{12}$ alkyl group, a $C_1$ to $C_{12}$ alkylphenyl-$C_1$ to $C_{12}$ alkyl group, a 1-naphthyl-$C_1$ to $C_{12}$ alkyl group and a 2-naphthyl-$C_1$ to $C_{12}$ alkyl group.

The arylalkoxy group serving as a substituent as mentioned above may have a substituent and usually has about 7 to 60 carbon atoms. Specific examples thereof include a phenyl-$C_1$ to $C_{12}$ alkoxy group, a $C_1$ to $C_{12}$ alkoxyphenyl-$C_1$ to $C_{12}$ alkoxy group, a $C_1$ to $C_{12}$ alkylphenyl-$C_1$ to $C_{12}$ alkoxy group, a 1-naphthyl-$C_1$ to $C_{12}$ alkoxy group and a 2-naphthyl-$C_1$ to $C_{12}$ alkoxy group.

The arylalkylthio group serving as a substituent as mentioned above may have a substituent and usually has about 7 to 60 carbon atoms. Specific examples thereof include a phenyl-$C_1$ to $C_{12}$ alkylthio group, a $C_1$ to $C_{12}$ alkoxyphenyl-$C_1$ to $C_{12}$ alkylthio group, a $C_1$ to $C_{12}$ alkylphenyl-$C_1$ to $C_{12}$ alkylthio group, a 1-naphthyl-$C_1$ to $C_{12}$ alkylthio group and a 2-naphthyl-$C_1$ to $C_{12}$ alkylthio group.

The arylalkenyl group serving as a substituent as mentioned above usually has about 8 to 60 carbon atoms. Specific examples thereof include a phenyl-$C_2$ to $C_{12}$ alkenyl group, a $C_1$ to $C_{12}$ alkoxyphenyl-$C_2$ to $C_{12}$ alkenyl group, a $C_1$ to $C_{12}$ alkylphenyl-$C_2$ to $C_{12}$ alkenyl group, a 1-naphthyl-$C_2$ to $C_{12}$ alkenyl group and a 2-naphthyl-$C_2$ to $C_{12}$ alkenyl group. A $C_1$ to $C_{12}$ alkoxyphenyl-$C_2$ to $C_{12}$ alkenyl group and a $C_1$ to $C_{12}$ alkylphenyl-$C_2$ to $C_{12}$ alkenyl group are preferable.

The arylalkynyl group serving as a substituent as mentioned above usually has about 8 to 60 carbon atoms. Specific examples thereof include a phenyl-$C_2$ to $C_{12}$ alkynyl group, a $C_1$ to $C_{12}$ alkoxyphenyl-$C_2$ to $C_{12}$ alkynyl group, a $C_1$ to $C_{12}$ alkylphenyl-$C_2$ to $C_{12}$ alkynyl group, a 1-naphthyl-$C_2$ to $C_{12}$ alkynyl group and a 2-naphthyl-$C_2$ to $C_{12}$ alkynyl group. A $C_1$ to $C_{12}$ alkoxyphenyl-$C_2$ to $C_{12}$ alkynyl group and a $C_1$ to $C_{12}$ alkylphenyl-$C_2$ to $C_{12}$ alkynyl group are preferable.

The substituted amino group serving as a substituent as mentioned above may be an amino group substituted with one or two groups selected from an alkyl group, an aryl group, an arylalkyl group and a monovalent heterocyclic group. The alkyl group, aryl group, arylalkyl group or monovalent heterocyclic group may have a substituent. The number of carbon atoms of the substituted amino group excluding the number of carbon atoms of a substituent is usually about 1 to 60 and preferably 2 to 48 carbon atoms.

Specific examples thereof include a methylamino group, a dimethylamino group, an ethylamino group, a diethylamino group, a propylamino group, a dipropylamino group, an isopropylamino group, a diisopropylamino group, a butylamino group, an s-butylamino group, an isobutylamino group, a t-butylamino group, a pentylamino group, a hexylamino group, a cyclohexylamino group, a heptylamino group, an octylamino group, a 2-ethylhexylamino group, a nonylamino group, a decylamino group, a 3,7-dimethyloctylamino group, a laurylamino group, a cyclopentylamino group, a dicyclopentylamino group, a dicyclohexylamino group, a pyrrolidyl group, a piperidyl group, a ditrifluoromethylamino group, a phenylamino group, a diphenylamino group, a $C_1$ to $C_{12}$ alkoxyphenylamino group, a di($C_1$ to $C_{12}$ alkoxyphenyl)amino group, a di($C_1$ to $C_{12}$ alkylphenyl)amino group, a 1-naphthylamino group, a 2-naphthylamino group, a pentafluorophenylamino group, a pyridylamino group, a pyridazinylamino group, a pyrimidylamino group, a pyrazylamino group, a triazylamino group, a phenyl-$C_1$ to $C_{12}$ alkylamino group, a $C_1$ to $C_{12}$ alkoxyphenyl-$C_1$ to $C_{12}$ alkylamino group, a $C_1$ to $C_{12}$ alkylphenyl-$C_1$ to $C_{12}$ alkylamino group, a di($C_1$ to $C_{12}$ alkoxyphenyl-$C_1$ to $C_{12}$ alkyl)amino group, a di($C_1$ to $C_{12}$ alkylphenyl-$C_1$ to $C_{12}$ alkyl)amino group, a 1-naphthyl-$C_1$ to $C_{12}$ alkylamino group and a 2-naphthyl-$C_1$ to $C_{12}$ alkylamino group.

The substituted silyl group serving as a substituent as mentioned above may be a silyl group substituted with 1, 2 or 3 groups selected from an alkyl group, an aryl group, an arylalkyl group and a monovalent heterocyclic group. The number of carbon atoms of the substituted silyl group is usually about 1 to 60 and preferably 3 to 48. Note that the alkyl group, aryl group, arylalkyl group or monovalent heterocyclic group may have a substituent.

Specific examples thereof include a trimethylsilyl group, a triethylsilyl group, a tripropylsilyl group, a tri-isopropylsilyl group, a dimethyl-isopropylsilyl group, a diethyl-isopropylsilyl group, a t-butyldimethylsilyl group, a pentyldimethylsilyl group, a hexyldimethylsilyl group, a heptyldimethylsilyl group, an octyldimethylsilyl group, a 2-ethylhexyl-dimethylsilyl group, a nonyldimethylsilyl group, a decyldimethylsilyl group, a 3,7-dimethyloctyl-dimethylsilyl group, a lauryldimethylsilyl group, a phenyl-$C_1$ to $C_{12}$ alkylsilyl group, a $C_1$ to $C_{12}$ alkoxyphenyl-$C_1$ to $C_{12}$ alkylsilyl group, a $C_1$ to $C_{12}$ alkylphenyl-$C_1$ to $C_{12}$ alkylsilyl group, a 1-naphthyl-$C_1$ to $C_{12}$ alkylsilyl group, a 2-naphthyl-$C_1$ to $C_{12}$ alkylsilyl group, a phenyl-$C_1$ to $C_{12}$ allyldimethylsilyl group, a triphenylsilyl group, a tri-p-xylylsilyl group, a tribenzylsilyl group, a diphenylmethylsilyl group, a t-butyldiphenylsilyl group and a dimethylphenylsilyl group.

Examples of a halogen atom serving as a substituent as mentioned above include a fluorine atom, a chlorine atom, a bromine atom and an iodine atom.

The acyl group serving as a substituent as mentioned above usually has about 2 to 20 carbon atoms and preferably 2 to 18 carbon atoms. Specific examples thereof include an acetyl group, a propionyl group, a butyryl group, an isobutyryl group, a pivaloyl group, a benzoyl group, a trifluoroacetyl group and a pentafluorobenzoyl group.

The acyloxy group serving as a substituent as mentioned above usually has about 2 to 20 carbon atoms and preferably 2 to 18 carbon atoms. Specific examples thereof include an acetoxy group, a propionyloxy group, a butyryloxy group, an isobutyryloxy group, a pivaloyloxy group, a benzoyloxy group, a trifluoroacetyloxy group and a pentafluorobenzoyloxy group.

The imine residue serving as a substituent as mentioned above refers to a residue obtained by removing a single hydrogen atom from an imine compound (which refers to an organic compound having —N=C— in the molecule. Examples thereof include aldimine, ketimine and a compound obtained by substituting a hydrogen atom on N of these with e.g., an alkyl group) and usually has about 2 to 20 carbon atoms and preferably 2 to 18 carbon atoms. Specific examples include groups represented by the following structural formulas.

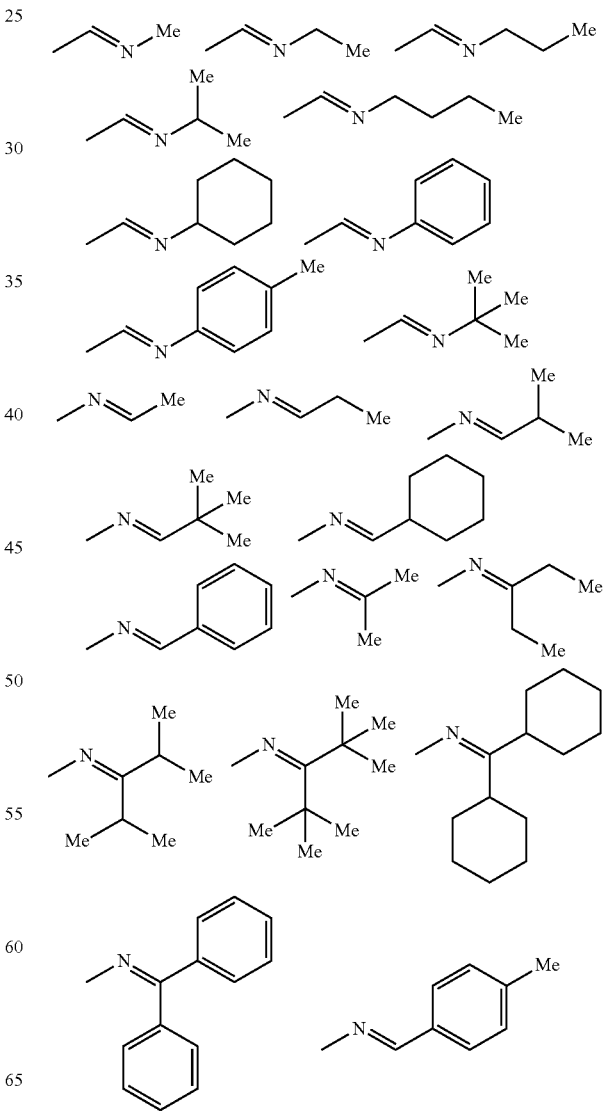

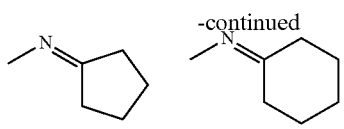

The carbamoyl group serving as a substituent as mentioned above usually has about 2 to 20 carbon atoms and preferably 2 to 18 carbon atoms. Specific examples thereof include a formamide group, an acetamide group, a propioamide group, a butyroamide group, a benzamide group, a trifluoroacetamide group, a pentafluorobenzamide group, a diformamide group, a diacetamide group, a dipropioamide group, a dibutyroamide group, a dibenzamide group, a ditrifluoroacetamide group and a dipentafluorobenzamide group.

Examples of the acid imide group serving as a substituent as mentioned above include a residue obtained by removing a hydrogen atom bound to the nitrogen atom of the acid imide and having about 4 to 20 carbon atoms. Specific examples thereof include the groups shown below.

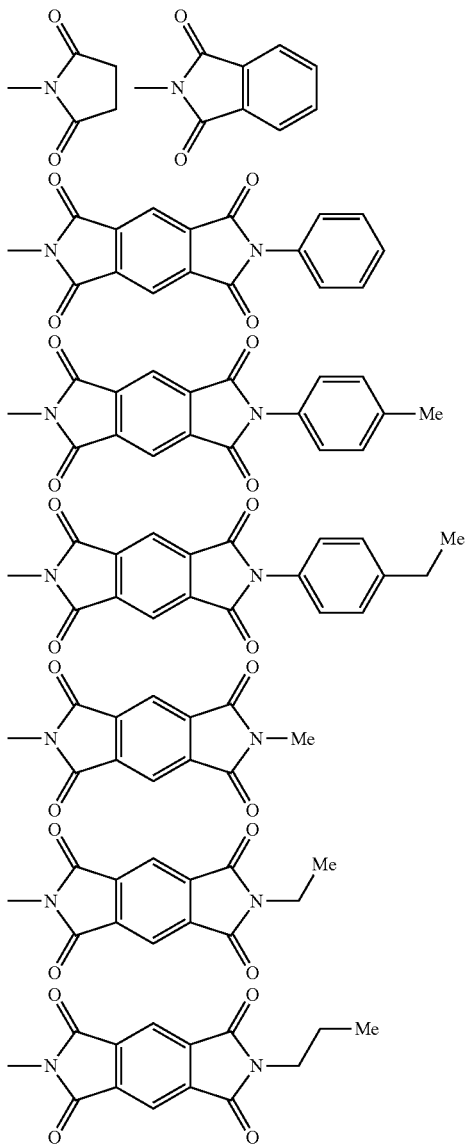

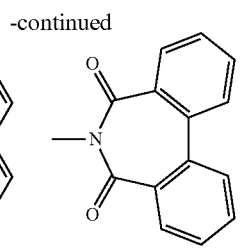

The monovalent heterocyclic group serving as a substituent as mentioned above refers to a remaining atomic group obtained by removing a single hydrogen atom from a heterocyclic compound and usually having about 4 to 60 carbon atoms and preferably 4 to 20 carbon atoms. Of the monovalent heterocyclic groups, a monovalent aromatic heterocyclic group is preferable. Note that the number of carbon atoms of a substituent is not included in the number of carbon atoms of a heterocyclic group. The heterocyclic compound herein refers to an organic compound having a ring structure, which is not only constituted of a carbon atom but also contains a hetero atom such as oxygen, sulfur, nitrogen, phosphorus and boron, within the ring. Specific examples thereof include a thienyl group, a $C_1$ to $C_{12}$ alkylthienyl group, a pyrrolyl group, a furyl group, a pyridyl group, a $C_1$ to $C_{12}$ alkylpyridyl group, a piperidyl group, a quinolyl group and an isoquinolyl group. A thienyl group, a $C_1$ to $C_{12}$ alkyl thienyl group, a pyridyl group and a $C_1$ to $C_{12}$ alkyl pyridyl group are preferable.

Examples of the substituted carboxyl group serving as a substituent as mentioned above refers to a carboxyl group substituted with an alkyl group, an aryl group, an arylalkyl group or a monovalent heterocyclic group and usually having about 2 to 60 carbon atoms and preferably 2 to 48 carbon atoms. Specific examples thereof include a methoxycarbonyl group, an ethoxycarbonyl group, a propoxycarbonyl group, an isopropoxycarbonyl group, a butoxycarbonyl group, an isobutoxycarbonyl group, a t-butoxycarbonyl group, a pentyloxycarbonyl group, a hexyloxycarbonyl group, a cyclohexyloxycarbonyl group, a heptyloxycarbonyl group, an octyloxycarbonyl group, a 2-ethylhexyloxycarbonyl group, a nonyloxycarbonyl group, a decyloxycarbonyl group, a 3,7-dimethyloctyloxycarbonyl group, a dodecyloxycarbonyl group, a trifluoromethoxycarbonyl group, a pentafluoroethoxycarbonyl group, a perfluorobutoxycarbonyl group, a perfluorohexyloxycarbonyl group, a perfluorooctyloxycarbonyl group, a phenoxycarbonyl group, a naphthoxycarbonyl group and a pyridyloxycarbonyl group. Note that the alkyl group, aryl group, arylalkyl group or monovalent heterocyclic group may have a substituent. The number of carbon atoms of the substituent is not included in the number of carbon atoms of the substituted carboxyl group.

In the above formula (I), the divalent heterocyclic group represented by $Ar^1$ refers to the remaining atomic group obtained by removing two hydrogen atoms from a heterocyclic compound. The divalent heterocyclic group may have a substituent.

The heterocyclic compound refers to an organic compound having a ring structure, which is not only constituted of a carbon atom but also contains a hetero atom such as oxygen, sulfur, nitrogen, phosphorus, boron and arsenic within a ring. As the divalent heterocyclic group, a divalent aromatic heterocyclic group is preferable. Examples of the aforementioned substituent include an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an acid imide group, a monovalent heterocyclic group, a carboxyl group, a substituted carboxyl group, a cyano group and a nitro group. In view of solubility of, fluorescent property of, easiness of synthesizing the polymer compound to be obtained and characteristics of the device to be obtained, etc., an alkyl group, an alkoxy group, an aryl group, an aryloxy group, an arylalkyl group, an arylalkoxy group, a halogen atom and a cyano group are preferable. These groups and atoms are defined as described above.

In the divalent heterocyclic group represented by $Ar^1$, the number of carbon atoms of the moiety excluding a substituent is usually, 3 to 60 and the total number of carbon atoms including a substituent is usually 3 to 100.

Examples of the divalent heterocyclic group represented by $Ar^1$ include the following groups. Note that the following groups may have a substituent.

Divalent heterocyclic group containing a nitrogen atom as a hetero atom: a pyridine-diyl group (as shown in the following formulas 101 to 104), a diazaphenylene group (as shown in the following formulas 105 to 108), a triazine-diyl group (as shown in the following formula 109), a quinoline-diyl group (as shown in the following formulas 110 to 114), a quinoxaline-diyl group (as shown in the following formulas 115 to 119), an acridinediyl group (the following formulas 120 to 123), a bipyridyl-diyl group (the following formulas 124 to 126), a phenanthroline diyl group (the following formulas 127 and 128).

A group containing an oxygen atom, a sulfur atom, a nitrogen atom, a silicon atom, etc. as a hetero atom and having a fluorene structure (as shown in the following formulas 129 to 136).

A 5-membered heterocyclic group containing an oxygen atom, a sulfur atom, a nitrogen atom and a silicon atom, etc. as a hetero atom (as shown in the following formulas 137 to 140).

A 5-membered condensed heterocyclic group containing an oxygen atom, a sulfur atom, a nitrogen atom and a silicon atom, etc. as a hetero atom (as shown in the following formulas 141 to 158).

A 5-membered heterocyclic group containing an oxygen atom, a sulfur atom, a nitrogen atom and a silicon atom, etc. as a hetero atom and bound at the α position of the hetero atom to form a dimer or an oligomer (as shown in the following formulas 159 to 160).

A 5-membered heterocyclic group containing an oxygen atom, a sulfur atom, a nitrogen atom and a silicon atom, etc. as a hetero atom and bound at the α position of the hetero atom to a phenyl group (as shown in the following formulas 161 to 166).

A 5-membered condensed heterocyclic group containing an oxygen atom, a sulfur atom and a nitrogen atom, etc. as a hetero atom and substituted with a phenyl group, a furyl group, a thienyl group (the following formulas 167 to 172).

A 6-membered heterocyclic group containing an oxygen atom and nitrogen atom as a hetero atom (as shown in the following formulas 173-176).

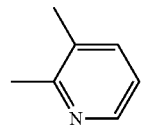

101

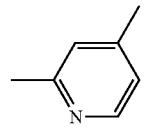

102

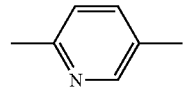

103

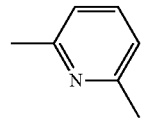

104

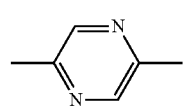

105

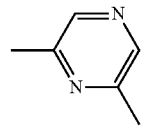

106

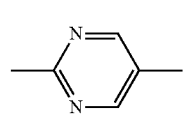

107

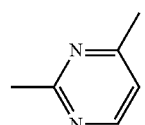

108

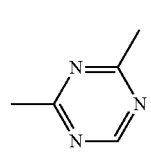

109

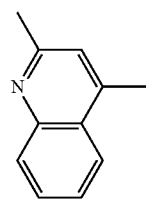

110

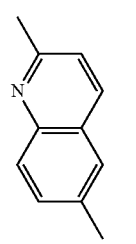

111

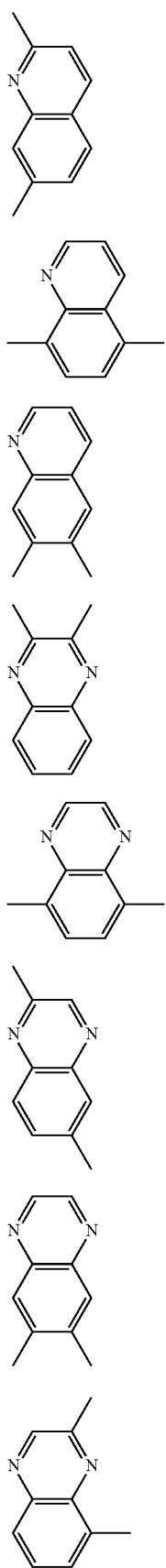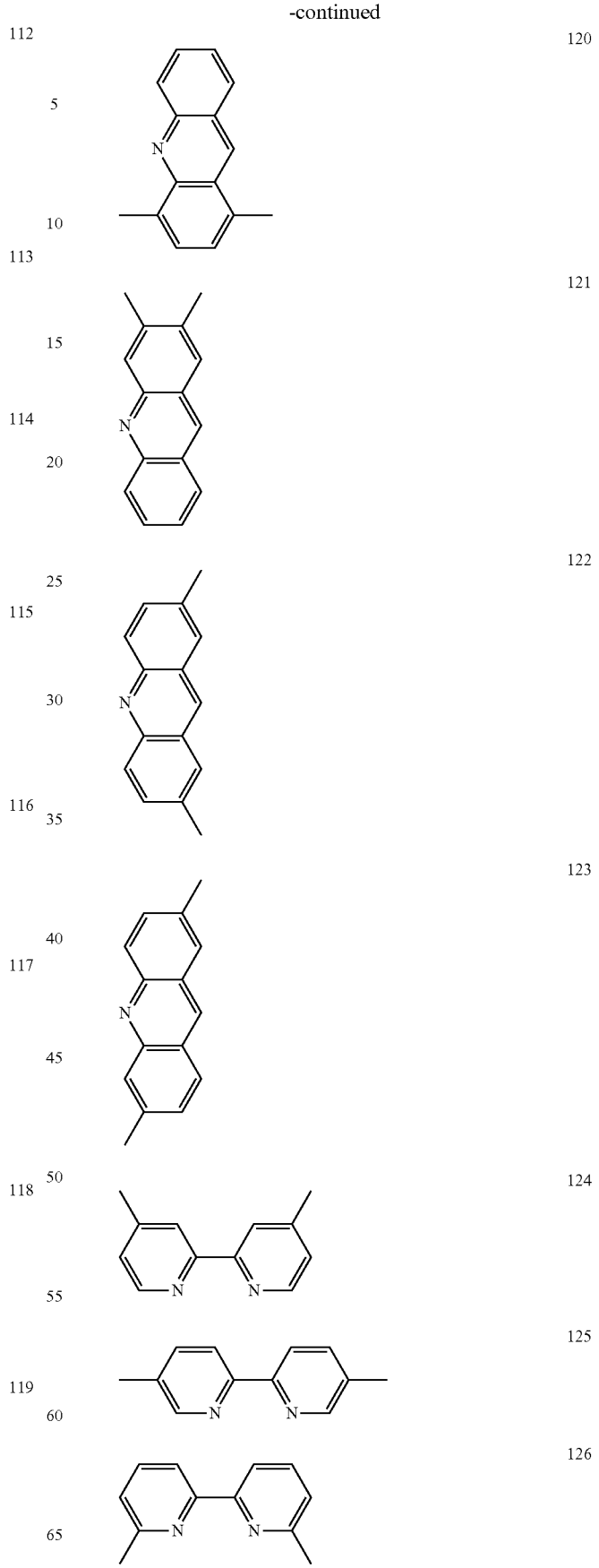

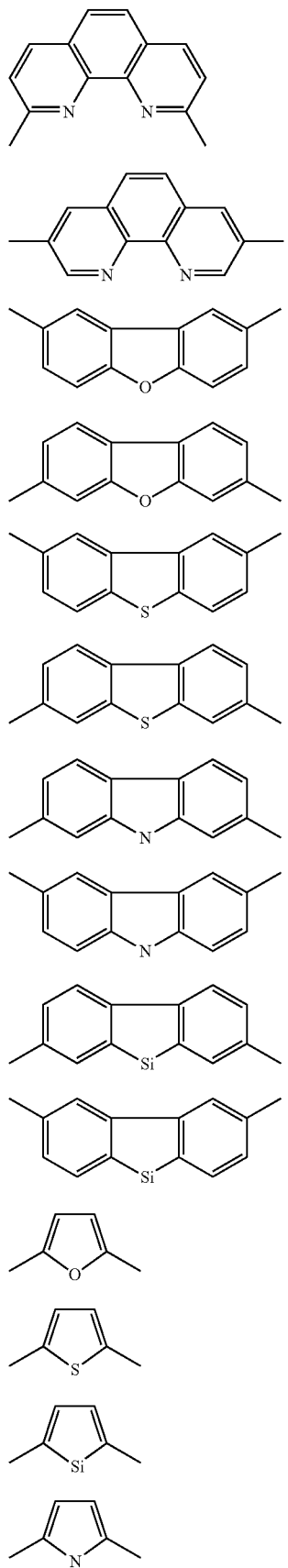
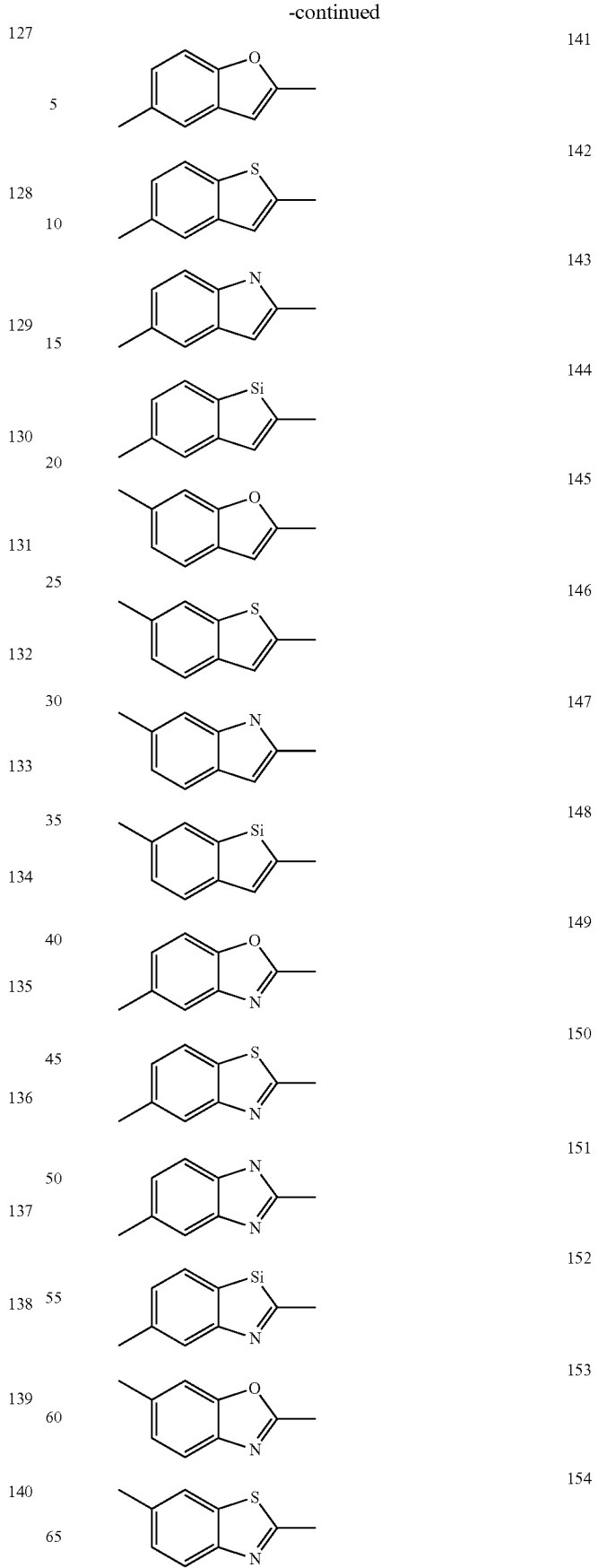

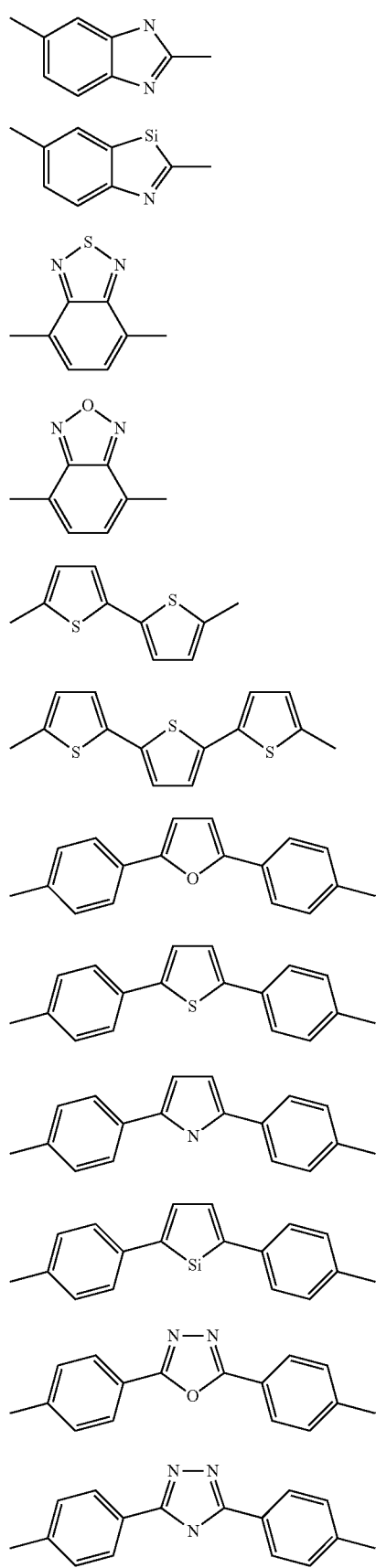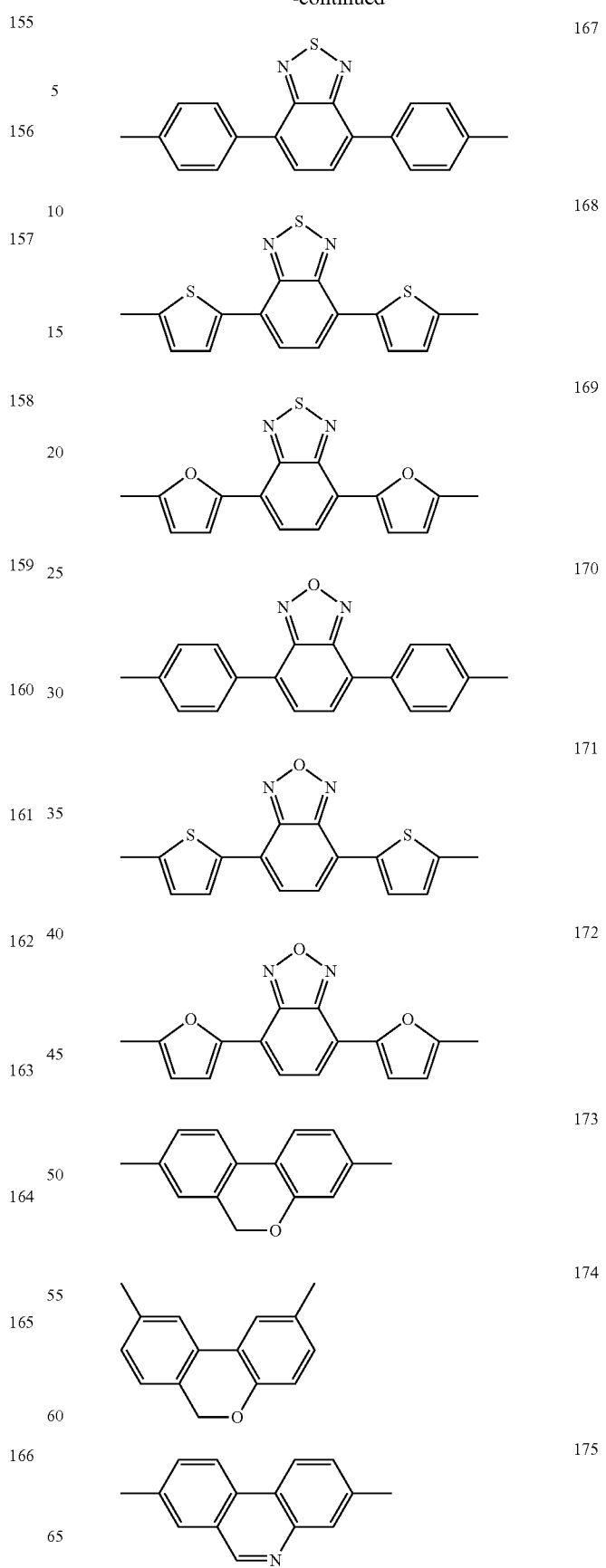

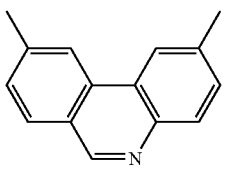

176

The divalent heterocyclic group represented by Ar¹ is, in view of charge transport property, preferably a divalent group represented by the following formula (I)-X:

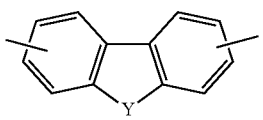

(I)-X wherein Y represents an oxygen atom, a sulfur atom, —N($R^a$)—, —O—C($R^b$)($R^c$)—, or —Si($R^d$)($R^e$)—; $R^a$, $R^b$, $R^c$, $R^d$ and $R^e$ each independently represent a hydrogen atom, an alkyl group, an alkoxy group, an aryl group or an arylalkyl group; and the formula may have a substituent.

When the above formula (I)-X has a substituent, examples of the substituent include an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an acid imide group, a monovalent heterocyclic group, a carboxyl group, a substituted carboxyl group, a cyano group and a nitro group. In view of solubility, fluorescent property, easiness of synthesizing the polymer compound to be obtained and characteristics of the device to be obtained, etc., an alkyl group, an alkoxy group, an aryl group, an aryloxy group, an arylalkyl group, an arylalkoxy group, a halogen atom and a cyano group are preferable. These groups are the same as defined above.

In the above formula (I)-X, in view of easiness of synthesizing the compound of the present invention, Y is preferably an oxygen atom, a sulfur atom and —N($R^a$)— and more preferably an oxygen atom and —N($R^a$)—.

A divalent group represented by the above formula (I)-X is preferably a divalent group represented by the following formula (I)-Y or the following formula (I)-Z, since a particularly high charge transport property can be obtained.

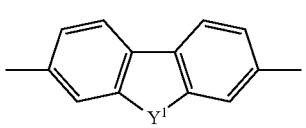

(I)-Y wherein Y¹ represents an oxygen atom, a sulfur atom, —N($R^a$)—, —O—C($R^b$)($R^c$)— or —Si($R^d$)($R^e$)—; and the formula may have a substituent.

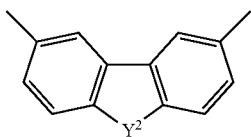

(I)-Z wherein Y¹ represents an oxygen atom, a sulfur atom, —N($R^a$)—, —O—C($R^b$)($R^c$)— or —Si($R^d$)($R^e$)—; and the formula may have a substituent.

When the above formulas (I)-Y and (I)-Z have a substituent, examples of the substituent include an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an acid imide group, a monovalent heterocyclic group, a carboxyl group, a substituted carboxyl group, a cyano group and a nitro group. In view of solubility, fluorescent property, easiness of synthesizing the polymer compound to be obtained and characteristics of the device to be obtained, etc., an alkyl group, an alkoxy group, an aryl group, an aryloxy group, an arylalkyl group, an arylalkoxy group, a halogen atom and a cyano group are preferable. These groups are the same as defined above.

In the above formula (I)-Y, in view of easiness of synthesizing the compound of the present invention, Y¹ is preferably an oxygen atom, a sulfur atom, or —N($R^a$)—, more preferably an oxygen atom or —N($R^a$)— and particularly preferably an oxygen atom.

In the above formula (I)-Z, in view of easiness of synthesizing the compound of the present invention, Y² is preferably an oxygen atom, a sulfur atom or —N($R^a$)—, more preferably a sulfur atom or —N($R^a$)— and particularly preferably —N($R^a$)—.

The divalent aromatic amine group represented by Ar¹ refers to the remaining atomic group obtained by removing two hydrogen atoms from an aromatic amine, having usually 5 to 100 carbon atoms and preferably 15 to 60 carbon atoms. The divalent aromatic amine group may have a substituent. Note that the number of carbon atoms of a substituent is not included in the number of carbon atoms of an aromatic amine. The substituent include an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an acid imide group, a monovalent heterocyclic group, a carboxyl group, a substituted carboxyl group, a cyano group and a nitro group. In view of solubility of, fluorescence property of, easiness of synthesizing the polymer compound to be obtained and characteristics of the device to be obtained, an alkyl group, an alkoxy group, an aryl group, an aryloxy group, an arylalkyl group, an arylalkoxy group, a halogen atom and cyano group are preferable. These groups and atoms are the same as defined above.

Examples of the divalent aromatic amine group represented by Ar¹ include divalent groups represented by the following formulas 201 to 210. Note that the following groups may have a substituent.

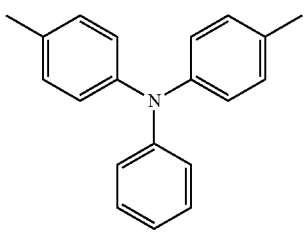

201

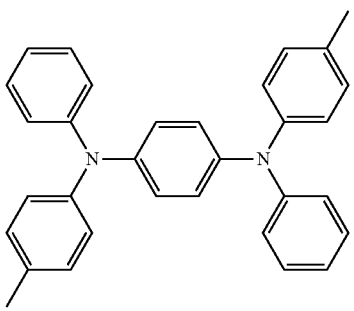

202

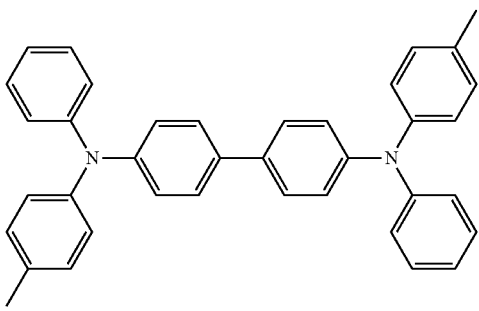

203

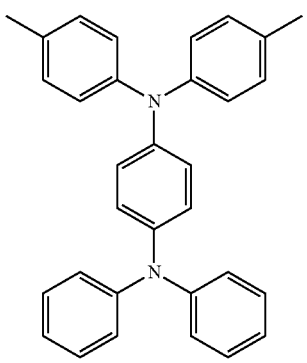

204

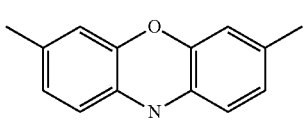

205

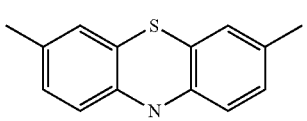

206

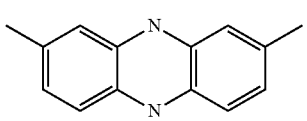

207

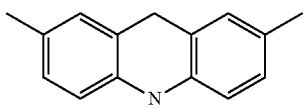

208

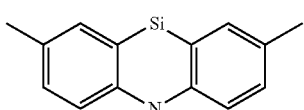

209

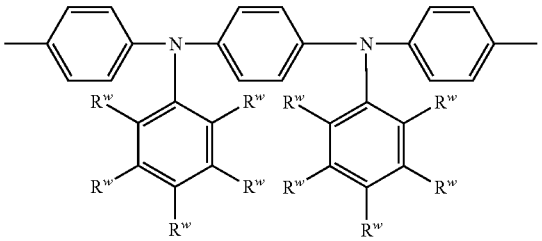

210

The divalent aromatic amine group represented by $Ar^1$ is, in view of hole transport property, preferably a divalent group represented by the following formula (I)-V:

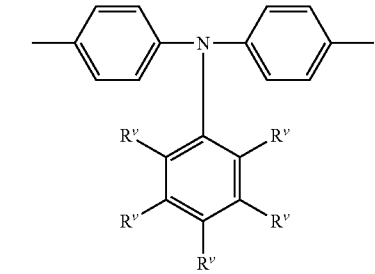

(I)-V wherein $R^V$ represents a hydrogen atom, an alkyl group, an alkoxy group or a substituted amino group; and five $R^V$ may be the same or different, or a divalent group represented by the following formula (I)-W:

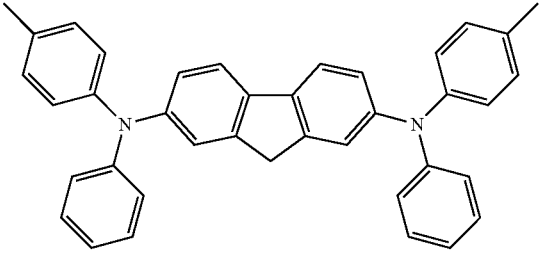

(I)-W wherein $R^W$ represents a hydrogen atom, an alkyl group, an alkoxy group or a substituted amino group; and ten $R^W$ may be the same or different.

In the above formulas (I)-V and (I)-W, the alkyl group, alkoxy group and substituted amino group represented by $R^V$ and $R^W$ are the same as defined above.

In the above formula (I), the alkylene group represented by $J^1$ and $J^2$ may be a linear or branched group. Examples of the alkylene group include methylene, 1,2-ethylene, 1,3-propylene, 1,3-butylene, 1,4-butylene, 1,3-pentylene, 1,4-pentylene, 1,5-pentylene, 1,4-hexylene, 1,6-hexylene, 1,7-heptylene, 1,6-octylene and 1,8-octylene.

In the above formula (I), the phenylene group represented by $J^1$ and $J^2$ may have a substituent. Examples of the phenylene group include an o-phenylene, m-phenylene and p-phenylene. Examples of the substituent which the phenylene group may have include an alkyl group, an alkoxy group, a halogen atom and a cyano group. The alkyl group, alkoxy group and halogen atom serving as a substituent are the same as defined above.

In the above formula (I), in view of easiness of synthesizing the raw-material compound, $J^1$ is preferably a direct bond or a phenylene group.

In the above formula (I), in view of easiness of synthesizing the raw-material compound, $J^2$ is preferably a direct bond or alkylene group.

In the above formula (I), $X^1$ represents an oxygen atom or a sulfur atom and preferably an oxygen atom in view of easiness of synthesizing a raw material compound.

In the above formula (I), $R^1$ represents the alkyl group, alkoxy group, alkylthio group, aryl group, aryloxy group, arylthio group, arylalkyl group, arylalkoxy group, arylalkylthio group, arylalkenyl group, arylalkynyl group, amino group, substituted amino group, silyl group, substituted silyl group, halogen atom, acyl group, acyloxy group, imine residue, carbamoyl group, acid imide group, monovalent heterocyclic group, carboxyl group, substituted carboxyl group, cyano group or nitro group. However, in view of harden ability of the polymer compound, a hydrogen atom, an alkyl group, an alkoxy group or a halogen atom are preferable; a hydrogen atom, an alkyl group and a halogen atom are more preferable; a hydrogen atom and an alkyl group are further preferable; and a hydrogen atom is particularly preferable. These groups are the same as defined above.

In the above formula (I), m is 1 or 2 and preferably 2 in view of easiness of synthesizing a monomer serving as a raw material.

In the above formula (I), i is an integer of 0 to 3, preferably 0 and 1 and particularly preferably 0, in view of easiness of synthesizing a monomer serving as a raw material.

In the above formula (I), j is 0 or 1, preferably 0 in view of easiness of synthesizing a monomer serving as a raw material.

Examples of the repeating unit represented by the above formula (I) include the repeating units represented by the following formulas (I-1) to (I-38):

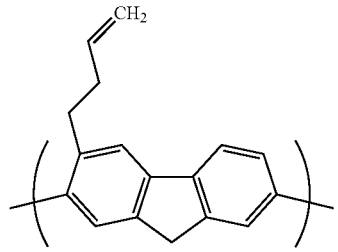

(I-1)

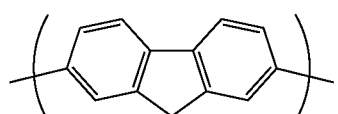

(I-2)

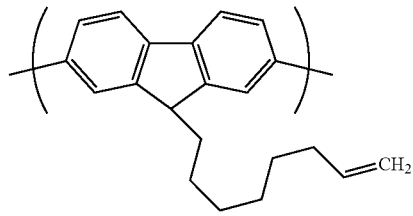

(I-3)

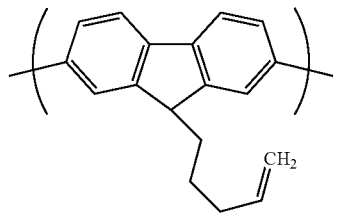

(I-4)

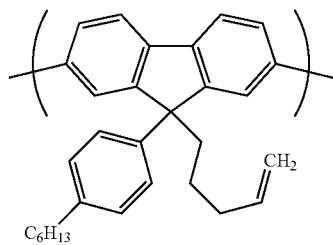

(I-5)

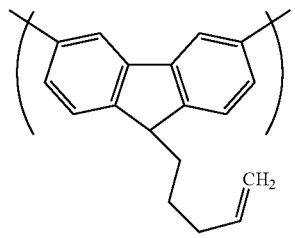

(I-6)

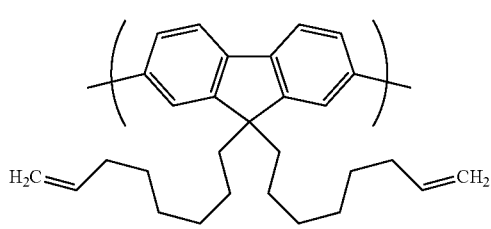

(I-7)

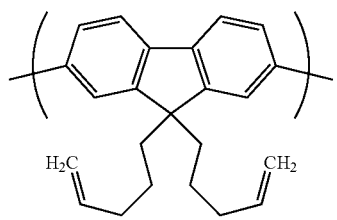

(I-8)

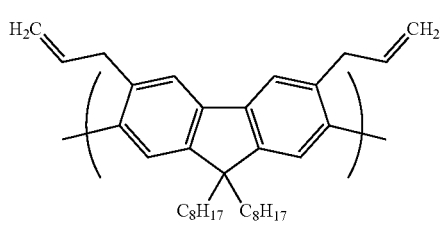

(I-9)

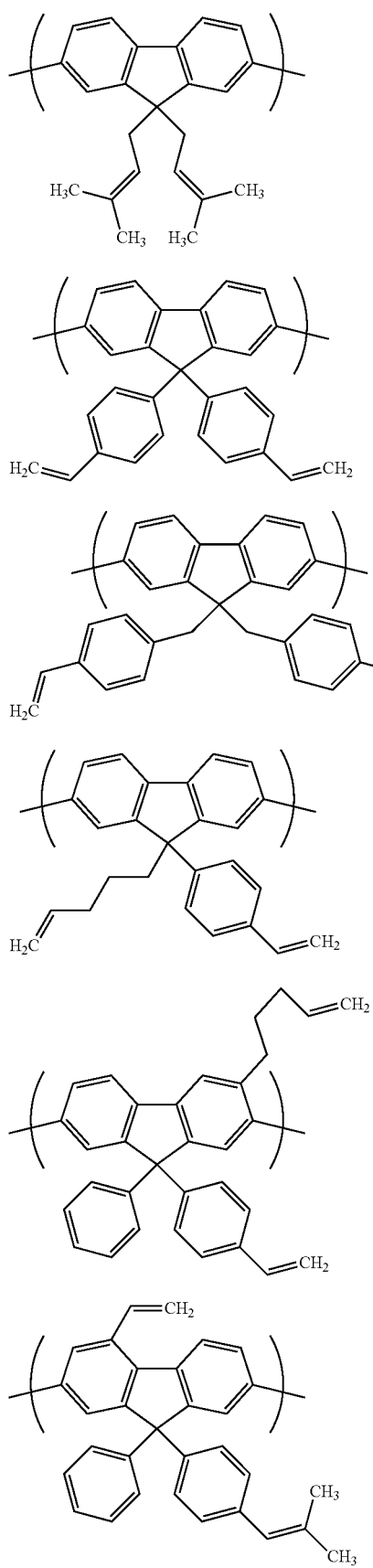
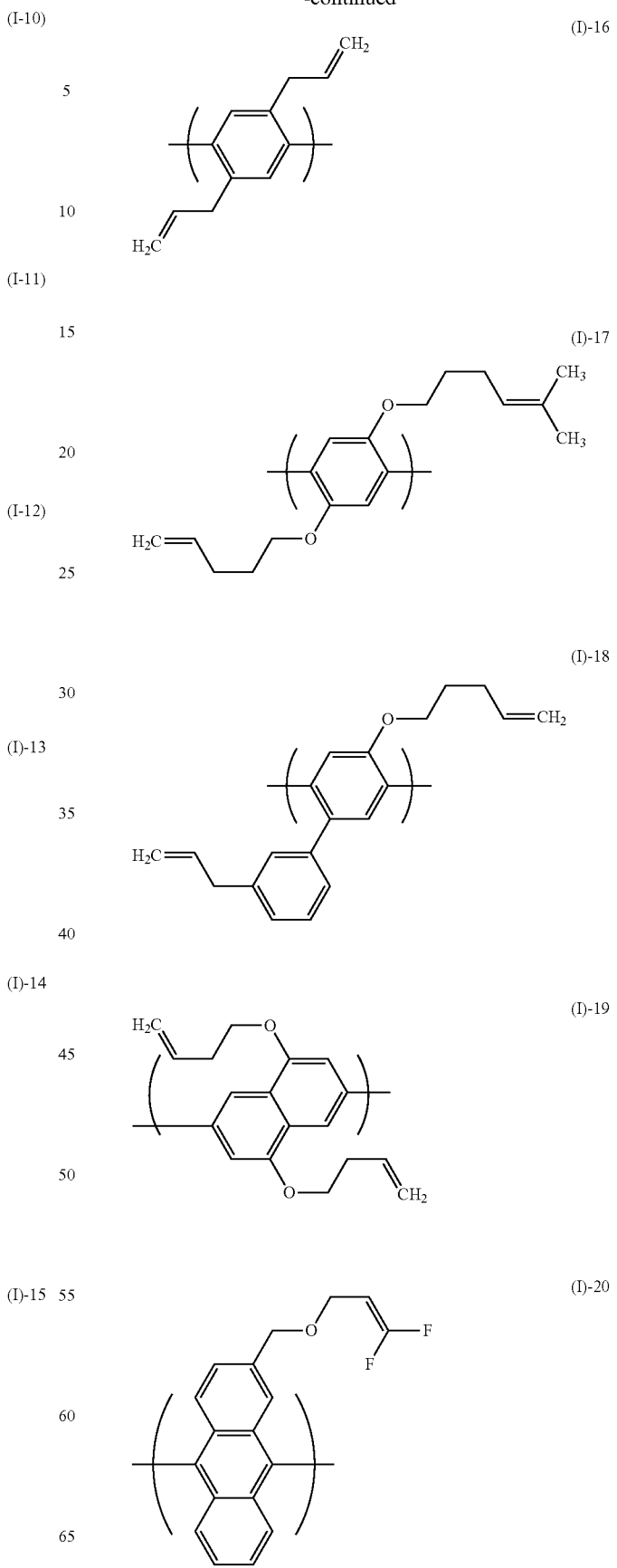

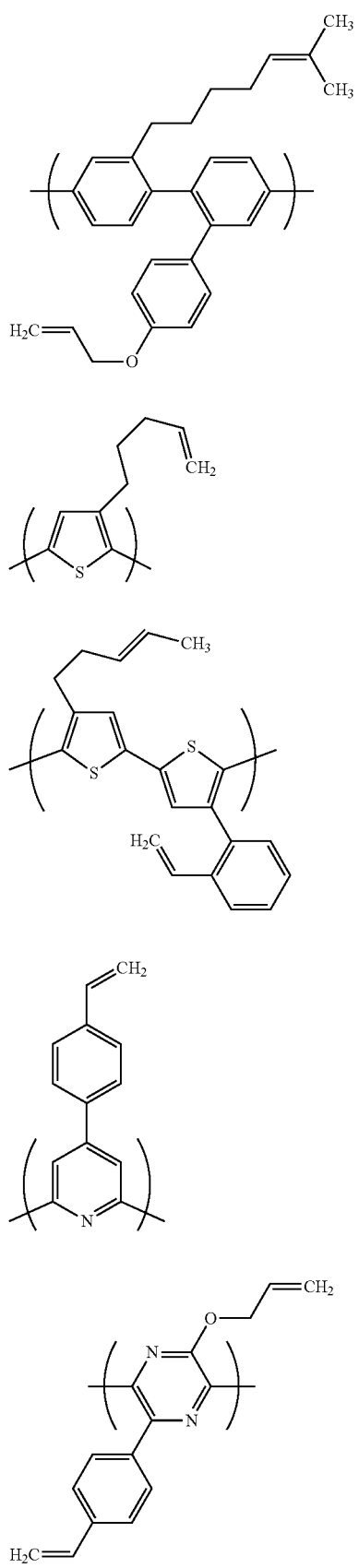
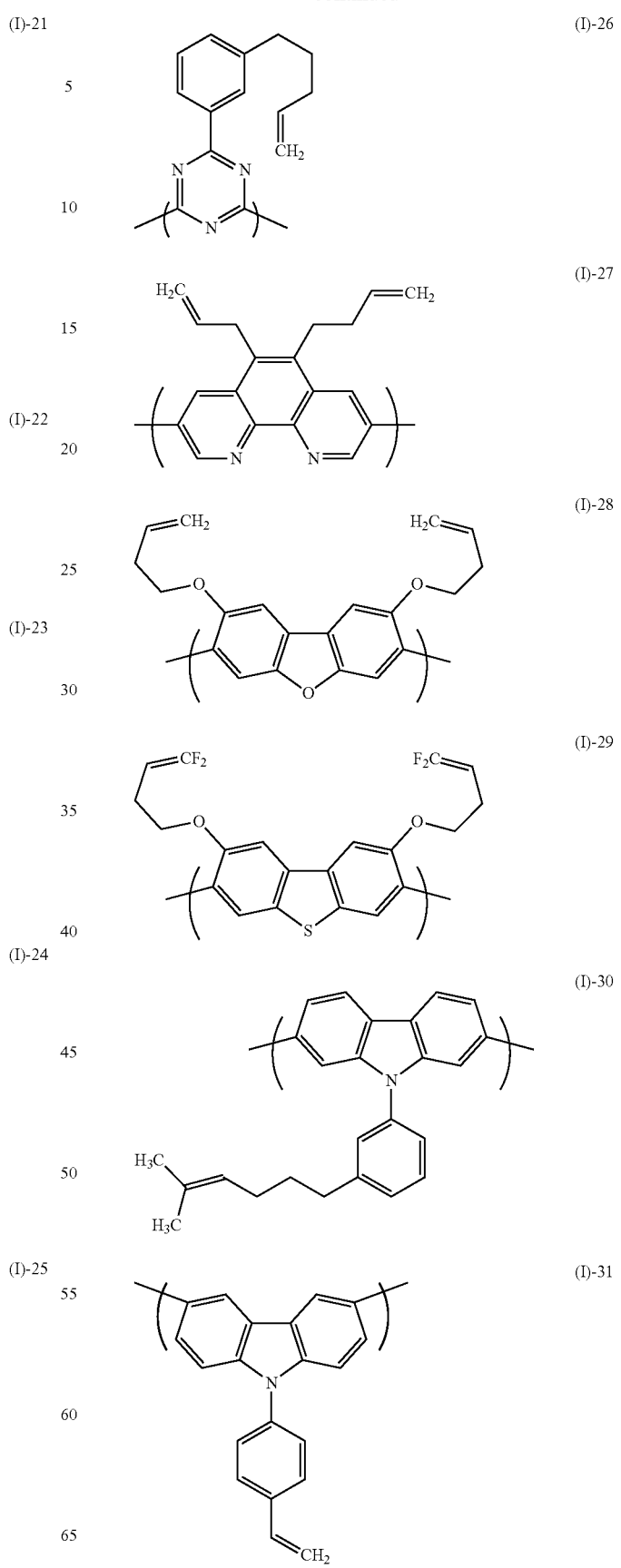

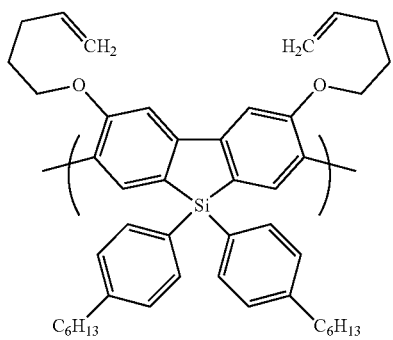
(I)-32

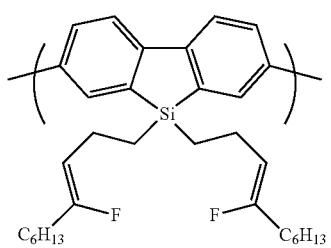
(I)-33

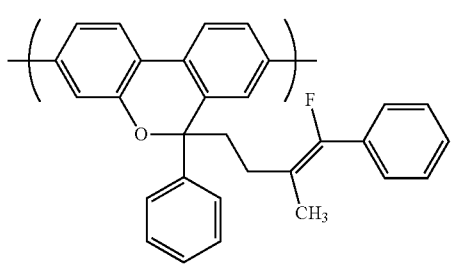
(I)-34

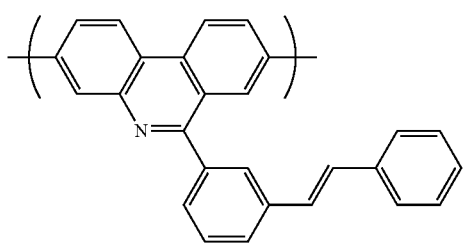
(I)-35

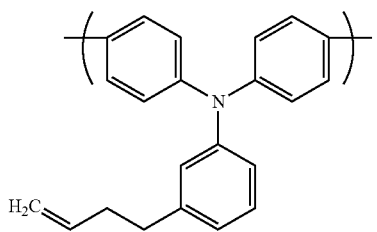
(I)-36

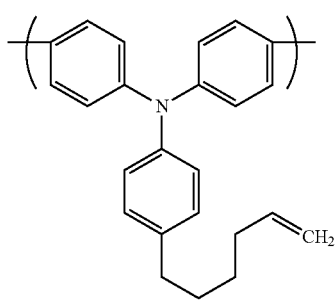
(I)-37

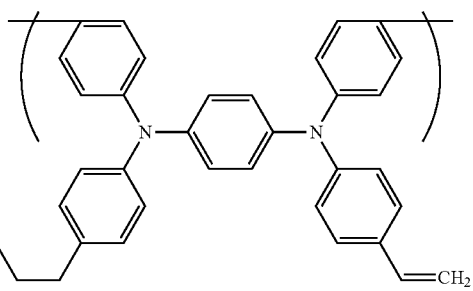
(I)-38

The repeating unit represented by the above formula (I) is, in view of charge transport property of a polymer compound, preferably a repeating unit represented by the following formula (III):

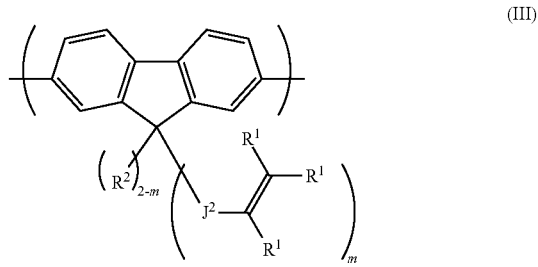
(III)

wherein $J^2$, $R^1$ and m are the same as defined above; and $R^2$ represents an alkyl group, an aryl group, an arylalkyl group or an arylalkoxy group.

In the above formula (III), the alkyl group, aryl group, arylalkyl group and arylalkoxy group represented by $R^2$ are the same as defined above.

—Repeating Unit Represented by the Formula (II)—

In the above formula (II), the fluorene-diyl group represented by $Ar^2$ is a divalent group having a fluorene skeleton with two bonds. Examples of the fluorene-diyl group include the groups represented by the following formulas ($Ar^2$-1) to ($Ar^2$-6).

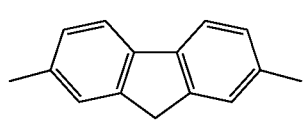
($Ar^2$-1)

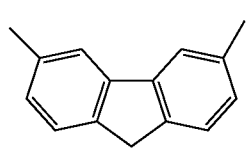
($Ar^2$-2)

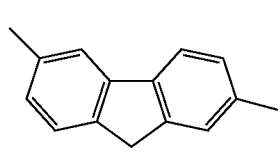
($Ar^2$-3)

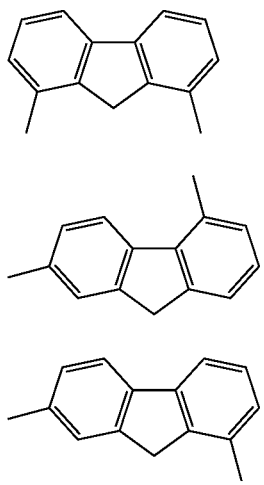

(Ar²-4)

(Ar²-5)

(Ar²-6)

Groups represented by the above formulas (Ar²-1) to (Ar²-6) may have a substituent other than the substituent represented by the above formula (IIa). As the substituent, the alkyl group, alkoxy group, alkylthio group, aryl group, aryloxy group, arylthio group, arylalkyl group, arylalkoxy group, arylalkylthio group, arylalkenyl group, arylalkynyl group, amino group, substituted amino group, silyl group, substituted silyl group, halogen atom, acyl group, acyloxy group, imine residue, carbamoyl group, acid imide group, monovalent heterocyclic group, carboxyl group, substituted carboxyl group, cyano group and nitro group may be mentioned. In view of solubility into a solvent and durability of the polymer compound, an alkyl group, an alkoxy group, an aryl group, an arylalkyl group, an arylalkoxy group, a halogen atom or a cyano group are preferable, an alkyl group, an aryl group or an arylalkyl group are more preferable.

In the above formula (II), $J^3$ represents a direct bond, an alkylene group or a phenylene group; however, in view of availability of a raw-material compound, it is preferably a phenylene group. The alkylene group and phenylene group represented by $J^3$ are the same as defined above.

In the above formula (II), $J^4$ represents a direct bond, an alkylene group or a phenylene group; however, in view of harden ability of a polymer compound, a direct bond and an alkylene group are preferable, an alkylene group is more preferable and a linear alkylene group is particularly preferable. The alkylene group and phenylene group represented by $J^4$ are the same as defined above.

In the above formula (I), k is an integer of 0 to 3; however, in view of easiness of synthesizing a monomer serving as a raw material, it is preferably 0 to 1 and particularly preferably 0.

In the above formula (I), l is 0 or 1; however, in view of easiness of synthesizing a monomer serving as a raw material, it is preferably 0.

In the above formula (II), n is 1 or 2; however, in view of easiness of synthesizing a monomer serving as a raw material, it is preferably 2.

Examples of the repeating unit represented by the above formula (II) include the repeating units represented by the following formulas (II-1) to (II-8).

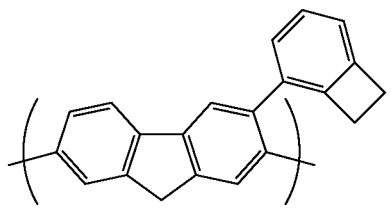

(II-1)

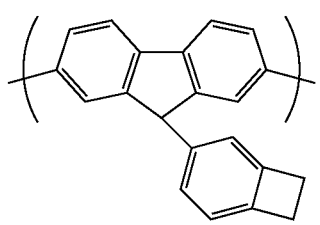

(II-2)

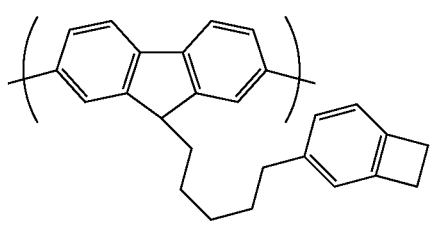

(II-3)

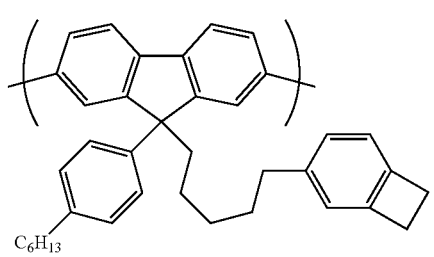

(II-4)

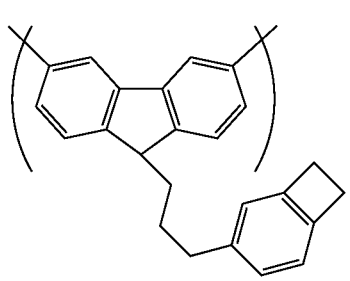

(II-5)

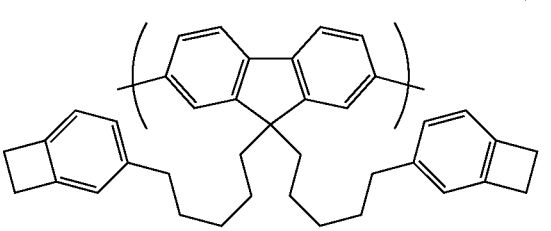

(II-6)

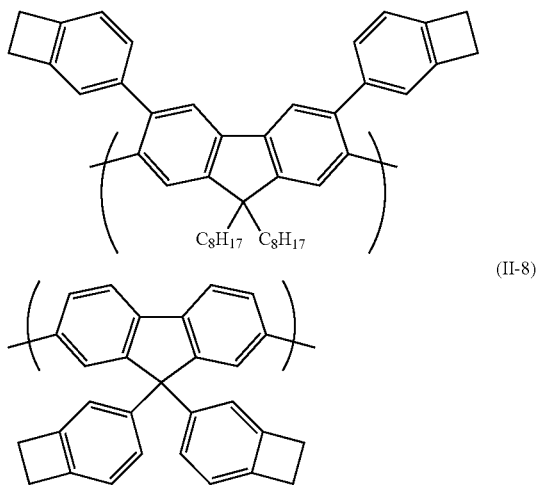

The repeating unit represented by the above formula (II) is, in view of charge transport property of a polymer compound, preferably a repeating unit represented by the following formula (IV):

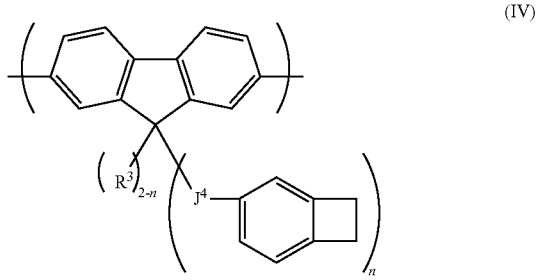

wherein $J^4$ and n are the same as defined above; $R^3$ represents an alkyl group, an aryl group, an arylalkyl group or an arylalkoxy group).

In the above formula (IV), the alkyl group, aryl group, arylalkyl group and arylalkoxy group represented by $R^3$ are the same as defined above.

—Ratio of Repeating Unit—

In the polymer compound of the present invention, the uppermost molar ratio of the repeating unit represented by the above formula (I) relative to the total repeating units constituting the polymer compound is, in view of stability of the device, usually 0.5, preferably 0.3, and particularly preferably 0.2. The lowermost molar ratio is, in view of crosslinking performance, usually 0.01, preferably 0.02, further preferably 0.03, and particularly preferably 0.05.

In the polymer compound of the present invention, the uppermost molar ratio of the repeating unit represented by the above formula (II) relative to the total repeating units constituting the polymer compound is, in view of stability of the device, usually 0.5, preferably 0.3, further preferably 0.2, and particularly preferably 0.1. The lowermost molar ratio is, in view of crosslinking performance, usually 0.01, preferably 0.02, and particularly preferably 0.03.

In the polymer compound of the present invention, the ratio (molar ratio) of the repeating unit represented by the above formula (I) to the repeating unit (1 mole) represented by the above formula (II) is usually, 1 to 30 moles, preferably 1 to 20 moles, more preferably 1 to 10 moles, further preferably 1 to 5 moles, and particularly preferably 1 to 4 moles.

—Other Repeating Units—

The polymer compound of the present invention may have repeating units containing a crosslinking group other than the repeating units represented by the above formulas (I) and (II), in view of crosslinking performance of a polymer compound.

The crosslinking group refers to a substituent causing a crosslinking reaction by a stimulus such as heat or light.

Examples of the crosslinking group include an oxiranyl group, an oxetanyl group, a cinnamoyl group, a dienophile group and an alkynyl group.

In view of charge transport property of the polymer compound, the polymer compound of the present invention preferably contains, in addition to the repeating unit represented by the above formula (I) and the repeating unit represented by the above formula (II), a repeating unit represented by the following formula (A):

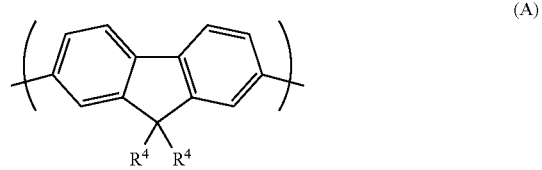

wherein $R^4$ represents an alkyl group, an aryl group, an arylalkyl group or an arylalkoxy group; and two $R^4$ may be the same or different.

In the above formula (A), the alkyl group, aryl group, arylalkyl group and arylalkoxy group represented by $R^4$ are the same as defined above.

The polymer compound of the present invention may preferably have, in view of hole transport property of the polymer compound, in addition to the repeating unit represented by the above formula (I) and the repeating unit represented by the above formula (II), one or more repeating unit selected from the group consisting of repeating units represented by the following formula (B) and repeating units represented by the following formula (C).

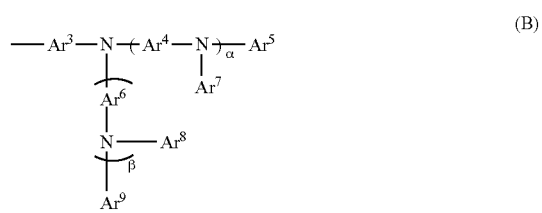

wherein $Ar^3$, $Ar^4$, $Ar^5$ and $Ar^6$ each independently represent an arylene group or a divalent heterocyclic group; $Ar^7$, $Ar^8$ and $Ar^9$ each independently represent an aryl group or a monovalent heterocyclic group; α and β each independently represent 0 or 1; and $Ar^3$, $Ar^4$, $Ar^5$, $Ar^6$, $Ar^7$, $Ar^8$ and $Ar^9$ may have a substituent.

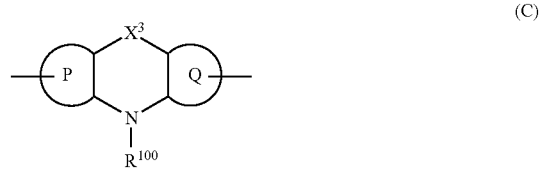

wherein ring P and ring Q each independently represent an aromatic hydrocarbon ring; $X^3$ represents a single bond, an oxygen atom and a sulfur atom; and $R^{100}$ represents an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an acid imide group, a monovalent heterocyclic group, a carboxyl group, a substituted carboxyl group, a cyano group or a nitro group.

In the above formula (B), the arylene group, divalent heterocyclic group, aryl group and monovalent heterocyclic group are the same as defined above.

Examples of the substituent that $Ar^3$, $Ar^4$, $Ar^5$, $Ar^6$, $Ar^7$, $Ar^8$ and $Ar^9$ may have include an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an acid imide group, a monovalent heterocyclic group, a carboxyl group, a substituted carboxyl group, a cyano group and a nitro group.

The alkyl group, alkoxy group, alkylthio group, aryl group, aryloxy group, arylthio group, arylalkyl group, arylalkoxy group, arylalkylthio group, arylalkenyl group, arylalkynyl group, amino group, substituted amino group, silyl group, substituted silyl group, halogen atom, acyl group, acyloxy group, imine residue, carbamoyl group, acid imide group, monovalent heterocyclic group, carboxyl group, substituted carboxyl group, cyano group and nitro group are the same as defined above.

In the above formula (C), the aromatic hydrocarbon ring represents an aromatic hydrocarbon ring obtained by removing two bonds from an arylene group as mentioned above.

In the above formula (C), the alkyl group, alkoxy group, alkylthio group, aryl group, aryloxy group, arylthio group, arylalkyl group, arylalkoxy group, arylalkylthio group, arylalkenyl group, arylalkynyl group, amino group, substituted amino group, silyl group, substituted silyl group, halogen atom, acyl group, acyloxy group, imine residue, carbamoyl group, acid imide group, monovalent heterocyclic group, carboxyl group, substituted carboxyl group, cyano group and nitro group are the same as defined above.

The repeating unit represented by the above formula (B) is, in view of hole transport property, preferably a repeating unit represented by the following formula (B)-1 or (B)-2.

(B)-1 wherein $R^5$ represents a hydrogen atom, an alkyl group or an alkoxy group; and three $R^5$ may be the same or different.

(B)-2 wherein $R^6$ represents a hydrogen atom, an alkyl group or an alkoxy group; and six $R^6$ may be the same or different.

In the above formula (B)-1, the alkyl group and alkoxy group represented by $R^5$ are the same as defined above.

In the above formula (B)-2, the alkyl group and alkoxy group represented by $R^6$ are the same as defined above.

The repeating unit represented by the above formula (C) is, in view of hole transport property, preferably a repeating unit represented by the following formula (C)-1.

(C)-1 wherein $R^7$ is an alkyl group, an aryl group, an arylalkyl group or an arylalkoxy group.

In the above formula (C)-1, the alkyl group, aryl group, arylalkyl group and arylalkoxy group represented by $R^7$ are the same as defined above.

The polymer compound of the present invention preferably contains at least one of the repeating units represented by the above formulas (B) and (C) in addition to the repeating unit represented by the above formula (A), in view of luminous efficiency.

Furthermore, the polymer compound of the present invention may preferably contain the repeating units represented by the following formulas (E) to (H) in addition to at least one of the repeating units represented by the above formulas (A) to (C), the repeating unit represented by the above formula (I) and the repeating unit represented by the above formula (II), in view of the charge transport property of a polymer compound.

(E)

wherein $R^8$ represents an alkyl group, an aryl group, an arylalkyl group or an arylalkoxy group; and two $R^8$ may be the same or different.

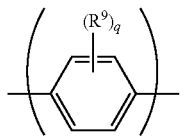
(F)

wherein $R^9$ represents an alkyl group, an alkoxy group, an aryl group, an arylalkyl group or an arylalkoxy group; q represents an integer of 0 to 4; and a plurality of $R^9$ may be the same or different.

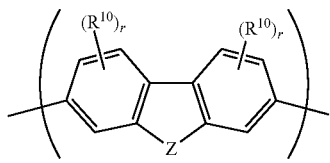
(G)

wherein $R^{10}$ represents an alkyl group, an alkoxy group, an aryl group, an arylalkyl group or an arylalkoxy group; Z represents an oxygen atom or a sulfur atom; r is an integer of 0 to 3; and a plurality of $R^{10}$ may be the same or different.

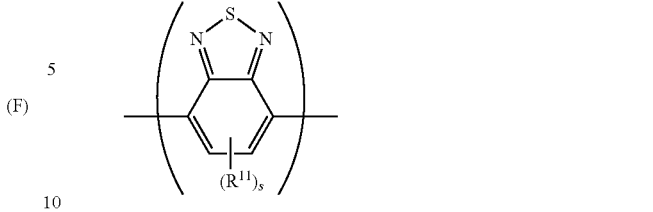
(H)

wherein $R^{11}$ represents an alkyl group, an alkoxy group, an aryl group, an arylalkyl group or an arylalkoxy group; s is an integer of 0 to 2; and a plurality of $R^{13}$ may be the same or different.

In the above formula (E), the alkyl group, aryl group, arylalkyl group and arylalkoxy group represented by $R^8$ are the same as defined above.

In the above formula (F), the alkyl group, alkoxy group, aryl group, arylalkyl group and arylalkoxy group represented by $R^9$ are the same as defined above.

In the above formula (G), the alkyl group, alkoxy group, aryl group, arylalkyl group and arylalkoxy group represented by $R^{10}$ are the same as defined above.

In the above formula (H), the alkyl group, alkoxy group, aryl group, arylalkyl group and arylalkoxy group represented by $R^{11}$ are the same as defined above.

—Specific Examples of Polymer Compound—

Specific examples of the polymer compound of the present invention include the polymer compounds represented by the following formulas. Note that, in the formulas, w, x, y and z each represent the composition ratio of a repeating unit.

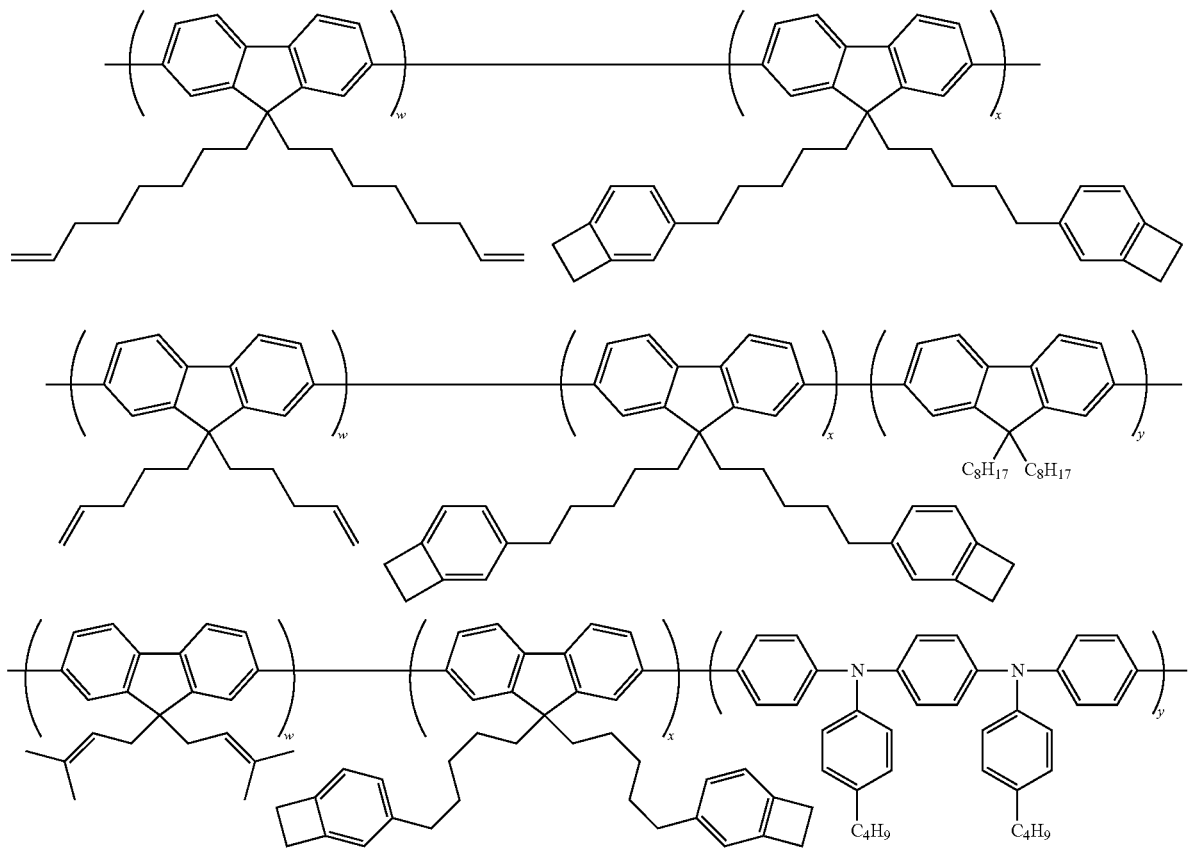

-continued
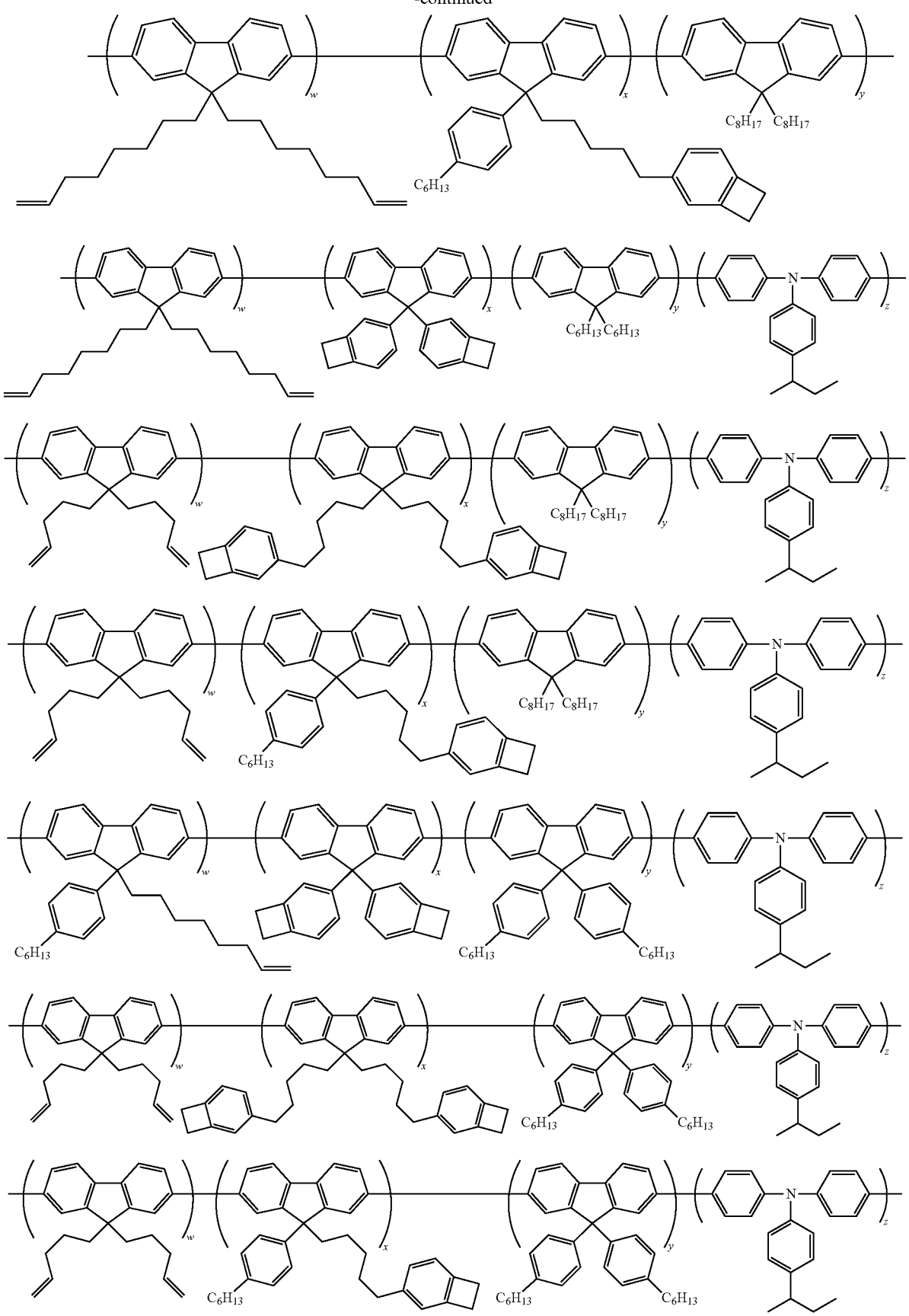

47 48
-continued
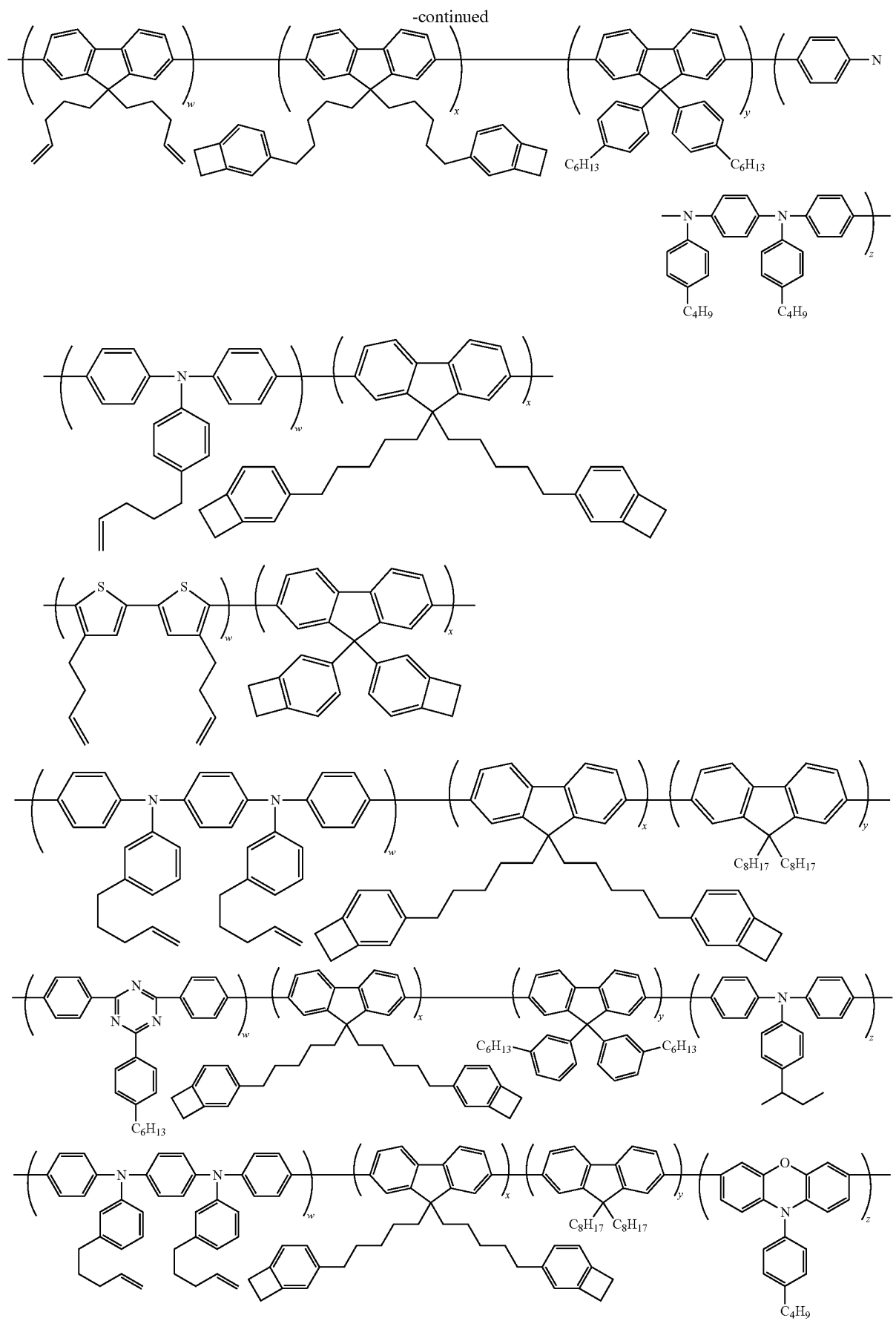

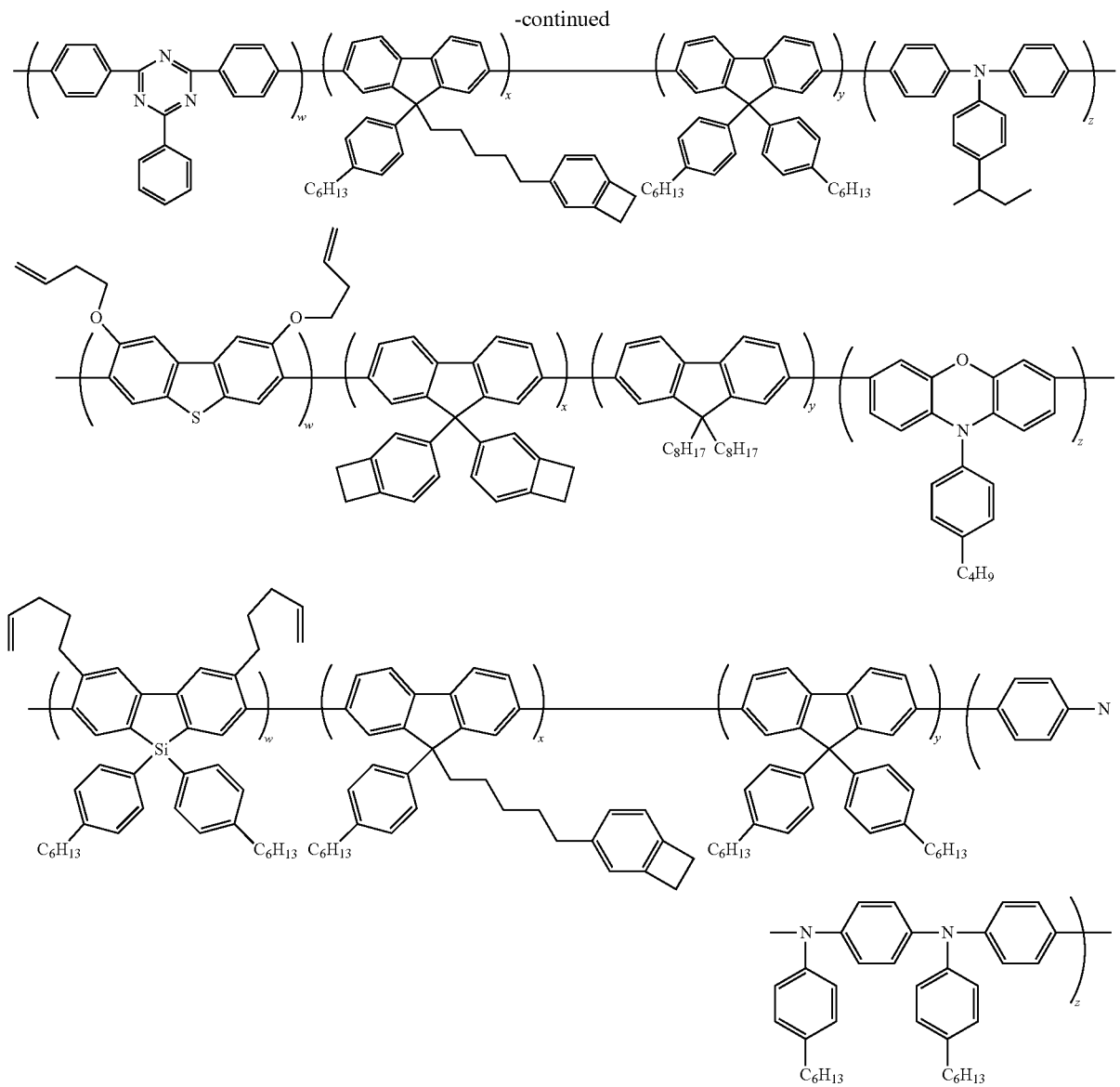

The polymer compound of the present invention, in view of the life property of the light-emitting device that is formed by using the compound, preferably has a polystyrene-equivalent number average molecular weight of $1\times10^3$ to $1\times10^8$, more preferably $1\times10^3$ to $1\times10^7$ and particularly preferably $1\times10^4$ to $1\times10^7$.

In the specification, a number average molecular weight and a weight average molecular weight were obtained by size exclusion chromatography (SEC) (trade name: LC-10Avp manufactured by Shimadzu Corporation) as a polystyrene-equivalent number average molecular weight and weight average molecular weight. Of the methods of SEC, chromatography using an organic solvent as a mobile phase is referred to as gel permeation chromatography (GPC). The polymer to be measured was dissolved in tetrahydrofuran at a concentration of about 0.5 wt % and 30 μL of the solution was loaded in GPC. As the mobile phase of GPC, tetrahydrofuran was used and allowed to flow at a rate of 0.6 mL/minute. As the column, two TSKgel SuperHM-H (manufactured by Tosoh Corporation) columns and a single TSKgel SuperH2000 (manufactured by Tosoh Corporation) column were connected in series. As the detector, a differential refractive index detector (trade name: RID-10A, manufactured by Shimadzu Corporation) was used. Measurement was performed at 40° C.

Furthermore, the polymer compound of the present invention may be any one of an alternating copolymer, a random copolymer, a block copolymer and a graft copolymer, or may be a polymer compound having an intermediate structure of them, for example, a random copolymer partially having a block copolymer. The polymer compound of the present invention is, in view of fluorescence or phosphorescence quantum yield, preferably a random copolymer partially having a block copolymer, a block copolymer and a graft copolymer rather than a complete random copolymer. In the polymer compound of the present invention, a dendrimer having a branch in the main chain and three or more terminal portions is included.

If a polymerizable group remains as it is as a terminal group of the polymer compound of the present invention, the luminescence property and life of the light-emitting device produced by using the compound may sometimes decrease. Because of this, the terminal group may be protected with a stable group. As the terminal group, a group having a conjugated bond continued to a conjugated structure of the main chain is preferable. For example, a group connected to an aryl group or a monovalent heterocyclic group via a carbon-carbon bond is mentioned. Alternatively, a substituent and the like described in JP 9-45478 A, Formula 10, may be mentioned.

<A Method for Producing the Polymer Compound>

Next, a method for producing the polymer compound of the present invention will be described. The polymer compound of the present invention may be manufactured in any method, for example, by condensation polymerization of a compound represented by the formula: $Y^1$-$A^1$-$Y^2$ and a compound represented by the formula: $Y^3$-$A^2$-$Y^4$. Note that in the above formula, $A^1$ represents a repeating unit represented by the above formula (I) and $A^2$ represents a repeating unit represented by the above formula (II). Furthermore, in the above formula, $Y^1$, $Y^2$, $Y^3$ and $Y^4$ each independently represent a polymerizable group.

Furthermore, when the polymer compound of the present invention has a repeating unit represented by the above formulas (A) to (H), the compound of the present invention can be produced by condensation polymerization of a compound represented by the formula: $Y^5$-$A^3$-$Y^6$ corresponding to the repeating unit. Furthermore, in the above formula, $Y^5$ and $Y^6$ each independently represent a polymerizable group.

Examples of the polymerizable group include a halogen atom, an alkylsulfonate group, an arylsulfonate group, an arylalkylsulfonate group, a boric acid ester residue, a sulfoniummethyl group, a phosphoniummethyl group, a phosphonatemethyl group, a monohalogenated methyl group, a boric acid residue (—B(OH)$_2$), a formyl group, a cyano group and a vinyl group.

Examples of the halogen atom serving as a polymerizable group include a fluorine atom, a chlorine atom, a bromine atom and an iodine atom.

Examples of the alkylsulfonate group serving as a polymerizable group include a methanesulfonate group, an ethanesulfonate group and a trifluoromethanesulfonate group.

Examples of the arylsulfonate group serving as a polymerizable group include a benzenesulfonate group and a p-toluenesulfonate group.

Examples of the arylalkylsulfonate group serving as a polymerizable group include a benzylsulfonate group.

Examples of the boric acid ester residue serving as a polymerizable group include groups represented by the following formulas:

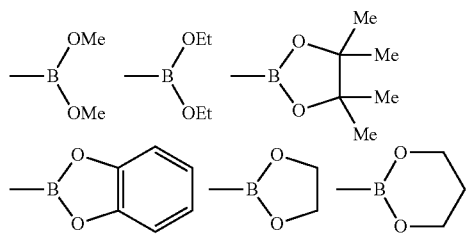

wherein Me represents a methyl group and Et represents an ethyl group.

Examples of the sulfoniummethyl group serving as a polymerizable group include groups represented by the following formulas:

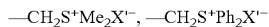
—CH$_2$S$^+$Me$_2$X'$^-$, —CH$_2$S$^+$Ph$_2$X'$^-$ wherein X' represents a halogen atom and Ph represents a phenyl group.

Examples of the phosphoniummethyl group serving as a polymerizable group include groups represented by the following formula:

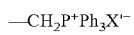
—CH$_2$P$^+$Ph$_3$X'$^-$ wherein X' represents a halogen atom.

Examples of the phosphonatemethyl group serving as a polymerizable group include groups represented by the following formula:

—CH$_2$PO(OR')$_2$ wherein R' represents an alkyl group, an aryl group or an arylalkyl group.

Examples of the monohalogenated methyl group serving as a polymerizable group include a methyl fluoride group, a methyl chloride group, a methyl bromide group and a methyl iodide group.

When a zero-valence nickel complex for the Yamamoto coupling reaction or the like is used, examples of the polymerizable group include a halogen atom, an alkylsulfonate group, an arylsulfonate group and an arylalkylsulfonate group. When a nickel catalyst or a palladium catalyst for the Suzuki coupling reaction or the like is used, examples thereof include an alkylsulfonate group, a halogen atom, a boric acid ester residue and boric acid residue.

The polymer compound of the present invention is produced by using a compound having a plurality of polymerizable groups serving as a monomer, if necessary, dissolved in an organic solvent, and using, for example, an alkali and an appropriate catalyst and at a temperature of not less than the melting point of the organic solvent and not more than the boiling point. Examples of the method that can be used include methods described in "Organic Reactions", Vol. 14, pages 270-490, John Wiley & Sons, Inc., 1965, "Organic Syntheses", Collective Volume VI, pages 407-411, John Wiley & Sons, Inc., 1988, Chem. Rev., Vol. 95, page 2457 (1995), J. Organomet. Chem., Vol. 576, page 147 (1999), Macromol. Chem., Macromol. Symp.), Vol. 12, page 229 (1987).

In the method for producing the polymer compound of the present invention, a known condensation reaction can be used depending upon the type of polymerizable group. Examples thereof include a method of polymerizing the corresponding monomer by the Suzuki coupling reaction, a method of polymerizing by the Grignard reaction, a method of polymerizing by an Ni(0) complex, a method of polymerizing by an oxidizing agent such as FeCl$_3$, a method of performing oxidative polymerization in an electrochemical manner and a method by decomposing an intermediate polymer having an appropriate leaving group.

Of these, a method of polymerizing by the Suzuki coupling reaction, a method of polymerizing by the Grignard reaction, and a method of polymerizing by a nickel zero-valence complex are preferable in view of structural control.

Of the methods for producing the polymer compound of the present invention, a production method using a polymerizable group selected from a halogen atom, an alkylsulfonate group, an arylsulfonate group and an arylalkylsulfonate group through and performed by a condensation polymerization in the presence of a nickel zero-valence complex is preferable.

Examples of a compound serving as a raw material for the polymer compound of the present invention include a dihalogenated compound, a bis(alkylsulfonate) compound, a bis(arylsulfonate) compound, a bis(arylalkyl sulfonate) compound, a halogen-alkylsulfonate compound, a halogen-arylsulfonate compound, a halogen-arylalkylsulfonate compound, an alkylsulfonate-arylsulfonate compound, an alkylsulfonate-arylalkylsulfonate compound and an arylsulfonate-arylalkylsulfonate compound. Furthermore, when a polymer compound controlled in sequence is produced, examples of the compound that may be preferably used include a halogen-alkylsulfonate compound, a halogen-arylsulfonate compound, a halogen-arylalkylsulfonate compound, an alkylsulfonate-arylsulfonate compound, an alkylsulfonate-arylalkylsulfonate compound and an arylsulfonate-arylalkylsulfonate compound.

A method for producing the polymer compound of the present invention is, in view of easiness of synthesizing the polymer compound, preferably a production method using a polymerizable group, which is selected from a halogen atom, an alkylsulfonate group, an arylsulfonate group, an arylalkylsulfonate group, a boric acid residue and a boric acid ester residue such that the ratio of the total mole number (J) of the halogen atom, alkylsulfonate group, arylsulfonate group and arylalkylsulfonate group contained in the whole raw-material compound and the total mole number (K) of boric acid residue and boric acid ester residue becomes substantially 1 (usually, K/J is 0.7 to 1.2), and performed by a condensation polymerization method using a nickel catalyst or a palladium catalyst.

Examples of a combination of compounds serving as raw materials (more specifically, a compound represented by the above formula: $Y^1$-$A^1$-$Y^2$ and a compound represented by the above formula: $Y^3$-$A^2$-$Y^4$) include a combination of a dihalogenated compound, a bis(alkylsulfonate) compound, a bis(arylsulfonate) compound or a bis(arylalkylsulfonate) compound and a diboric acid compound or diboric acid ester compound.

Furthermore, when a polymer compound controlled in sequence is produced, examples of the compound that may be preferably used include a halogen-boric acid compound, a halogen-boric acid ester compound, an alkylsulfonate-boric acid compound, an alkylsulfonate-boric acid ester compound, an arylsulfonate-boric acid compound, an arylsulfonate-boric acid ester compound, an arylalkylsulfonate-boric acid compound, an arylalkylsulfonate-boric acid compound and an arylalkylsulfonate-boric acid ester compound.

The organic solvent to be used in the condensation polymerization is preferably treated in advance sufficiently in a deoxidization process and a dehydration process in order to suppress a side reaction. However, this is not applied to the case where a reaction is performed in a two-phase system with water like the Suzuki coupling reaction.

Examples of the organic solvent to be used in the condensation polymerization include saturated hydrocarbons such as pentane, hexane, heptane, octane, cyclohexane; unsaturated hydrocarbons such as benzene, toluene, ethylbenzene and xylene; halogenated saturated hydrocarbons such as carbon tetrachloride, chloroform, dichloromethane, chlorobutane, bromobutane, chloropentane, bromopentane, chlorohexane, bromohexane, chlorocyclohexane and bromocyclohexane; halogenated unsaturated hydrocarbon such as chlorobenzene, dichlorobenzene and trichlorobenzene; alcohols such as methanol, ethanol, propanol, isopropanol, butanol and t-butyl alcohol; carboxylic acids such as formic acid, acetic acid and propionic acid; ethers such as dimethyl ether, diethyl ether, methyl-t-butyl ether, tetrahydrofuran, tetrahydropyrane and dioxane; amines such as trimethylamine, triethylamine, N,N,N',N'-tetramethylethylenediamine and pyridine; and amides such as N,N-dimethylformamide, N,N-dimethylacetamide, N,N-diethylacetamide and N-methylmorpholineoxide. Ethers are preferable and tetrahydrofuran and diethylether are particularly preferable. These organic solvents may be used alone or in combination with two or more types.

In the condensation polymerization, an alkali and a suitable catalyst may be appropriately added to facilitate the reaction. The alkali and catalyst are preferably dissolved sufficiently in the solvent to be used in the reaction. To add the alkali or catalyst, a solution of the alkali or catalyst is added slowly while a reaction solution is stirred under the atmosphere of an inert gas such as argon and nitrogen, or conversely, a reaction solution may be slowly added to a solution of the alkali or catalyst.

When the polymer compound of the present invention is used for producing a light-emitting device, the purity of the compound influences performance of the light-emitting device such as a luminescence property. Therefore, a raw material compound before subjected to polymerization is preferably purified by a method such as distillation, sublimation or recrystallization and thereafter subjected to polymerization. Further after the polymerization, purification such as purification by reprecipitation and fractionation by chromatography is preferably applied.

<Compound>

In producing the polymer compound of the present invention, a compound represented by the above formula (XII) is preferably used.

In the above formula (XII), the halogen atom, alkylsulfonate group, arylsulfonate group, arylalkylsulfonate group, boric acid residue and boric acid ester residue represented by X are the same as defined above; however, in view of easiness of synthesizing a compound, it is preferably a halogen atom and boric acid ester residue and preferably a halogen atom.

Furthermore, as the halogen atom, in view of easiness of undergoing condensation polymerization, a bromine atom and an iodine atom are preferable and a bromine atom is particularly preferable.

In the above formula (XII), o is an integer of 4 to 10; however, in view of availability of raw materials, it is preferably an integer of 4 to 8 and particularly preferably an integer of 5 to 8.

As the compound represented by the above formula (XII), the compounds represented by the following formulas are mentioned.

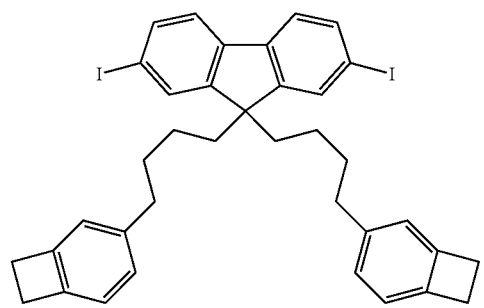

(XII-1)

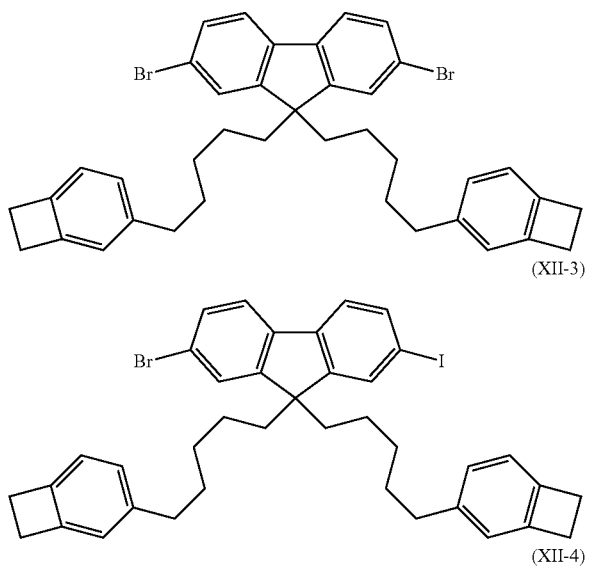

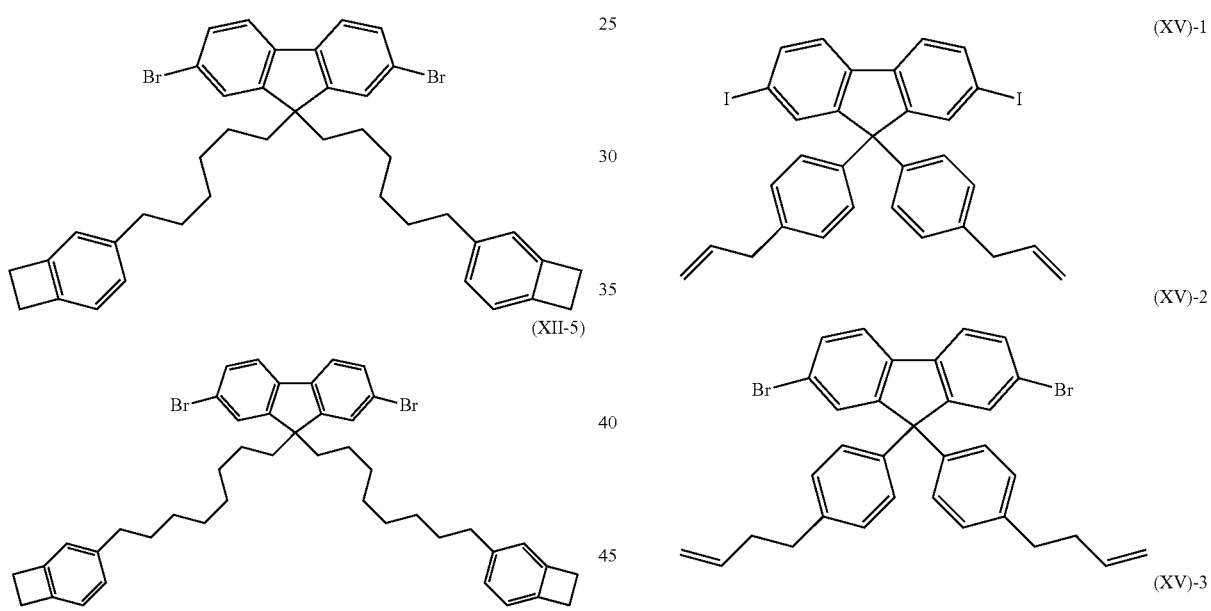

Furthermore, the compound represented by the above formula (XII) may be produced by any method. For example, the compound can be produced by a method including reacting a compound represented by the above formula (XIII) and a compound represented by the above formula (XIV) in a base.

As the base to be used in the above reaction, an inorganic base such as potassium carbonate, sodium carbonate, potassium hydroxide, and sodium hydroxide or an organic base such as triethylamine is added in an amount of 1 equivalent or more relative to the above formula (XIII) and preferably 1 to 20 equivalents and subjected to the reaction.

In the above reaction, usually, a solvent is used. Examples of the solvent include N,N-dimethylformamide, dimethylsulfoxide, toluene, dimethoxyethane and tetrahydrofuran.

The reaction temperature of the above reaction is usually 0° C. to the boiling point of the solvent and preferably 50 to 150° C. Furthermore, the reaction time of the above reaction is 0.5 to 100 hours.

Furthermore, in producing the polymer compound of the present invention, a compound represented by the above formula (XV) is preferably used.

In the above formula (XV), the halogen atom, alkylsulfonate group, arylsulfonate group, arylalkylsulfonate group, boric acid residue or boric acid ester residue represented by X is the same as defined above; however, in view of easiness of synthesizing a compound, it is preferably a halogen atom and a boric acid ester residue and preferably a halogen atom.

Furthermore, as the halogen atom, in view of easiness of undergoing condensation polymerization, a bromine atom and an iodine atom are preferable and a bromine atom is particularly preferable.

In the above formula (XII), z is an integer of 1 to 10; however, in view of availability of raw material, it is preferably an integer of 1 to 5 and particularly preferably an integer of 1 to 3.

Examples of the compound represented by the above formula (XV) include compounds represented by the following formulas:

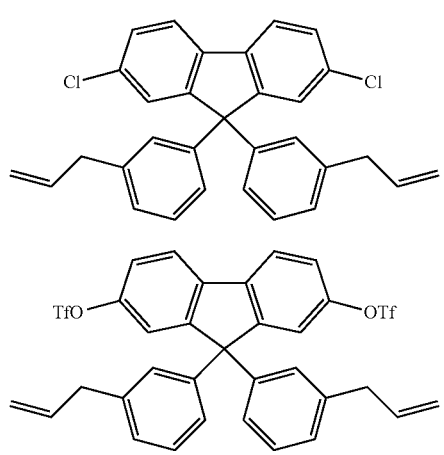

(XV)-5

(XV)-6 wherein OTf is a trifluoromethanesulfonate group.

Furthermore, the compound represented by the above formula (XV) may be produced in any method. For example, it can be produced by a method including reacting a compound represented by the above formula (XVI) in a base.

Examples of the base to be used in the above reaction include inorganic bases such as potassium carbonate, sodium carbonate, potassium hydroxide, sodium hydroxide and sodium tertiary butoxide; and organic bases such as triethylamine. The reaction is performed by adding not less than 1 equivalent of a base relative to the above formula (XVI) and preferably 1 to 20 equivalents of a base.

In the above reaction, usually, a solvent is used. Examples of the solvent include N,N-dimethylformamide, dimethylsulfoxide, toluene, dimethoxyethane and tetrahydrofuran.

The reaction temperature of the above reaction is usually −78° C. to the boiling point of a solvent and preferably −20° C. to 100° C. Furthermore, the reaction time of the above reaction is 0.5 to 100 hours.

<Use Application>

The polymer compound of the present invention is not only useful as a light-emitting material but also useful as a film, an organic semiconductor material, an organic transistor, an optical material, an organic photoelectric transducer or a conductive material by doping.

<Composition>

The composition of the present invention is a composition comprising the polymer compound of the present invention. For example, a composition containing at least one selected from the group consisting of a hole transport material, an electron transport material and a light-emitting material, and a polymer compound as mentioned above, is mentioned.

Furthermore, the composition of the present invention can be rendered also to be a liquid composition further by adding a solvent thereto. More specifically, the liquid composition of the present invention is a liquid composition comprising a polymer compound as mentioned above and a solvent.

The liquid composition of the present invention is useful for producing a light-emitting device such as a light-emitting device and an organic transistor. In the specification, "the liquid composition" refers to a composition which is present as a liquid state when a device is produced, and typically refers to a composition present in a liquid state at normal pressure (more specifically, 1 atm) and at 25° C. Furthermore, the liquid composition is sometimes generally called as ink, an ink composition and solution, etc. Hereinafter, the composition of the present invention and the liquid composition of the present invention are collectively referred to as "the liquid composition".

The liquid composition of the present invention may contain, other than a polymer compound as mentioned above, a low molecular light-emitting material, a hole transport material, an electron transport material, a stabilizer, additives for controlling viscosity and/or surface tension and an antioxidant, etc. These optional components each may be used alone or in combination with two or more types.

Examples of the low molecular light-emitting material include a naphthalene derivative, anthracene, an anthracene derivative, perylene, a perylene derivative, a polymethine-based pigment, a xanthene-based pigment, a coumarin-based pigment, a cyanine-based pigment, a metal complex containing a metal complex of an 8-hydroxyquinoline as a ligand, a metal complex containing a metal complex of an 8-hydroxyquinoline derivative as a ligand, other fluorescent metal complexes, an aromatic amine, tetraphenylcyclopentadiene, a tetraphenylcyclopentadiene derivative, tetraphenylcyclobutadiene, a tetraphenylcyclobutadiene derivative, fluorescent materials such as stilbene-, a silicon-containing aromatic-, oxazole-, furoxan-, thiazole-, tetraarylmethane-, thiadiazole-, pyrazole-, metacyclophane- and acetylene-based low molecular compounds. In addition, materials described in JP 57-51781 A and JP 59-194393 A etc. are included.

Examples of the hole transport material include polyvinyl carbazole and a derivative thereof, polysilane and a derivative thereof, a polysiloxane derivative having an aromatic amine in the side chain or main chain, a pyrazoline derivative, an arylamine derivative, a stilbene derivative, a triphenyldiamine derivative, polyaniline and a derivative thereof, polythiophene and a derivative thereof, polypyrrole and a derivative thereof, poly(p-phenylenevinylene) and a derivative thereof, and poly(2,5-thienylenevinylene) and a derivative thereof.

Examples of the electron transport material include, an oxadiazole derivative, anthraquinodimethane and a derivative thereof, benzoquinone and a derivative thereof, naphthoquinone and a derivative thereof, anthraquinone and a derivative thereof, tetracyanoanthraquinodimethane and a derivative thereof, a fluorenone derivative, diphenyldicyanoethylene and a derivative thereof, a diphenoquinone derivative, metal complexes of 8-hydroxyquinoline and a derivative thereof, polyquinoline and a derivative thereof, polyquinoxaline and a derivative thereof, and polyfluorene and a derivative thereof.

Examples of the stabilizer include a phenolic antioxidant and a phosphoric antioxidant.

As additives for controlling viscosity and/or surface tension, a high molecular-weight compound (thickening agent) and a poor solvent for increasing viscosity, a low molecular-weight compound for decreasing viscosity and a surfactant for decreasing surface tension etc. may be used in appropriate combination.

As the high molecular-weight compound, any high molecular-weight compound may be used as long as it does not inhibit light emission and charge transport, and it is usually a soluble compound in the solvent for a liquid composition. As the high molecular-weight compound, a high molecular weight polystyrene and a high molecular weight polymethylmethacrylate, etc. can be used. The polystyrene-equivalent weight average molecular weight of the high molecular-weight compound is preferably 500,000 or more and more preferably 1,000,000 or more. Furthermore, a poor solvent can be used as a thickening agent.

As the antioxidant, any antioxidant may be used as long as it does not inhibit light emission and charge transport, and if a composition contains a solvent, the antioxidant soluble in the solvent is usually used. Examples of the antioxidant include a phenolic antioxidant and a phosphoric antioxidant. Storage stability of the polymer compound and the solvent can be improved by use of the antioxidant.

When the liquid composition of the present invention contains a hole transport material, the ratio of the hole transport material in the liquid composition is usually 1 to 80 wt % and preferably 5 to 60 wt %. Furthermore, when the liquid composition of the present invention contains an electron transport material, the ratio of the electron transport material in the liquid composition is usually 1 to 80 wt % and preferably 5 to 60 wt %.

When a film is formed by using the liquid composition in producing a light-emitting device, after the liquid composition is applied, all that should be done is just removing a solvent by drying. In addition, when a charge transport material and a light-emitting material are added, the same procedure can be applied. Therefore, the liquid composition is extremely favorable in view of production. Note that drying may be performed in a warm state of about 50 to 150° C. or under reduced pressure of about $10^{-3}$ Pa.

In forming a film using the liquid composition, a coating method can be used such as a spin coating method, a casting method, a microgravure coating method, a gravure coating method, a bar coating method, a roll coating method, a wire bar coating method, a dip coating method, a slit coating method, a cap coating method, a capillary coating method, a spray coating method, a screen printing method, a flexo printing method, an offset printing method, an inkjet printing method and a nozzle coating method.

The ratio of a solvent in the liquid composition is usually 1 to 99.9 wt % relative to the total weight of the liquid composition, preferably 60 to 99.9 wt % and more preferably, 90 to 99.8 wt %. The viscosity of the liquid composition, which varies depending upon the printing method, is preferably 0.5 to 500 mPa·s at 25° C. In the case where the liquid composition passes through an ejection apparatus as in the case of inkjet printing method etc., viscosity is preferably 0.5 to 20 mPa·s at 25° C. to prevent clogging during ejection and bending of sprayed liquid composition.

As the solvent contained in the liquid composition, a solvent capable of dissolving or dispersing components of the liquid composition except the solvent is preferable. Examples of the solvent include chlorine solvents such as chloroform, methylene chloride, 1,2-dichloroethane, 1,1,2-trichloroethane, chlorobenzene and o-dichloro benzene; ether solvents such as tetrahydrofuran and dioxane; aromatic hydrocarbon solvents such as toluene, xylene, trimethylbenzene and mesitylene; aliphatic hydrocarbon solvents such as cyclohexane, methylcyclohexane, n-pentane, n-hexane, n-heptane, n-octane, n-nonane and n-decane; ketone solvents such as acetone, methylethylketone and cyclohexanone; ester solvents such as ethyl acetate, butyl acetate, methyl benzoate and ethyl cellosolve acetate; polyhydric alcohols and a derivative thereof such as ethylene glycol, ethylene glycol monobutyl ether, ethylene glycol monoethylether, ethylene glycol monomethylether, dimethoxyethane, propylene glycol, diethoxymethane, triethylene glycol monoethylether, glycerin and 1,2-hexanediol; alcohol solvents such as methanol, ethanol, propanol, isopropanol and cyclohexanole; sulfoxide solvents such as dimethylsulfoxide; and amide solvents such as N-methyl-2-pyrrolidone and N,N-dimethylformamide. Furthermore, these solvents may be used alone or in combination of more than one types. Of the solvents, one or more organic solvents having a structure having at least one benzene ring and having a melting point of 0° C. or less and a boiling point of 100° C. or more is preferably contained in view of viscosity and film forming property etc. As the type of solvent, in view of solubility of the components of the liquid composition except the solvent in an organic solvent, uniformity of the film formed and viscosity property, etc., an aromatic hydrocarbon solvent, an aliphatic hydrocarbon solvent, an ester solvent and a ketone solvent are preferable. Preferable examples thereof include toluene, xylene, ethylbenzene, diethylbenzene, trimethylbenzene, mesitylene, n-propylbenzene, isopropylbenzene, n-butylbenzene, isobutylbenzene, s-butylbenzene, anisole, ethoxybenzene, 1-methylnaphthalene, cyclohexane, cyclohexanone, cyclohexyl benzene, bicyclohexyl, cyclohexenylcyclohexanone, n-heptylcyclohexane, n-hexylcyclohexane, methylbenzoate, 2-propylcyclohexanone, 2-heptanone, 3-heptanone, 4-heptanone, 2-octanone, 2-nonanone, 2-decanone and dicyclohexyl ketone. More preferably, at least one of the solvents including xylene, anisole, mesitylene, cyclohexylbenzene and bicyclohexylmethylbenzoate, is contained.

The number of types of solvents contained in the liquid composition, in view of film forming property and device characteristic, is preferably 2 or more, more preferably 2 to 3 and particularly preferably 2.

When 2 types of solvents are contained in the liquid composition, one of the solvents may be in a solid state at 25° C. In view of film forming property, it is preferable that one of the solvents has a boiling point of 180° C. or more and the other solvent has a boiling point of less than 180° C. It is more preferable that one of the solvents has a boiling point of 200° C. or more and the other solvent has a boiling point of less than 180° C. Furthermore, in view of viscosity, 0.2 wt % or more of the components of the liquid composition from which a solvent is removed is preferably dissolved in the solvent at 60° C. In one of the two types of solvents, 0.2 wt % or more of the components of the liquid composition from which a solvent is removed is preferably dissolved at 25° C.

When three types of solvents are contained in the liquid composition, one to two types of solvents may be in a state of solid at 25° C. In view of film forming property, it is preferable that at least one of the three types of solvents has a boiling point of 180° C. or more and at least one of the solvents has a boiling point of less than 180° C. It is more preferable that at least one of the three types of solvents has a boiling point of 200° C. or more and 300° C. or less and at least one of the solvents has a boiling point of less than 180° C. In view of viscosity, in two types of the three types of solvents, 0.2 wt % or more of the components of the liquid composition from which a solvent is removed is preferably dissolved at 60° C. In one of the three types of solvents, 0.2 wt % or more of the components of the liquid composition from which a solvent is removed is preferably dissolved at 25° C.

When two or more types of solvents are contained in the liquid composition, in view of viscosity and film forming property, the content of the solvent having the highest boiling point is preferably 40 to 90 wt % of the total solvents contained in the liquid composition and more preferably 50 to 90 wt % and further preferably 65 to 85 wt %.

<Film>

A film of the present invention will be described. The film is formed of a polymer compound as mentioned above. As the type of film, a luminous film, a conductive film and an organic semiconductor film, etc. are exemplified. Furthermore, a film according to a second aspect of the present invention is formed by crosslinking of the polymer compound. The film is usually hardened by crosslinking caused by an external stimulus such as heat or light.

The heat for hardening a film is not particularly limited; however, it generally falls within the range of room temperature to 300° C. The upper limit thereof is, in view of easiness of forming a film, preferably 250° C., further preferably 190° C. and most preferably 170° C. Furthermore, the lower limit is, in view of stability of a film at room temperature, preferably 50° C., further preferably 70° C. and most preferably 100° C.

The light for hardening a film is not particularly limited; however, generally UV light, near ultra violet light and visible light are used, and UV light and near ultra violet light are preferable.

The luminous film, in view of brightness of a device and emission voltage etc., preferably has, an emission quantum yield of 50% or more, more preferably 60% or more and further preferably 70% or more.

A conductive film preferably has a surface resistance of 1 $K\Omega/\square$ or less. The electric conductivity of the film can be improved by doping a Lewis acid and an ionic compound, etc. thereto. The surface resistance is more preferably $100\Omega/\square$ or less and further preferably, $10\Omega/\square$ or less.

In an organic semiconductor film, a larger one of an electron mobility and a hole mobility is preferably $10^{-5}$ cm$^2$/V/second or more, more preferably $10^{-3}$ cm$^2$/V/second or more and further preferably $10^{-1}$ cm$^2$/V/second or more. Furthermore, an organic transistor can be produced by using an organic semiconductor film. Specifically, an organic transistor can be obtained by forming an organic semiconductor film on an Si substrate having an insulating film such as SiO$_2$ and a gate electrode formed thereon, and forming a source electrode and a drain electrode of Au, etc.

<Organic Transistor>

The organic transistor of the present invention is an organic transistor comprising a polymer compound as mentioned above. Hereinafter, an embodiment of the organic transistor, that is, a polymer field effect transistor, will be described.

The polymer compound of the present invention can be suitably used as a material for polymer field effect transistor, in particular, as a material for an active layer. As the structure of the polymer field effect transistor, it is usually satisfactory if a source electrode and a drain electrode are provided in contact with an active layer formed of a polymer and a gate electrode is provided so as to sandwich an insulating layer in contact with the active layer.

The polymer field effect transistor is usually formed on a supporting substrate. As the supporting substrate, a glass substrate, a flexible film substrate as well as a plastic substrate can be used.

A polymer field effect transistor can be produced by a known method, for example, a method described in JP 5-110069 A.

When an active layer is formed, use of a polymer compound soluble in an organic solvent is favorable and preferable in view of production. In forming a film from a solution prepared by dissolving a polymer compound soluble in an organic solvent in a solvent, a spin coating method, a casting method, a microgravure coating method, a gravure coating method, a bar coating method, a roll coating method, a wire bar coating method, a dip coating method, a slit coating method, a cap coating method, a capillary coating method, a spray coating method, a screen printing method, a flexo printing method, an offset printing method, an inkjet printing method and a nozzle coating method can be used.

After the polymer field effect transistor is produced and preferably encapsulated to form an encapsulated polymer field effect transistor. By virtue of this, the polymer field effect transistor can be blocked from the air and suppressed from deterioration of characteristics thereof.

As the encapsulating method, e.g., a method of covering with a UV rays (UV) curable resin, a thermosetting resin and an inorganic SiONx film, etc. and a method of joining glass plates and films with a UV rays (UV) curable resin or a thermosetting resin are mentioned. To effectively block a polymer field effect transistor from the air, it is preferred to perform steps from production thereof to encapsulation without being exposed to the air (for example, in a dry nitrogen atmosphere or in vacuum).

<Organic Photoelectric Transducer>

An organic photoelectric transducer of the present invention (for example, solar battery etc.) is an organic photoelectric transducer comprising the aforementioned polymer compound.

The polymer compound of the present invention can be preferably used as a material for an organic photoelectric transducer, in particular, as an organic semiconductor layer of a Schottky barrier type device using the interface between an organic semiconductor and a metal, and furthermore, as an organic semiconductor layer of a pn-heterojunction type device using the interface between an organic semiconductor and an inorganic semiconductor or the interface between organic semiconductors.

Furthermore, the compound of the present invention can be preferably used as an electron donating polymer and an electron receptor polymer in a bulk heterojunction device increased in donor/acceptor contact area, furthermore, an organic photoelectric transducer using a polymer/low molecular complex system, for example, as an electron donating conjugated polymer (diffusion support) of a bulk heterojunction organic photoelectric transducer having a fullerene derivative dispersed therein as an electron receptor.

As a structure of an organic photoelectric transducer, for example, in a pn-heterojunction device, it is satisfactory if a p-type semiconductor layer is formed on ITO, further an n-type semiconductor layer is laminated thereon, and an ohm electrode is provided thereon.

The organic photoelectric transducer is usually formed on a supporting substrate. As the supporting substrate, a glass substrate, a flexible film substrate as well as a plastic substrate can be used.

An organic photoelectric transducer can be produced by a known method, for example, a method described in Synth. Met., 102, 982 (1999) and a method described in Science, 270, 1789 (1995).

<Light-Emitting Device>

Next, a light-emitting device of the present invention will be described.

The light-emitting device of the present invention is a light-emitting device having electrodes comprising an anode and a cathode, a light-emitting layer provided between the electrodes and comprising the polymer compound of the present invention and/or a charge transport layer provided between the electrodes and comprising the polymer compound of the present invention. Furthermore, a light-emitting device according to a second aspect of the present invention is a light-emitting device having electrodes comprising an anode and a cathode, a light-emitting layer (usually, hardened by crosslinking) provided between the electrodes and formed by crosslinking the polymer compound of the present invention and/or a charge transport layer (usually, hardened by crosslinking) provided between the electrodes and formed by crosslinking the polymer compound of the present invention. Examples of the light-emitting device of the present invention include (1) an light-emitting device having an electron transport layer provided between a cathode and a light-emitting layer, (2) a light-emitting device having a hole transport layer provided between an anode and a light-emitting layer and (3) a light-emitting device having an electron transport layer provided between a cathode and a light-emitting layer and having a hole transport layer provided between an anode and the light-emitting layer.

More specifically, the following structures a) to d) are mentioned.

a) anode/light-emitting layer/cathode
b) anode/hole transport layer/light-emitting layer/cathode
c) anode/light-emitting layer/electron transport layer/cathode
d) anode/hole transport layer/light-emitting layer/electron transport layer/cathode (wherein symbol "/" indicates that individual layers are laminated in adjacent to each other. The same is applied in the following)

The light-emitting layer is a layer having a function of emitting light. The hole transport layer is a layer having a function of transporting holes. The electron transport layer is a layer having a function of transporting electrons. Note that the electron transport layer and the hole transport layer are collectively called a charge transport layer. As the light-emitting layer, hole transport layer and electron transport layer each may consists of two layers or more. Furthermore, the hole transport layer provided in adjacent to a light-emitting layer is sometimes called as an interlayer.

As a method for forming a light-emitting layer, a method of forming a film from a solution is mentioned. In forming a film from a solution, a spin coating method, a casting method, a microgravure coating method, a gravure coating method, a bar coating method, a roll coating method, a wire bar coating method, a dip coating method, a slit coating method, a cap coating method, a capillary coating method, a spray coating method, a screen printing method, a flexo printing method, an offset printing method, an inkjet printing method and a nozzle coating method can be used. Note that the formation of a film from a solution is useful for forming films of a hole transport layer and an electron transport layer (described later).

When a film is formed from a solution by using the polymer compound of the present invention in producing a light-emitting device, all that should be done after the solution is applied, is just removing a solvent by drying. Furthermore, even in the case where a charge transport material and a light-emitting material are added, the same procedure can be applied and thus favorable in production.

The film thickness of a light-emitting layer, which may be selected such that appropriate driving voltage and luminous efficiency values are obtained, is, for example, 1 nm to 1 μm, preferably 2 nm to 500 nm and further preferably 5 nm to 200 nm.

In the light-emitting device of the present invention, a light-emitting material except the aforementioned polymer compound may be used in combination in a light-emitting layer. Furthermore, in the light-emitting device of the present invention, a light-emitting layer containing a light-emitting material except the aforementioned polymer compound and a light-emitting layer containing the aforementioned polymer compound may be laminated.

Examples of a light-emitting material except the aforementioned polymer compound include low molecular compounds such as a naphthalene derivative, anthracene and a derivative thereof, perylene and a derivative thereof, pigments including a polymethine-based pigment, a xanthene-based pigment, a coumarin-based pigment and a cyanine-based pigment, a metal complex of 8-hydroxyquinoline and a derivative thereof, an aromatic amine, tetraphenylcyclopentadiene and a derivative thereof and tetraphenylbutadiene and a derivative thereof. In addition, the compounds described in JP 57-51781 A and JP 59-194393 A, etc. may be mentioned.

When the light-emitting device of the present invention has a hole transport layer, the hole transport material to be used herein is the same as the hole transport material described in the section of the liquid composition; however, preferable examples thereof include polymer hole transport materials such as polyvinylcarbazole and a derivative thereof, polysilane and a derivative thereof, a polysiloxane derivative having an aromatic amine compound group in the side chain or main chain, polyaniline and a derivative thereof, polythiophene and a derivative thereof, poly(p-phenylenevinylene) and a derivative thereof, poly(2,5-thenylenevinylene) and a derivative thereof. More preferable examples thereof include, polyvinyl carbazole and a derivative thereof, polysilane and a derivative thereof and a polysiloxane derivative having an aromatic amine in the side chain or main chain. In the case of a low molecular hole transport material, it is preferably dispersed in a polymer binder and put in use.

As a method for forming a hole transport layer, in the case of a low molecular hole transport material, a method for forming a film from a solution containing a polymer binder mixed therein is mentioned. Furthermore, in the case of a high-molecular hole transport material, a method for forming a film from a solution is mentioned.

As the polymer binder to be mixed, a polymer binder that does not significantly inhibit charge transport is preferable and a polymer binder that does not significantly absorb visible light is suitably used. Examples of the polymer binder include polycarbonate, polyacrylate, polymethylacrylate, polymethylmethacrylate, polystyrene, polyvinyl chloride and polysiloxane.

The film thickness of the hole transport layer, which may be selected such that appropriate driving voltage and luminous efficiency values are obtained, is for example, 1 nm to 1 μm, preferably 2 nm to 500 nm, and further preferably 5 nm to 200 nm.

When the light-emitting device of the present invention has an electron transport layer, the electron transport material to be used is the same as the electron transport material as described in the section of the liquid composition; however, preferable examples thereof include an oxadiazole derivative, benzoquinone and a derivative thereof, anthraquinone and a derivative thereof, a metal complex of 8-hydroxy quinoline and a derivative thereof, polyquinoline and a derivative thereof, polyquinoxaline and a derivative thereof and polyfluorene and a derivative thereof; and more preferable examples thereof include 2-(4-biphenylyl)-5-(4-t-butylphenyl)-1,3,4-oxadiazole, benzoquinone, anthraquinone, tris(8-quinolinol)aluminum and polyquinoline.

As a method for forming a film of the electron transport layer method, in the case of a low-molecular electron transport material, a vapor deposition method for forming a film from a powder, and a method for forming a film from a solution or a molten state are mentioned; in the case of a high-molecular electron transport material, a method for forming a film from a solution or a molten state is mentioned. When a film is formed from a solution or a molten state, a polymer binder may be used in combination.

As the polymer binder to be added, a polymer binder that does not significantly inhibit charge transport is preferable, and a polymer binder that does not significantly absorb visible light is suitably used. Examples of the polymer binder include poly(N-vinylcarbazole), polyaniline and a derivative thereof, polythiophene and a derivative thereof, poly(p-phenylenevinylene) and a derivative thereof, poly(2,5-thienylenevinylene) and a derivative thereof, polycarbonate, polyacrylate, polymethylacrylate, polymethylmethacrylate, polystyrene, polyvinyl chloride and polysiloxane.

The film thickness of the electron transport layer may be selected such that appropriate driving voltage and luminous efficiency values are obtained, for example, 1 nm to 1 μm, preferably 2 nm to 500 nm, and further preferably 5 nm to 200 nm.

Furthermore, of the charge transport layers provided in adjacent to an electrode, a charge transport layer having a function of improving an efficiency of charge injection from an electrode and having an effect of reducing the driving voltage of a device is sometimes particularly called a charge injection layer (hole injection layer, electron injection layer).

Furthermore, to improve adhesion with an electrode and to improve injection of charge from an electrode, the charge injection layer or an insulating layer may be provided in adjacent to the electrode. Moreover, to improve adhesion at the interface and prevent contamination, etc., a thin buffer layer may be inserted in the interface between a charge transport layer and a light-emitting layer.

The order and number of layers to be laminated and the thickness of each layer may be appropriately selected in consideration of luminous efficiency and device life.

In the present invention, as a light-emitting device having a charge injection layer provided therein, a light-emitting device having a charge injection layer provided in adjacent to a cathode and a light-emitting device having a charge injection layer provided in adjacent to an anode are mentioned.

Specific examples thereof include the following structures e) to p).

e) anode/charge injection layer/light-emitting layer/cathode,
f) anode/light-emitting layer/charge injection layer/cathode,
g) anode/charge injection layer/light-emitting layer/charge injection layer/cathode,
h) anode/charge injection layer/hole transport layer/light-emitting layer/cathode,
i) anode/hole transport layer/light-emitting layer/charge injection layer/cathode,
j) anode/charge injection layer/hole transport layer/light-emitting layer/charge injection layer/cathode,
k) anode/charge injection layer/light-emitting layer/charge transport layer/cathode,
l) anode/light-emitting layer/electron transport layer/charge injection layer/cathode,
m) anode/charge injection layer/light-emitting layer/electron transport layer/charge injection layer/cathode,
n) anode/charge injection layer/hole transport layer/light-emitting layer/charge transport layer/cathode,
o) anode/hole transport layer/light-emitting layer/electron transport layer/charge injection layer/cathode,
p) anode/charge injection layer/hole transport layer/light-emitting layer/electron transport layer/charge injection layer/cathode.

Examples of the charge injection layer include a layer containing a conductive polymer; a layer provided between an anode and a hole transport layer and containing a material having an intermediate ionization potential value between an anode material and a hole transport material contained in the hole transport layer, and a layer provided between a cathode and an electron transport layer and containing a material having an intermediate affinity value for electron between a cathode material and an electron transport material contained in the electron transport layer.

When the charge injection layer is a layer containing a conductive polymer, the electric conductivity of the conductive polymer is preferably $10^{-5}$ to $10^3$ S/cm. To reduce current leakage between emission pixels, the electric conductivity is more preferably $10^{-5}$ to $10^2$ S/cm and further preferably $10^{-5}$ to $10^1$ S/cm. Usually, to control the electric conductivity of the conductive polymer to be $10^{-5}$ to $10^3$ S/cm, an appropriately amount of ion is doped in the conductive polymer.

Type of ion to be doped is anion in the case of a hole injection layer and cation in the case of an electron injection layer. Examples of the anion include polystyrene sulfonate ion, alkyl benzene sulfonate ion and camphor sulfonate ion. Examples of the cations include a lithium ion, a sodium ion, a potassium ion and a tetrabutylammonium ion.

The film thickness of the charge injection layer is, for example, 1 nm to 100 nm and preferably 2 nm to 50 nm.

Examples of the material to be used for the charge injection layer include polyaniline and a derivative thereof, polythiophene and a derivative thereof, polypyrrole and a derivative thereof, polyphenylenevinylene and a derivative thereof, polythienylenevinylene and a derivative thereof, polyquinoline and a derivative thereof, polyquinoxaline and a derivative thereof, a conductive polymer such as a polymer having an aromatic amine structure in the main chain or side chain, metal phthalocyanine (copper phthalocyanine, etc.) and carbon.

The insulating layer is a layer having a function of facilitating charge injection. The average thickness of the insulating layer is, usually, 0.1 to 20 nm, preferably 0.5 to 10 nm and more preferably 1 to 5 nm. Examples of a material for the insulating layer include a metal fluoride, a metal oxide and an organic insulating material. As a light-emitting device having an insulating layer provided therein, a light-emitting device having an insulating layer provided in adjacent to a cathode and a light-emitting device having an insulating layer provided in adjacent to an anode are mentioned.

Specific examples thereof include the following structures q) to ab).

q) anode/insulating layer/light-emitting layer/cathode,
r) anode/light-emitting layer/insulating layer/cathode,
s) anode/insulating layer/light-emitting layer/insulating layer/cathode,
t) anode/insulating layer/hole transport layer/light-emitting layer/cathode,
u) anode/hole transport layer/light-emitting layer/insulating layer/cathode,
v) anode/insulating layer/hole transport layer/light-emitting layer/insulating layer/cathode,
w) anode/insulating layer/light-emitting layer/electron transport layer/cathode,
x) anode/light-emitting layer/electron transport layer/insulating layer/cathode,
y) anode/insulating layer/light-emitting layer/electron transport layer/insulating layer/cathode,
z) anode/insulating layer/hole transport layer/light-emitting layer/electron transport layer/cathode,
aa) anode/hole transport layer/light-emitting layer/electron transport layer/insulating layer/cathode,
ab) anode/insulating layer/hole transport layer/light-emitting layer/electron transport layer/insulating layer/cathode.

As the substrate for forming the light-emitting device of the present invention, any substrate may be used as long as it remains unchanged when an electrode is formed and an organic material layer is formed. Examples of the substrates include glass, plastic, a polymer film and silicon substrates. In the case of an opaque substrate, the opposite electrode is preferably transparent or semitransparent.

In the present invention, at least one of the electrodes comprising an anode and a cathode is usually transparent or semitransparent and preferably the anode is transparent or semitransparent.

As a material for the anode, a conductive metal oxide film and a semitransparent metal film, etc. are used. More specifically, a film (NESA, etc.) formed of conductive glass using indium oxide, zinc oxide, tin oxide and a complex thereof, that is, indium/tin/oxide (ITO) and indium/zinc/oxide, etc. gold, platinum, silver and copper, etc. are used, and ITO, indium/zinc/oxide and tin oxide are preferable. Examples of a forming method include a vapor deposition method, a sputtering method, an ion-plating method and a plating method. Furthermore, as the anode, a transparent conducting film of an organic substance such as polyaniline and a derivative thereof and polythiophene and a derivative thereof.

The film thickness of the anode is, in view of light permeability/electric conductivity, for example, 10 nm to 10 μm, preferably 20 nm to 1 μm and further preferably 50 nm to 500 nm.

Furthermore, to facilitate charge injection, a layer formed of e.g., a phthalocyanine derivative, a conductive polymer or carbon, or a layer formed of e.g., a metal oxide, a metal fluoride or an organic insulating material may be provided on the anode.

As a material for the cathode, a material having a small work function is preferable. Examples thereof that are used include a metal such as lithium, sodium, potassium, rubidium, cesium, beryllium, magnesium, calcium, strontium, barium, aluminum, scandium, vanadium, zinc, yttrium, indium, cerium, samarium, europium, terbium and ytterbium; an alloy of two or more types of them or an alloy of one or more of them with one or more of, e.g., gold, silver, platinum, copper, manganese, titanium, cobalt, nickel, tungsten and tin; and graphite or an graphite intercalation compound. Examples of the alloy include a magnesium-silver alloy, a magnesium-indium alloy, a magnesium-aluminum alloy, an indium-silver alloy, a lithium-aluminum alloy, a lithium-magnesium alloy, a lithium-indium alloy and a calcium-aluminum alloy. The cathode may have a laminate structure of 2 layers or more.

The film thickness of the cathode is, in view of electric conductivity and durability, for example, 10 nm to 10 μm, preferably 20 nm to 1 μm, and further preferably 50 nm to 500 nm.

As a method for forming the cathode, a vapor deposition method, a sputtering method and a laminate method in which a metal film is attached by thermo compression bonding are used. Furthermore, between the cathode and the organic material layer, a layer formed of a conductive polymer or a layer formed of a metal oxide, a metal fluoride, an organic insulating material or the like may be provided. Alternatively after the cathode is formed, a protecting layer for protecting the light-emitting device may be attached. To use the light-emitting device stably for a long time, a protecting layer and/or a protecting cover is preferably attached to protect the device from the outside.

As the protecting layer, a resin, a metal oxide, a metal fluoride and a metal borate, etc. can be used. Furthermore, as the protecting cover, a glass plate, a plastic plate having a surface treated to lower water permeability, and the like can be used. A method in which the cover is allowed to adhere airtight to a device substrate with a thermosetting resin or a light curable resin can be preferably used. If a spacer is used to keep a space, the device is easily protected from damage. If an inert gas such as nitrogen and argon is supplied to the space, the cathode can be prevented from being oxidized. Furthermore, if a desiccating agent such as barium oxide is placed in the space, the device is easily prevented from damage with a moisture content introduced by adsorption in a production step. At least one of these measures is preferably employed.

The light-emitting device of the present invention can be used in displays such as a surface light source, a segment display, a dot matrix display, a liquid crystal display (for example, a backlight) and a flat panel display.

To obtain a surface emission by using the light-emitting device of the present invention, a planar anode and cathode are arranged so as to overlap them. Furthermore, to obtain patterned emission of light, there are a method of placing a mask having a patterned window in the surface of the surface light-emitting device, a method of forming an extremely thick organic material layer in a non light-emitting section such that light is not substantially emitted, and a method of forming a patterned electrode as either one of an anode and cathode or both electrodes. Patterns are formed by any one of these methods and electrodes are arranged so as to independently turn ON/OFF. In this manner, a segment-type display device capable of displaying numeric characters and letters, and simple symbols, etc. can be obtained. Furthermore, to obtain a dot matrix device, an anode and a cathode are formed in the form of stripe and arranged so as to cross perpendicularly. A partial color display and multi-color display can be realized by a method of distinctively applying a plurality of types of polymer light-emitting materials different in luminous color and a method of using a color filter or a fluorescence conversion filter. A dot matrix device can be passively driven or may be actively driven in combination with TFT, etc. These display devices can be used as displays for computers, televisions, mobile terminals, mobile phones, car-navigation and view finders of video cameras, etc.

Furthermore, the surface light-emitting device is usually an autonomous light-emitting thin device and can be preferably used as a surface light source for a backlight of a liquid crystal display or surface illumination light source. For example, as the illumination light source, light emission such as white light emission, red light emission and green light emission or blue light emission are mentioned. Furthermore, if a flexible substrate is used, the light-emitting device can be used also as a curved-surface light source and a curved-surface display device.

EXAMPLES

Examples will be shown below to describe the present invention more specifically; however, the present invention is not limited to these.

Synthesis Example 1

Synthesis of Compound M-2

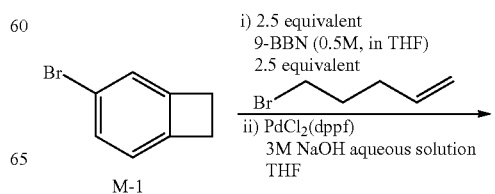

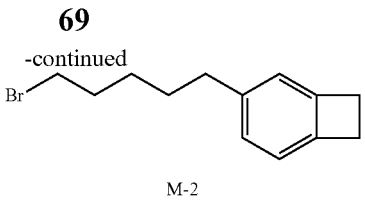

M-2

Under an argon atmosphere, in a 300 mL four-neck flask, 5-bromo-1-pentene (7.45 g) and THF (20 ml) were blended. To the resultant solution, 0.5 M 9-BBN/THF solution (100 ml) was added dropwise for one hour and then stirred at room temperature for 12 hours. To the resultant reaction solution, compound M-1 (3.66 g) represented by the above formula M-1, (diphenylphosphinoferrocene)palladium dichloride (0.82 g) and THF (32 ml) and a 3M aqueous sodium hydroxide solution (27 ml) were added and refluxed for 4 hours. After completion of the reaction, the resultant solution was cooled to room temperature. After hexane (40 ml) was added thereto and cooled on ice. To this, hydrogen peroxide water (6 ml) was slowly added dropwise and stirred for 1 hour. The reaction solution was separated into layers, and thereafter, the organic layer was washed 5 times with ion-exchanged water (50 ml). The organic layer obtained was dried over sodium sulfate and then purified by column chromatography using hexane as a developing solvent and silica gel as a filler to obtain compound M-2 represented by the above formula M-2.

GC-MS: 253[M]$^+$

Example 1

Synthesis of Compound M-3

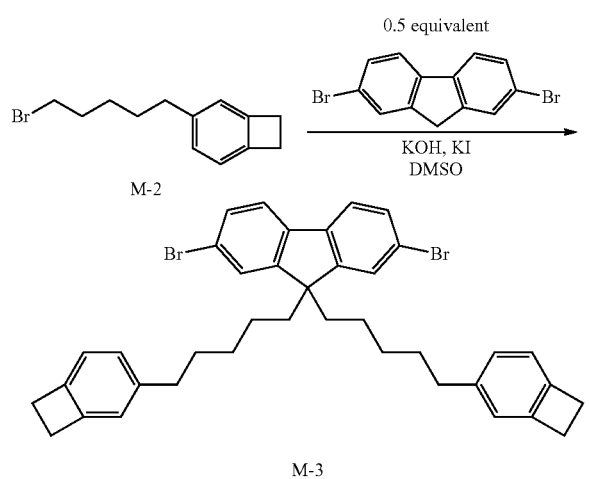

M-3

Under an argon atmosphere, in a 50 ml three-neck flask, 2,7-dibromofluorene (0.65 g), compound M-2 (1.1 g) represented by the above formula M-2, potassium hydroxide (0.48 g), potassium iodide (0.03 g) and dimethylsulfoxide (5 ml) were blended and heated to 80° C. for 4 hours. After completion of the reaction, the reaction solution was cooled to room temperature and water (10 ml) and toluene (10 ml) were added thereto. After layers were separated, the organic layer obtained was washed 5 times with a saturated aqueous sodium chloride solution (10 ml). The organic layer obtained was dried over sodium sulfate and then purified by column chromatography using hexane as a developing solvent and silica gel as a filler to obtain compound M-3 represented by the above formula M-3.

LC-MS (APPI-MS (posi)): 668 [M]$^+$ $^1$H-NMR (270 MHz, CDCl$_3$); δ=0.59 (tt, 4H), 1.08 (tt, 4H), 1.35 (tt, 4H), 1.89 (t, 4H), 2.38 (t, 4H), 3.11 (t, 8H), 6.77 (s, 2H), 6.89 (dd, 4H), 7.41-7.52 (m, 6H).

Synthesis Example 2

Synthesis of Compound M-4

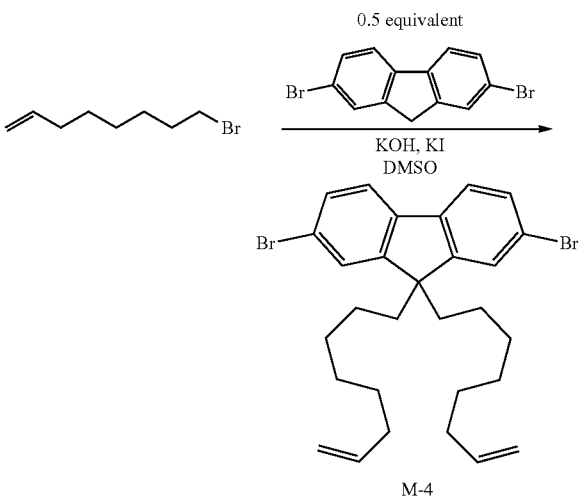

M-4

Under an argon atmosphere, in a 300 ml three-neck flask, 2,7-dibromofluorene (8.1 g), 8-bromo-1-octene (10.0 g), potassium hydroxide (6.0 g), potassium iodide (0.42 g) and dimethylsulfoxide (60 ml) were blended and warmed to 80° C. for 4 hours. After completion of the reaction, the reaction solution was cooled to room temperature. To this, water (100 ml) and toluene (100 ml) were blended. After layers were separated, the resultant organic layer was washed 5 times with a saturated aqueous sodium chloride solution (100 ml). After the resultant organic layer was dried over sodium sulfate, purification was performed by column chromatography using hexane as a developing solvent and silica gel as a filler to obtain compound M-4 represented by the above formula M-4.

ESI-MS: 544 [M]$^+$ $^1$H-NMR (270 MHz, CDCl$_3$); δ=0.58 (m, 4H), 1.06 (m, 8H), 1.18 (m, 4H), 1.92 (m, 8H), 4.90 (d, 4H), 5.73 (m, 2H), 7.43-7.52 (m, 6H).

Synthesis Example 3

Synthesis of Compound M-5

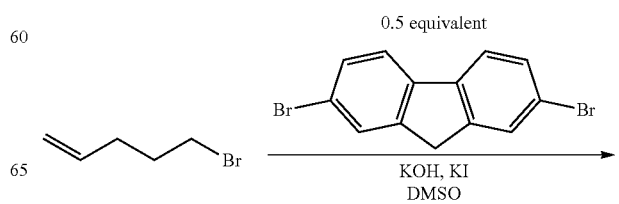

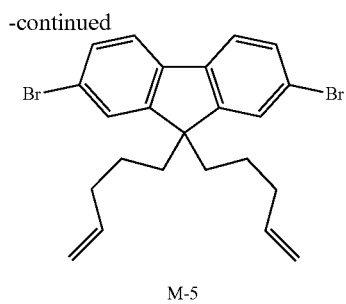

M-5

Under an argon atmosphere, in a 500 ml four-neck flask, 2,7-dibromofluorene (22.7 g), 5-bromo-1-octene (21.9 g), potassium hydroxide (16.7 g), potassium iodide (1.2 g) and dimethylsulfoxide (170 ml) were blended and warmed to 80° C. for 4 hours. After completion of the reaction, the resultant reaction solution was cooled to room temperature. To this, water (300 ml) and toluene (300 ml) were added and layers were separated. Subsequently, the resultant organic layer was washed 5 times with a saturated aqueous sodium chloride solution (300 ml). After the resultant organic layer was dried over sodium sulfate, purification was performed by column chromatography using hexane as a developing solvent and silica gel as a filler to obtain compound M-5 represented by the above formula M-5.

ESI-MS: 460 [M]$^+$ $^1$H-NMR (270 MHz, CDCl$_3$); δ=0.69 (t, 4H), 1.83 (m, 4H), 1.93 (m, 4H), 4.85 (d, 4H), 5.56 (m, 2H), 7.44-7.53 (m, 6H).

Synthesis Example 4

Synthesis of Compound M-7

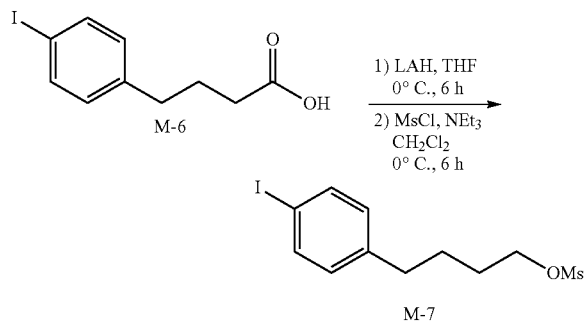

Under an argon atmosphere, in a 300 mL three-neck flask, compound M-6 (8.1 g) represented by the above formula M-6 and tetrahydrofuran (20 mL) were blended and cooled to 0° C. To this, a tetrahydrofuran solution (1 M) of lithium aluminum hydride was added dropwise. Thereafter, the mixture was stirred at 0° C. for 4 hours. After completion of the reaction, an aqueous sodium hydroxide solution (20 ml) was added and layers were separated. The organic layer obtained was dried over sodium sulfate, and concentrated to dryness. This was dissolved in methylene chloride (150 ml) and cooled to 0° C. To this, triethylamine (6 mL) and mesyl chloride (2.6 mL) were added. The mixture was stirred for 6 hours, and then water (50 mL) was added thereto, and extracted with chloroform. The organic layer was dried over sodium sulfate, and concentrated to dryness. Thereafter, purification was performed by column chromatography using hexane: chloroform=5:1 as a developing solvent and alumina as a filler to obtain compound M-7 represented by the above formula M-7.

$^1$H-NMR (300 MHz, CDCl$_3$); δ=7.31-7.17 (m, 4H), 4.23 (t, 2H), 2.66 (t, 2H), 1.81-1.76 (m, 4H).

Synthesis Example 5

Synthesis of Compound M-9

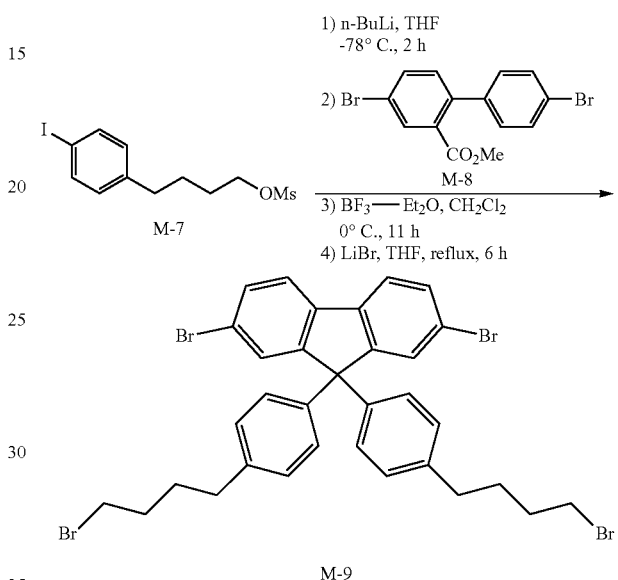

Under an argon atmosphere, in a 200 mL three-neck flask, compound M-7 (8.1 g) represented by the above formula M-7 and tetrahydrofuran (30 mL) were blended and cooled to −78° C. To this, a hexane solution (1.6 M) of normal butyl lithium was added dropwise. Thereafter, the mixture was stirred at −78° C. for 2 hours. Subsequently, to the reaction solution, a tetrahydrofuran solution of compound M-8 (2-methoxycarbonyl-4,4'-dibromobiphenyl) (6.4 g) represented by the above formula M-8 was added and further stirred at −78° C. for 1 hour, and then increased to room temperature. After completion of the reaction, water (20 mL) was added and layers were separated. The organic layer obtained was then dried over sodium sulfate, and concentrated to dryness. This was dissolved in methylene chloride (150 mL) and cooled to 0° C. To this, a boron trifluoride ethyl ether complex (17 mL) was added. The mixture was stirred for 11 hours, and then water (50 mL) was added thereto, and extracted with chloroform. The organic layer was dried over sodium sulfate, and concentrated to dryness. This was dissolved in tetrahydrofuran (30 mL) and lithium bromide (1.2 g) was added and heated to reflux for 6 hours. Thereafter, layers were separated and the organic layer obtained was dried over sodium sulfate, and concentrated to dryness. Subsequently, purification was performed by column chromatography using hexane: chloroform=4:1 as a developing solvent and alumina as a filler to obtain compound M-9 represented by the above formula M-9.

$^1$H-NMR (300 MHz, CDCl$_3$); δ=7.32-6.99 (m, 14H), 3.42 (t, 4H), 2.65 (t, 4H), 1.95-1.73 (m, 8H).

Note that the compound represented by the above formula M-8 was synthesized by a method described in Journal of the American Chemical Society (1956), 78, 3196-3198.

Example 2

Synthesis of Compound M-10

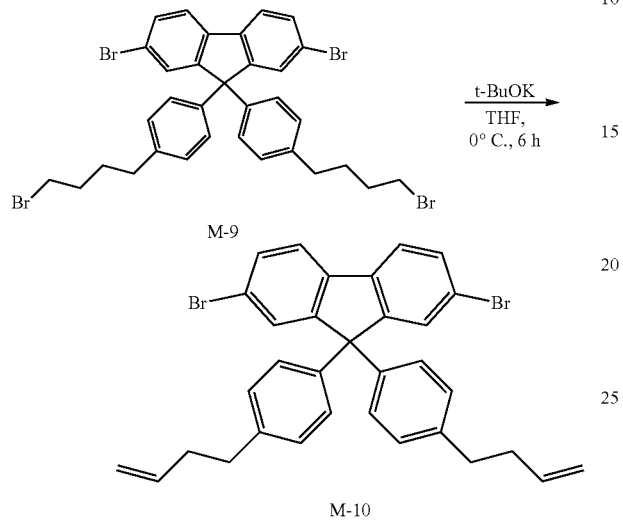

Under an argon atmosphere, in a 100 mL three-neck flask, tert-butoxy potassium (808 mg) and tetrahydrofuran (3 mL) were blended and cooled to 0° C. To this, a tetrahydrofuran solution (0.5 M) of compound M-9 (3.6 g) represented by the above formula M-9 was added dropwise. Thereafter, the mixture was stirred at 0° C. for 6 hours, increased to room temperature and further stirred for 12 hours. After completion of the reaction, water (20 mL) was added and layers were separated. The organic layer obtained was dried over sodium sulfate, and concentrated to dryness. Subsequently, purification was performed by column chromatography using hexane: chloroform=4:1 as a developing solvent and alumina as a filler to obtain compound M-10 represented by the above formula M-10.

$^1$H-NMR (300 MHz, CDCl$_3$); δ=7.30-7.18 (m, 14H), 5.93-5.80 (m, 2H), 5.07-4.96 (m, 4H), 3.35 (t, 4H), 2.63 (t, 4H)

Synthesis Example 6

Synthesis of Compound MM-X

Compound MM-X

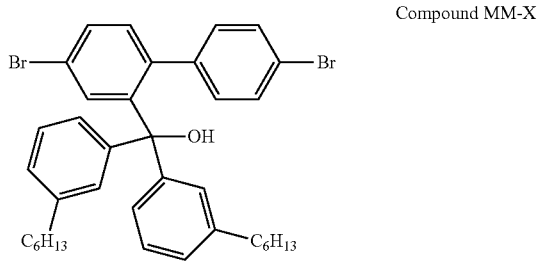

A 5 L-three-neck flask was purged with nitrogen. 1-Bromo-3-n-hexylbenzene (226 g) was weighed and dissolved in a 2.5 L dewatered THF. This solution was cooled to −75° C. or less and a 2.5 M n-butyllithium/hexane solution (358 ml) was added dropwise and stirred for 5 hours while the temperature was kept at −75° C. or less. To this solution, a solution of 2-methoxycarbonyl-4,4'-dibromobiphenyl (150 g) dissolved in 400 ml of dewatered THF was added dropwise while the temperature was kept at −70° C. or less. The solution was gradually increased to room temperature and then stirred overnight. While the reaction solution was stirred at 0° C., 150 ml of water was added dropwise. After a solvent was distilled away, water (200 ml) was added to the residue. Extraction was performed once with hexane (1 L) and twice with hexane (100 ml). Organic layers were combined and washed with a saturated saline solution (200 ml). The water layer was re-extracted with hexane (100 ml) and then, dried over magnesium sulfate. The solvent was distilled away to obtain a crude product (264 g) of compound MM-X and used in the next step without purification.

Synthesis Example 7

Synthesis of Compound MM-Y

Compound MM-Y

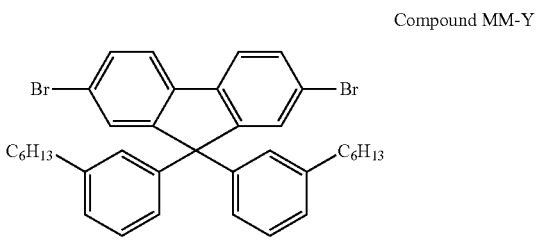

In a 3 L-three neck flask, compound MM-X (264 g) synthesized above was weighed, dissolved in dichloromethane (900 ml) and purged with nitrogen. This solution was cooled to 0° C. or less and a boron trifluoride diethyl ether complex (245 ml) was added dropwise while the temperature was kept at 5° C. or less. After the solution was slowly increased to room temperature, it was stirred overnight. This reaction solution was poured in a 2 L of ice water while stirring and stirred for 30 minutes. The layers were separated and the water layer was extracted with 100 ml of dichloromethane. Organic layers were combined and a 10% aqueous potassium phosphate solution (1 L) was added and then layers were separated. The organic layer was washed twice with water (1 L), dried over magnesium sulfate and then the solvent was distilled away. The resultant oil was dissolved in 200 ml of toluene and passed through a glass filter lined with silica gel to filtrate. After the solvent was distilled away, 500 ml of methanol was added and vigorously stirred. The resultant crystal was filtrated and washed with methanol. Recrystallization was performed from a solvent mixture of hexane/butyl acetate to obtain compound MM-Y (121 g).

$^1$H-NMR (300 MHz, CDCl$_3$); δ0.86 (6H, t), 1.26 (12H, m), 1.52 (4H, m), 2.51 (4H, t), 6.87 (2H, d), 7.00 (2H, s), 7.04 (2H, d), 7.12 (2H, t), 7.46 (2H, dd), 7.48 (2H, d), 7.55 (2H, d) ppm

Synthesis Example 8

Synthesis of Compound MM-2

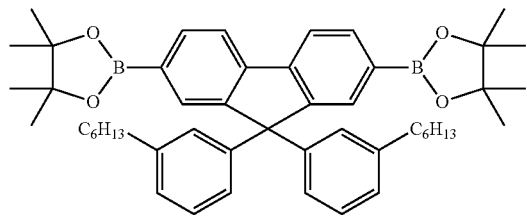

Compound MM-2

In a 2 L three-neck flask, compound MM-Y (50 g) was weighted and purged with nitrogen. Dewatered THF (500 ml) was added and cooled to −70° C. or less. While the solution was kept at −70° C. or less, a 2.5 M n-butyl lithium/hexane solution (68 ml) was added dropwise. After dropwise addition, the solution was stirred for 4 hours while keeping the temperature. 2-Isopropoxy-4,4,5,5-tetramethyl-1,3,2-dioxaborolane (44 ml) was added and then the solution was slowly increased to room temperature and stirred overnight. The solution was cooled to −30° C. and a 2 M hydrochloric acid/diethyl ether solution (78 ml) was added dropwise thereto and then the temperature of the solution was increased to room temperature. After the solvent was distilled away, the resultant substance was dissolved by adding toluene (400 ml) and filtrated by passing it through a glass filter lined with silica gel. When the solvent of the resultant solution was distilled away to obtain a crude product (50 g). Under a nitrogen atmosphere, recrystallization was performed from a toluene/acetonitrile solvent to obtain 34 g of compound MM-5.

$^1$H-NMR (300 MHz, CDCl$_3$); δ0.86 (6H, t), 1.26-1.29 (12H, m), 1.31 (24H, s), 1.52-1.53 (4H, m), 2.50 (4H, t), 6.92 (2H, d), 7.00 (2H, d), 7.08 (2H, t), 7.13 (2H, s), 7.77 (2H, d), 7.81-7.82 (4H, m) ppm.

Example 3

Synthesis of Polymer Compound P-1

Under an inert gas atmosphere, 2,7-bis(1,3,2-dioxaborolan-2-yl)-9,9-dioctylfluorene (1.06 g), bis(4-bromophenyl)-(4-sec-butylphenyl)-amine (0.73 g), compound M-5 (0.09 g) represented by the above formula M-5, compound M-3 (0.13 g) represented by the above formula M-3, bis triphenylphosphine palladium dichloride (1.4 mg), trioctylmethylammonium chloride (trade name: Aliquat 336, manufactured by Aldrich) (0.25 g) and toluene (40 ml) were blended and heated to 105° C. To the resultant reaction solution, a 2 M aqueous sodium carbonate solution (6 ml) was added dropwise and refluxed for 5 hours. After completion of the reaction, phenylboric acid (240 mg) was added and refluxed for further 4 hours. Subsequently, to this, a 1.8 M aqueous sodium diethyldithiacarbamate solution (10 ml) was added and stirred at 80° C. for 4 hours. The resultant reaction solution was cooled to room temperature, then washed three times with water (30 ml), three times with a 3 wt % aqueous acetic acid solution (30 ml) and three times with water (30 ml), and purified by passing it through an alumina column and a silica gel column. The resultant toluene solution was added dropwise to methanol (300 ml) and stirred for one hour. Thereafter, the resultant solid substance was filtrated and dried to obtain polymer compound P-1 (0.7 g) represented by the following formula:

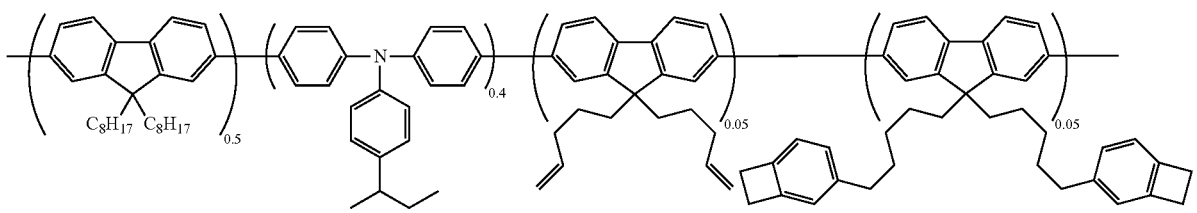

wherein the numbers attached outside parentheses each represent a molar ratio of a repeating unit.

The polystyrene-equivalent number average molecular weight of polymer compound P-1 was 1.2×10$^5$ and the polystyrene-equivalent weight average molecular weight thereof was 3.8×10$^5$.

Note that bis(4-bromophenyl)-(4-sec-butylphenyl)-amine was synthesized by a method described in WO2002/045184.

Example 4

Synthesis of Polymer Compound P-2

Under an inert gas atmosphere, 2,7-bis(1,3,2-dioxaborolan-2-yl)-9,9-dioctylfluorene (1.06 g), bis(4-bromophenyl)-(4-sec-butylphenyl)-amine (0.37 g), compound M-4 represented by the above formula M-4 (0.44 g), compound M-3 represented by the above formula M-3 (0.27 g), bis triphenylphosphine palladium dichloride (1.4 mg), trioctylmethylammonium chloride (trade name: Aliquat 336, manufactured by Aldrich) (0.25 g) and toluene (40 ml) were blended and heated to 105° C. To the resultant reaction solution, a 2 M aqueous sodium carbonate solution (6 ml) was added dropwise and refluxed for 5 hours. After completion of the reaction, phenylboric acid (240 mg) was added and refluxed for further 4 hours. Subsequently, a 1.8 M aqueous sodium diethyldithiacarbamate solution (10 ml) was added and stirred at 80° C. for 4 hours. The resultant reaction solution was cooled to room temperature, then washed three times with water (30 ml), three times with a 3 wt % aqueous acetic acid solution (30 ml) and three times with water (30 ml), and purified by passing it through an alumina column and a silica gel column. The resultant toluene solution was added dropwise to methanol (300 ml) and stirred for one hour. Thereafter, the resultant solid substance was filtrated and dried to obtain polymer compound P-2 (0.8 g) represented by the following formula:

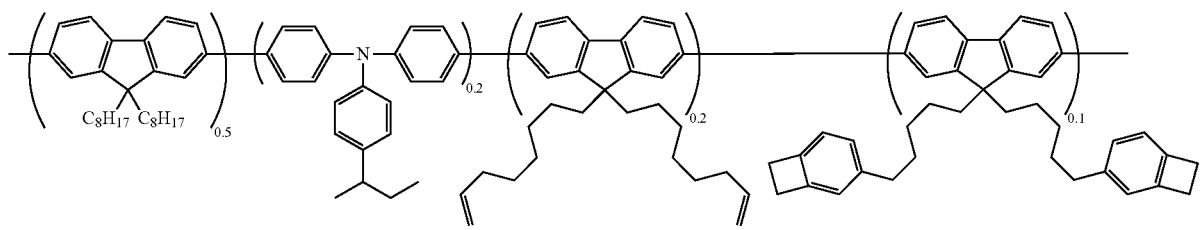

wherein the numbers attached outside parentheses each represent a molar ratio of a repeating unit.

The polystyrene-equivalent number average molecular weight of polymer compound P-2 was $4.3 \times 10^4$ and the polystyrene-equivalent weight average molecular weight thereof was $2.1 \times 10^5$.

Example 5

Synthesis of Polymer Compound P-3

Under an inert gas atmosphere, 2,7-bis(1,3,2-dioxaborolan-2-yl)-9,9-dioctylfluorene (1.06 g), 2,7-dibromo-9,9-dioctylfluorene (0.66 g), compound M-5 represented by the above formula M-5 (0.18 g), compound M-3 represented by the above formula M-3 (0.27 g), bis triphenylphosphine palladium chloride (1.4 mg), trioctylmethylammonium chloride (trade name: Aliquat 336, manufactured by Aldrich) (0.25 g) and toluene (40 ml) were blended and heated to 105° C. To the resultant reaction solution, a 2 M aqueous sodium carbonate solution (6 ml) was added dropwise and refluxed for 10 hours. After completion of the reaction, phenylboric acid (240 mg) was added and refluxed for further 4 hours. Subsequently, a 1.8 M aqueous sodium diethyldithiacarbamate solution (10 ml) was added and stirred at 80° C. for 4 hours. The resultant reaction solution was cooled to room temperature, then washed three times with water (30 ml), three times with a 3 wt % aqueous acetic acid solution (30 ml) and three times with water (30 ml), and purified by passing it through an alumina column and a silica gel column. The resultant toluene solution was added dropwise to methanol (300 ml) and stirred for one hour. Thereafter, the resultant solid substance was filtrated and dried to obtain polymer compound P-3 (1.1 g) represented by the following formula:

Example 6

Synthesis of Polymer Compound P-4

Under an inert gas atmosphere, 2,7-bis(1,3,2-dioxaborolan-2-yl)-9,9-dioctylfluorene (1.06 g), 2,7-dibromo-9,9-dioctylfluorene (0.55 g), N,N'-(4-bromophenyl)-N—N'-(4-n-butylphenyl)-1,4-phenylenediamine (0.14 g), compound MM-4 represented by the above formula M-4 (0.17 g), compound MM-1 (0.25 g) represented by the following formula (MM-1):

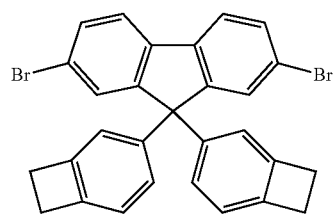

MM-1 palladium acetate (0.4 mg), tris(o-methoxyphenyl)phosphine (2.8 mg), trioctylmethylammonium chloride (trade name: Aliquat 336, manufactured by Aldrich) (0.25 g) and toluene (40 ml) were blended and heated to 105° C. To the resultant reaction solution, a 2 M aqueous sodium carbonate solution (6 ml) was added dropwise and refluxed for 18 hours. After completion of the reaction, phenylboric acid (240 mg) was added and refluxed for further 4 hours. Subsequently, a 1.8 M aqueous sodium diethyldithiacarbamate solution (10 ml) was added and stirred at 80° C. for 4 hours. The resultant reaction

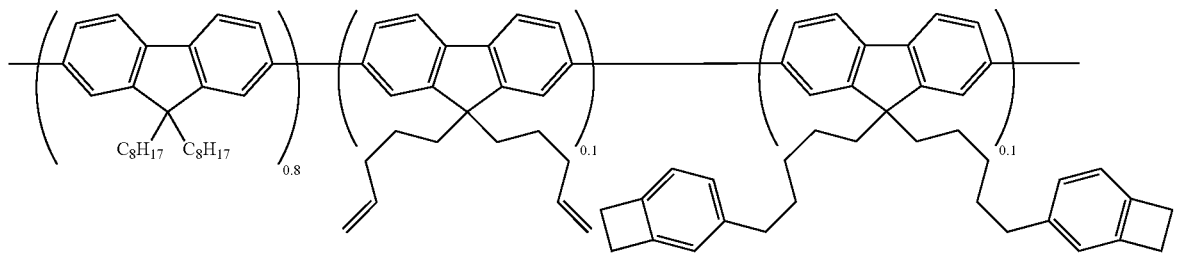

wherein the numbers attached outside parentheses each represent a molar ratio of a repeating unit.

The polystyrene-equivalent number average molecular weight of polymer compound P-3 was $1.5 \times 10^4$ and the polystyrene-equivalent weight average molecular weight thereof was $3.4 \times 10^4$.

solution was cooled to room temperature, then washed three times with water (30 ml), three times with a 3 wt % aqueous acetic acid solution (30 ml) and three times with water (30 ml), and purified by passing it through an alumina column and a silica gel column. The resultant toluene solution was added dropwise to methanol (300 ml) and stirred for one hour.

Thereafter, the resultant solid substance was filtrated and dried to obtain polymer compound P-4 (0.9 g) represented by the following formula (P-4):

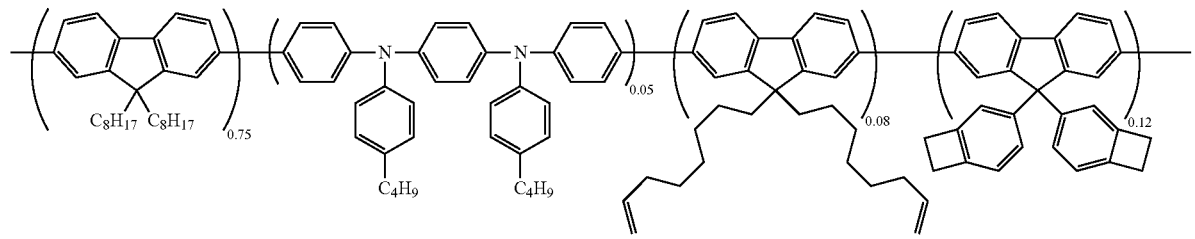

wherein the numbers attached outside parentheses each represent a molar ratio of a repeating unit.

The polystyrene-equivalent number average molecular weight of polymer compound P-4 was $6.9 \times 10^4$ and the polystyrene-equivalent weight average molecular weight thereof was $2.2 \times 10^5$.

Note that compound MM-1 represented by the above formula MM-1 was synthesized by a method described in JP 2008-106241 A.

Example 7

Synthesis of Polymer Compound P-5

Under an inert gas atmosphere, compound MM-2 (1.48 g) represented by the above formula MM-2,2,7-dibromo-9,9-dioctylfluorene (0.22 g), compound M-5 (0.09 g) represented by the above formula M-5, compound MM-1 (0.11 g) represented by the above formula MM-1, compound MM-3 (0.57 g) represented by the following formula MM-3:

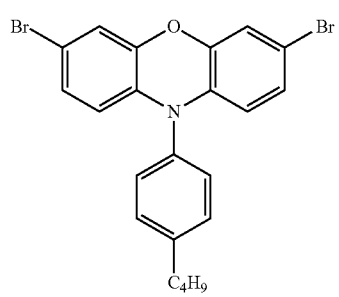

palladium acetate (0.4 mg), tris(o-methoxyphenyl)phosphine (2.8 mg), and toluene (44 ml) were blended and heated to 105° C. To the resultant reaction solution, a 20% aqueous triethylammonium hydroxide solution (7 ml) was added dropwise and refluxed for 5 hours. After completion of the reaction, phenylboric acid (244 mg) was added and refluxed for further 18 hours. Subsequently, a 1.8 M aqueous sodium diethyldithiacarbamate solution (20 ml) was added and stirred at 80° C. for 4 hours. The resultant reaction solution was cooled to room temperature, then washed three times with water (30 ml), three times with a 3 wt % aqueous acetic acid solution (30 ml) and three times with water (30 ml), and purified by passing it through an alumina column and a silica gel column. The resultant toluene solution was added dropwise to methanol (300 ml) and stirred for one hour. Thereafter, the resultant solid substance was filtrated and dried to obtain polymer compound P-5 (1.3 g) represented by the following formula P-5:

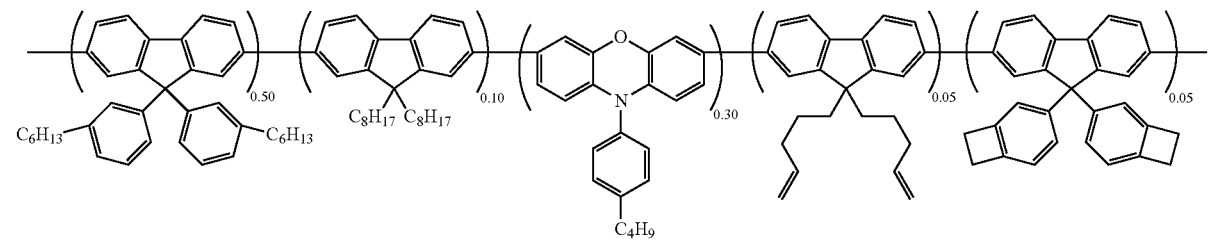

wherein the numbers attached outside parentheses each represent a molar ratio of a repeating unit.

The polystyrene-equivalent number average molecular weight of polymer compound P-5 was $2.1 \times 10^5$ and the polystyrene-equivalent weight average molecular weight thereof was $6.8 \times 10^5$.

Note that compound MM-3 represented by the above formula MM-3 was synthesized by a method described in US20040127666.

Example 8

Synthesis of Polymer Compound P-6

Under an inert gas atmosphere, compound MM-2 (3.69 g) represented by the above formula MM-2,2,7-dibromo-9,9-dioctylfluorene (0.55 g), compound M-5 (0.23 g) represented by the above formula M-5, compound M-3 (0.33 g) represented by the above formula M-3, compound MM-4 (2.04 g) represented by the following formula MM-4:

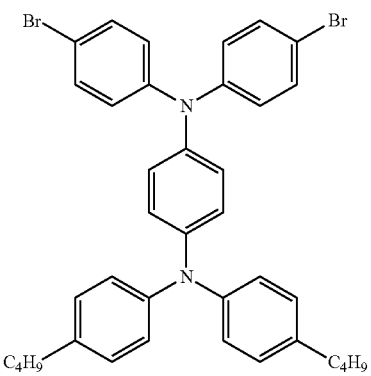

MM-4 palladium acetate (1.1 mg), tris(o-methoxyphenyl)phosphine (7.0 mg), and toluene (110 ml) were blended and heated to 105° C. To the resultant reaction solution, a 20% aqueous triethylammonium hydroxide solution (17 ml) was added dropwise and refluxed for 4 hours. After completion of the reaction, phenylboric acid (600 mg) was added and refluxed for further 20 hours. Subsequently, a 1.8 M aqueous sodium diethyldithiacarbamate solution (55 ml) was added and stirred at 80° C. for 4 hours. The resultant reaction solution was cooled to room temperature, then washed three times with water (70 ml), three times with a 3 wt % aqueous acetic acid solution (70 ml) and three times with water (70 ml), and purified by passing it through an alumina column and a silica gel column. The resultant toluene solution was added dropwise to methanol (800 ml) and stirred for one hour. Thereafter, the resultant solid substance was filtrated and dried to obtain polymer compound P-6 (4.1 g) represented by the following formula P-6:

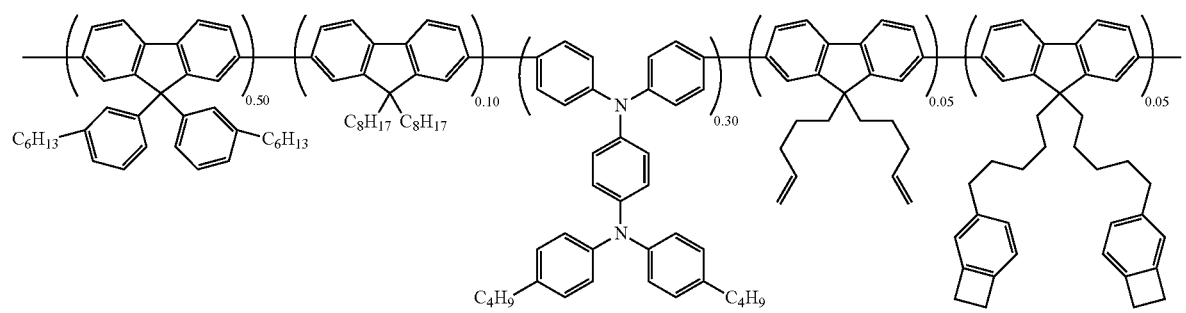

wherein the numbers attached outside parentheses each represent a molar ratio of a repeating unit.

The polystyrene-equivalent number average molecular weight of polymer compound P-6 was $9.1 \times 10^4$ and the polystyrene-equivalent weight average molecular weight thereof was $4.3 \times 10^5$.

Note that compound MM-4 represented by the above formula MM-4 was synthesized by a method described in JP 2003-226744 A.

Example 9

Synthesis of Polymer Compound P-7

Under an inert gas atmosphere, compound MM-2 (1.48 g) represented by the above formula MM-2, 2,7-dibromo-9,9-dioctylfluorene (0.22 g), compound M-5 (0.09 g) represented by the above formula M-5, compound M-3 (0.11 g) represented by the above formula M-3, compound MM-5 (1.09 g) represented by the following formula MM-5:

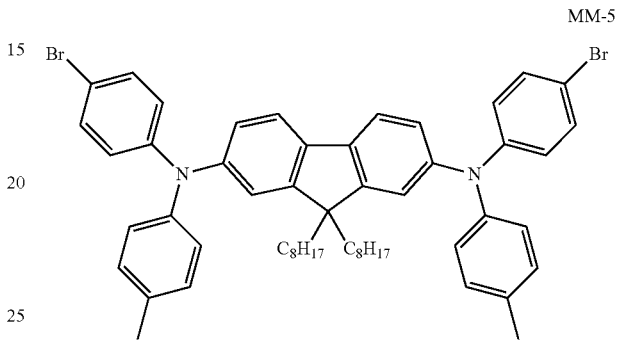

MM-5 palladium acetate (0.4 mg), tris(o-methoxyphenyl)phosphine (2.8 mg), and toluene (44 ml) were blended and heated to 105° C. To the resultant reaction solution, a 20% aqueous triethylammonium hydroxide solution (7 ml) was added dropwise and refluxed for 4 hours. After completion of the reaction, phenylboric acid (244 mg) was added and refluxed for further 20 hours. Subsequently, a 1.8 M aqueous sodium diethyldithiacarbamate solution (20 ml) was added and stirred at 80° C. for 4 hours. The resultant reaction solution was cooled to room temperature, then washed three times with water (30 ml), three times with a 3 wt % aqueous acetic acid solution (30 ml) and three times with water (30 ml), and purified by passing it through an alumina column and a silica gel column. The resultant toluene solution was added dropwise to methanol (300 ml) and stirred for one hour. Thereafter, the resultant solid substance was filtrated and dried to obtain polymer compound P-7 (1.7 g) represented by the following formula P-7:

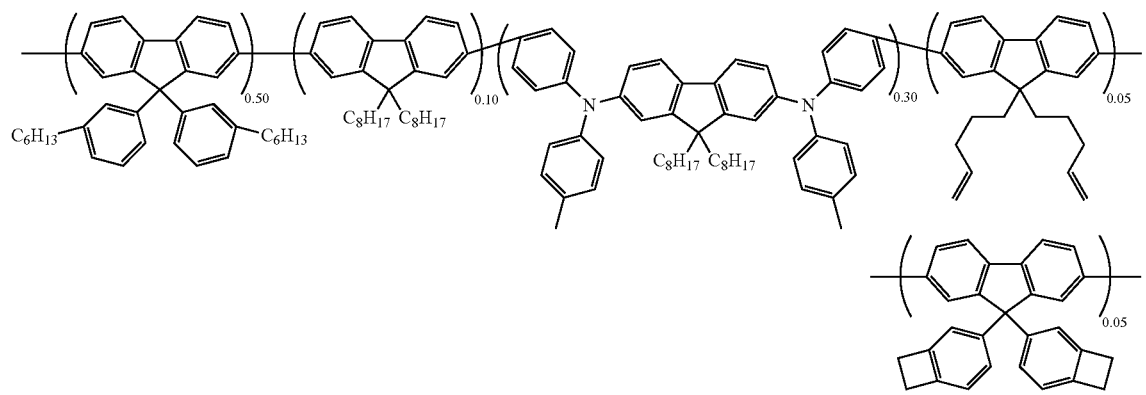

wherein the numbers attached outside parentheses each represent a molar ratio of a repeating unit.

The polystyrene-equivalent number average molecular weight of polymer compound P-7 was $5.4\times10^5$ and the polystyrene-equivalent weight average molecular weight thereof was $1.1\times10^6$.

Note that compound MM-5 represented by the above formula MM-5 was synthesized by a method described in WO2005049548.

Example 10

Synthesis of Polymer Compound P-8

Under an inert gas atmosphere, compound MM-2 (1.48 g) represented by the above formula MM-2, 2,7-dibromo-9,9-dioctylfluorene (0.22 g), compound M-5 (0.09 g) represented by the above formula M-5, compound M-3 (0.11 g) represented by the above formula M-3, compound MM-6 (0.58 g) represented by the following formula MM-6:

palladium acetate (0.4 mg), tris(o-methoxyphenyl)phosphine (2.8 mg), and toluene (44 ml) were blended and heated to 105° C. To the resultant reaction solution, a 20% aqueous triethylammonium hydroxide solution (7 ml) was added dropwise and refluxed for 4 hours. After completion of the reaction, phenylboric acid (244 mg) was added and refluxed for further 20 hours. Subsequently, a 1.8 M aqueous sodium diethyldithiacarbamate solution (20 ml) was added and stirred at 80° C. for 4 hours. The resultant reaction solution was cooled to room temperature, then washed three times with water (30 ml), three times with a 3 wt % aqueous acetic acid solution (30 ml) and three times with water (30 ml), and purified by passing it through an alumina column and a silica gel column. The resultant toluene solution was added dropwise to methanol (300 ml) and stirred for one hour. Thereafter, the resultant solid substance was filtrated and dried to obtain polymer compound P-8 (1.2 g) represented by the following formula P-8:

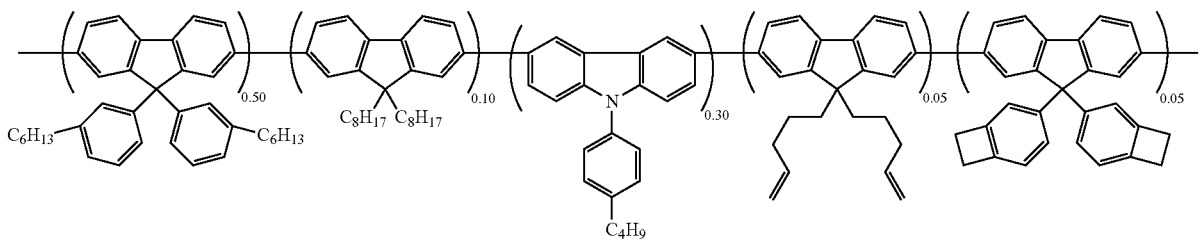

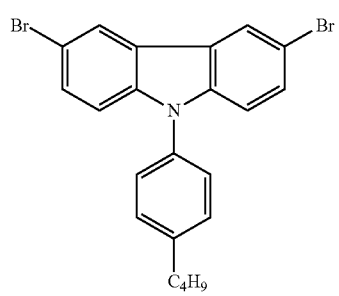

wherein the numbers attached outside parentheses each represent a molar ratio of a repeating unit.

The polystyrene-equivalent number average molecular weight of polymer compound P-8 was $7.2\times10^4$ and the polystyrene-equivalent weight average molecular weight thereof was $3.61\times10^5$.

Note that compound MM-6 represented by the above formula MM-6 was synthesized by a method described in WO2006126439.

Comparative Example 1

Synthesis of Polymer Compound C-1

Under an inert gas atmosphere, 2,7-bis(1,3,2-dioxaborolan-2-yl)-9,9-dioctylfluorene (1.06 g), bis(4-bromophenyl)-(4-sec-butylphenyl)-amine (0.87 g), compound MM-7 (0.04 g) represented by the following formula MM-7:

MM-7

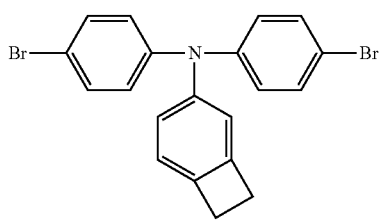

bis triphenylphosphine palladium dichloride (1.4 mg), trioctylmethylammonium chloride (trade name: Aliquat 336, manufactured by Aldrich) (0.25 g) and toluene (40 ml) were blended and heated to 105° C. To the resultant reaction solution, a 2 M aqueous sodium carbonate solution (6 ml) was added dropwise and refluxed for 7 hours. After completion of the reaction, phenylboric acid (240 mg) was added and refluxed for further 4 hours. Subsequently, a 1.8 M aqueous sodium diethyldithiacarbamate solution (10 ml) was added and stirred at 80° C. for 4 hours. The resultant reaction solution was cooled to room temperature, then washed three times with water (30 ml), three times with a 3 wt % aqueous acetic acid solution (30 ml) and three times with water (30 ml), and purified by passing it through an alumina column and a silica gel column. The resultant toluene solution was added dropwise to methanol (300 ml) and stirred for one hour. Thereafter, the resultant solid substance was filtrated and dried to obtain polymer compound C-1 (0.8 g) represented by the following formula:

Note that compound MM-7 represented by the above formula MM-7 was synthesized by a method described in US2004/035221.

Comparative Example 2

Synthesis of Polymer Compound C-2

Under an inert gas atmosphere, 2,7-bis(1,3,2-dioxaborolan-2-yl)-9,9-dioctylfluorene (1.06 g), 2,7-dibromo-9,9-dioctylfluorene (0.22 g), bis(4-bromophenyl)-(4-sec-butylphenyl)-amine (0.55 g), compound MM-1 (0.21 g) represented by the above formula MM-1, bis triphenylphosphine palladium dichloride (1.4 mg), trioctylmethylammonium chloride (trade name: Aliquat 336, manufactured by Aldrich) (0.25 g) and toluene (40 ml) were blended and heated to 105° C. To the resultant reaction solution, a 2 M aqueous sodium carbonate solution (6 ml) was added dropwise and refluxed for 7 hours. After completion of the reaction, phenylboric acid (240 mg) was added and refluxed for further 4 hours. Subsequently, a 1.8 M aqueous sodium diethyldithiacarbamate solution (10 ml) was added and stirred at 80° C. for 4 hours. The resultant reaction solution was cooled to room temperature, then washed three times with water (30 ml), three times with a 3 wt % aqueous acetic acid solution (30 ml) and three times with

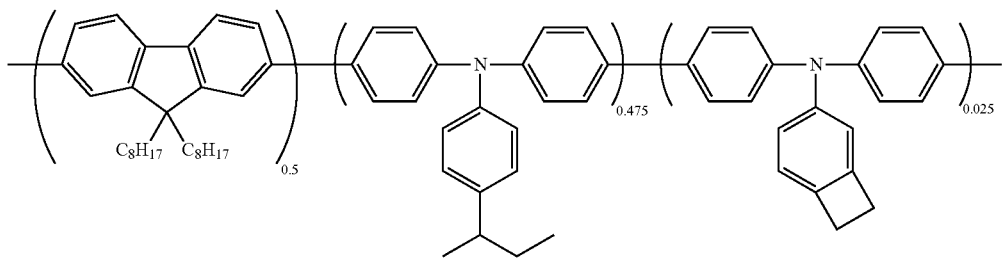

wherein the numbers attached outside parentheses each represent a molar ratio of a repeating unit.

The polystyrene-equivalent number average molecular weight of polymer compound C-1 was $3.4 \times 10^4$ and the polystyrene-equivalent weight average molecular weight thereof was $6.7 \times 10^4$.

water (30 ml) and purified by passing it through an alumina column and a silica gel column. The resultant toluene solution was added dropwise to methanol (300 ml) and stirred for one hour. Thereafter the resultant solid substance was filtrated and dried to obtain polymer compound C-2 (0.9 g) represented by the following formula:

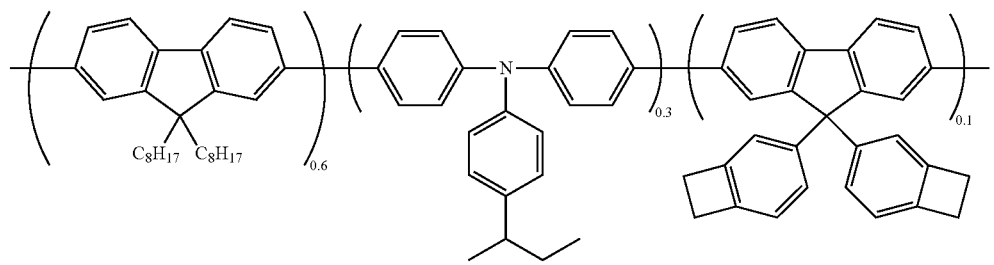

wherein the numbers attached outside parentheses each represent a molar ratio of a repeating unit.

The polystyrene-equivalent number average molecular weight of polymer compound C-2 was $8.4 \times 10^4$ and the polystyrene-equivalent weight average molecular weight thereof was $2.0 \times 10^5$.

Synthesis Example 2

Synthesis of Polymer Compound P-9

Under an inert gas atmosphere, compound MM-8 (7.28 g) represented by the following formula MM-8:

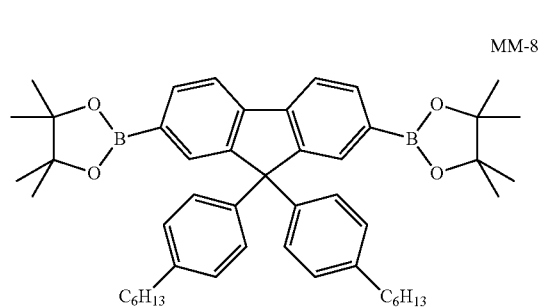

MM-8

2,7-dibromo-9,9-dioctylfluorene (4.94 g), compound MM-9 (0.74 g), represented by the following formula MM-9:

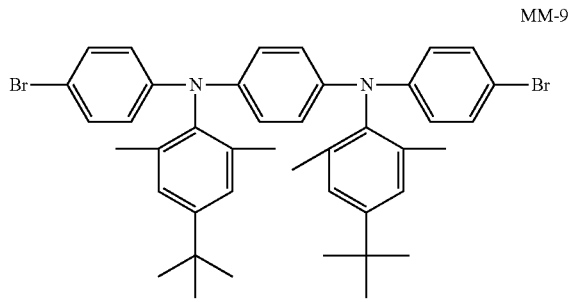 [SMILES: Cc1cc(C(C)(C)C)cc(C)c1N(c1ccc(Br)cc1)c1ccc(N(c2ccc(Br)cc2)c2c(C)cc(C(C)(C)C)cc2C)cc1]

MM-9 bis triphenylphosphine palladium dichloride (7.0 mg), trioctylmethylammonium chloride (trade name: Aliquat 336, manufactured by Aldrich) (1.30 g) and toluene (100 ml) were blended and heated to 105° C. To the resultant reaction solution, a 2 M aqueous sodium carbonate solution (27 ml) was added dropwise and refluxed for 2 hours. After completion of the reaction, phenylboric acid (120 mg) was added and refluxed for further 4 hours. Subsequently, a 1.8 M aqueous sodium diethyldithiacarbamate solution (60 ml) was added and stirred at 80° C. for 4 hours. The resultant reaction solution was cooled to room temperature, then washed three times with water (130 ml), three times with a 3 wt % aqueous acetic acid solution (130 ml) and three times with water (130 ml) and purified by passing it through an alumina column and a silica gel column. The resultant toluene solution was added dropwise to methanol (1.5 L) and stirred for one hour. Thereafter, the resultant solid substance was filtrated and dried to obtain polymer compound C-9 (8.0 g) represented by the following formula:

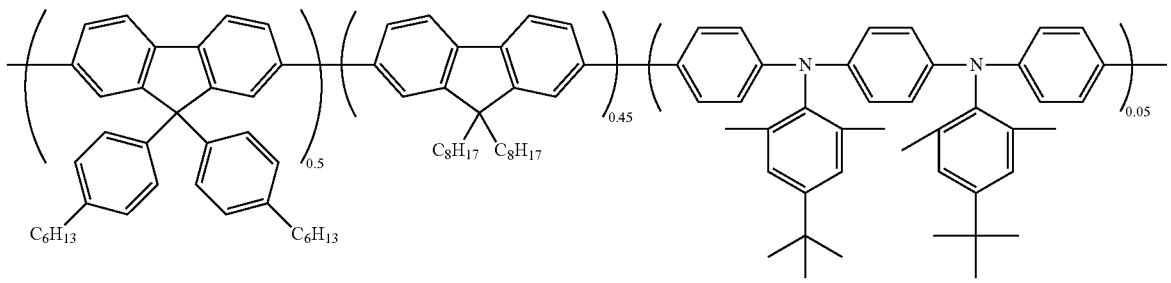

wherein the numbers attached outside parentheses each represent a molar ratio of a repeating unit.

The polystyrene-equivalent number average molecular weight of polymer compound C-9 was $5.1 \times 10^4$ and the polystyrene-equivalent weight average molecular weight thereof was $1.4 \times 10^5$.

Note that compound MM-8 represented by the above formula MM-8 was synthesized by a method described in WO2008111658.

Furthermore, compound MM-9 represented by the above formula MM-9 was synthesized by a method described in EP1394188.

<Measurement> (Preparation of a Liquid Composition, Evaluation of Residual Film Rate on Glass Substrate)

Polymer compounds P-1 to P-8 and C-1 to C-2 were each dissolved in xylene. In this manner, a xylene solution containing about 1 wt % of each of the polymer compounds was prepared.

The liquid composition thus prepared was added dropwise onto a glass substrate by a spin coater (trade name: MS-A100 type, manufactured by Misawa) in the condition of 1000 rpm for 15 seconds. The film thickness ($H_1$) of the resultant film was measured by a profiler (trade name: P-16+, manufactured by KLA-Tencor Corporation).

Subsequently, in a globe box purged with nitrogen, the film on the glass substrate was baked by use of a high power hot plate (trade name: HP-ISA, manufactured by AS ONE Corporation), at each baking temperature for 20 minutes. The resultant film on the glass substrate was cooled to room temperature, then soaked in a xylene solution and then rinsed by a spin coater (trade name: MS-A100 type, manufactured by Misawa) in the conditions of 1000 rpm for 15 seconds. The film thickness ($H_2$) of the film produced was measured by the profiler (trade name: P-16+, manufactured by KLA-Tencor Corporation).

A value of $(H_2)/(H_1) \times 100(\%)$ was defined as a residual film rate and the value is shown in Table 1.

TABLE 1

|  | Polymer compound | Residual film rate at baking temperature of 170° C. | Residual film rate at baking temperature of 190° C. |
|---|---|---|---|
| Example 11 | P-1 | 56% | 99% |
| Example 12 | P-2 | 99% | 99% |
| Example 13 | P-3 | 20% | 82% |
| Example 14 | P-4 | 70% | 95% |
| Example 15 | P-5 | 89% | 93% |
| Example 16 | P-6 | 66% | 96% |
| Example 17 | P-7 | 69% | 82% |
| Example 18 | P-8 | 63% | 82% |
| Comparative Example 3 | C-1 | 0% | 10% |
| Comparative Example 4 | C-2 | 0% | 53% |

<Evaluation>

Polymer compounds P-1 to P-8 show high residual film rate compared to polymer compounds C-1 and C-2 and thus were confirmed to have high harden ability.

Production and Evaluation of Electroluminescence (EL) Device

Example 19

Preparation of Polymer Compound <P-2> Solution

The polymer compound <P-2> obtained above was dissolved in xylene to prepare a xylene solution having a polymer concentration of 1.2 wt %.

Preparation of Polymer Compound <P-9> Solution

The polymer compound <P-9> obtained above was dissolved in xylene to prepare a xylene solution having a polymer concentration of 1.2 wt %.
Production of EL Device On a glass substrate to which an ITO film of 150 nm in thickness was attached by a sputtering method, a suspension solution of poly(3,4)ethylenedioxythiophene/polystyrene sulfonate (Baytron P AI4083 manufactured by Bayer) previously filtrated by a 0.2 µm membrane filter, was applied by spin coating to form a film of 70 nm in thickness and dried on a hot plate at 200° C. for 10 minutes. Subsequently, using a xylene solution of the polymer compound <P-2> obtained above, a film was formed by spin coating at a rotation rate of 1600 rpm and heated on a hot plate at 190° C. for 20 minutes to harden the film. After completion of film formation, the thickness of the film was about 20 nm. Furthermore, using a xylene solution of the polymer compound <P-9> obtained above, a film was formed by spin coating at a rotation rate of 1500 rpm. After the film formation, the thickness of the film was about 60 nm. Furthermore, this was dried under reduced pressure at 130° C. for 10 minutes, and thereafter barium was vapor-deposited as a cathode in a thickness of about 5 nm, and then aluminum was vapor-deposited in a thickness of about 100 nm to produce an EL device. Note that vapor deposition of a metal was initiated after a degree of vacuum reached $1 \times 10^{-4}$ Pa or less.
Performance of EL Device When voltage was applied to the resultant device, EL emission having a peak at 460 nm was provided from the device.

The time (life) for reducing a degree of brightness from the initial brightness (100 cd/m$^2$) to a half (50%) was as long as 120 hours.

Example 20

Preparation of Polymer Compound <P-5> Solution

The polymer compound <P-5> obtained above was dissolved in xylene to prepare a xylene solution having a polymer concentration of 1.2 wt %.
Production of EL Device On a glass substrate to which an ITO film of 150 nm in thickness was attached by a sputtering method, a suspension solution of poly(3,4)ethylenedioxythiophene/polystyrene sulfonate (Baytron P AI4083 manufactured by Bayer) previously filtrated by a 0.2 µm membrane filter, was applied by spin coating to form a film of 70 nm in thickness and dried on a hot plate at 200° C. for 10 minutes. Subsequently, using a xylene solution of the polymer compound <P-5> obtained above, a film was formed by spin coating at a rotation rate of 1600 rpm and heated on a hot plate at 190° C. for 20 minutes to harden the film. After the film formation, the thickness of the film was about 20 nm. Furthermore, using a xylene solution of the polymer compound <P-9> obtained above, a film was formed by spin coating at a rotation rate of 1500 rpm. After completion of film formation, the thickness of the film was about 60 nm. Furthermore, this was dried under reduced pressure at 130° C. for 10 minutes, and thereafter barium was vapor-deposited as a cathode in a thickness of about 5 nm, and then aluminum was vapor-deposited in a thickness of about 100 nm to produce an EL device. Note that vapor deposition of a metal was initiated after a degree of vacuum reached $1 \times 10^{-4}$ Pa or less.
Performance of EL Device When voltage was applied to the resultant device, EL emission having a peak at 475 nm was provided from the device.

The time (life) for reducing a degree of brightness from the initial brightness (100 cd/m$^2$) to a half (50%) was as long as 16 hours.

Comparative Example 21

Preparation of Polymer Compound <P-6> Solution

The polymer compound <P-6> obtained above was dissolved in xylene to prepare a xylene solution having a polymer concentration of 1.2 wt %.
Production of EL Device On a glass substrate to which an ITO film of 150 nm in thickness was attached by a sputtering method, a suspension solution of poly(3,4)ethylenedioxythiophene/polystyrene sulfonate (Baytron P AI4083 manufactured by Bayer) previously filtrated by a 0.2 µm membrane filter was applied by spin coating to form a film of 70 nm in thickness and dried on a hot plate at 200° C. for 10 minutes. Subsequently, using a xylene solution of the polymer compound <P-6> obtained above, a film was formed by spin coating at a rotation rate of 1600 rpm and heated on a hot plate at 190° C. for 20 minutes to harden the film. After completion of film formation, the thickness of the film was about 20 nm. Furthermore, using a xylene solution of the polymer compound <P-9> obtained above, a film was formed by spin coating at a rotation rate of 1500 rpm. After the film formation, the thickness of the film was about 60 nm. Furthermore, this was dried under reduced pressure at 130° C. for 10 minutes, and thereafter barium was vapor-deposited as a cathode in a thickness of about 5 nm, and then aluminum was vapor-deposited in a thickness of about 100 nm to produce an EL device. Note that vapor deposition of a metal was initiated after a degree of vacuum reached $1 \times 10^{-4}$ Pa or less.

Performance of EL Device

When voltage was applied to the resultant device, EL emission having a peak at 470 nm was provided from the device.

The time (life) for reducing a degree of brightness from the initial brightness (100 cd/m²) to a half (50%) was as long as 18 hours.

Comparative Example 5

Preparation of Polymer Compound <C-1> Solution

The polymer compound <C-1> obtained above was dissolved in xylene to prepare a xylene solution having a polymer concentration of 1.2 wt %.
Production of EL Device On a glass substrate to which an ITO film of 150 nm in thickness was attached by a sputtering method, a suspension solution of poly(3,4)ethylenedioxythiophene/polystyrene sulfonate (Baytron P AI4083 manufactured by Bayer) previously filtrated by a 0.2 μm membrane filter was applied by spin coating to form a film of 70 nm in thickness and dried on a hot plate at 200° C. for 10 minutes. Subsequently, using a xylene solution of the polymer compound <C-1> obtained above, a film was formed by spin coating at a rotation rate of 1600 rpm and heated on a hot plate at 190° C. for 20 minutes to harden the film. After completion of film formation, the thickness of the film was about 20 nm. Furthermore, using a xylene solution of the polymer compound <P-9> obtained above, a film was formed by spin coating at a rotation rate of 1500 rpm. After the film formation, the thickness of the film was about 60 nm. Furthermore, this was dried under reduced pressure at 130° C. for 10 minutes, and thereafter barium was vapor-deposited as a cathode in a thickness of about 5 nm, and then aluminum was vapor-deposited in a thickness of about 100 nm to produce an EL device. Note that vapor deposition of a metal was initiated after a degree of vacuum reached $1\times10^{-4}$ Pa or less.
Performance of EL Device When voltage was applied to the resultant device, EL emission having a peak at 460 nm was provided from the device.

The time (life) for reducing a degree of brightness from the initial brightness (100 cd/m²) to a half (50%) was 14 hours.

Comparative Example 6

Preparation of Polymer Compound <C-2> Solution

The polymer compound <C-2> obtained above was dissolved in xylene to prepare a xylene solution having a polymer concentration of 1.2 wt %.
Production of EL Device On a glass substrate to which an ITO film of 150 nm in thickness was attached by a sputtering method, a suspension solution of poly(3,4)ethylenedioxythiophene/polystyrene sulfonate (Baytron P AI4083 manufactured by Bayer) filtrated by a 0.2 μm membrane filter was applied by spin coating to form a film of 70 nm in thickness and dried on a hot plate at 200° C. for 10 minutes. Subsequently, using a xylene solution of the polymer compound <C-2> obtained above, a film was formed by spin coating at a rotation rate of 1600 rpm and heated on a hot plate at 190° C. for 20 minutes to harden the film. After completion of film formation, the thickness of the film was about 20 nm. Furthermore, using a xylene solution of the polymer compound <P-9> obtained above, a film was formed by spin coating at a rotation rate of 1500 rpm. After completion of film formation, the thickness of the film was about 60 nm. Furthermore, this was dried under reduced pressure at 130° C. for 10 minutes, and thereafter barium was vapor-deposited as a cathode in a thickness of about 5 nm, and then aluminum was vapor-deposited in a thickness of about 100 nm to produce an EL device. Note that vapor deposition of a metal was initiated after a degree of vacuum reached $1\times10^{-4}$ Pa or less.
Performance of EL Device When voltage was applied to the resultant device, EL emission having a peak at 460 nm was provided from the device.

The time (life) for reducing a degree of brightness from the initial brightness (100 cd/m²) to a half (50%) was 9 hours.

INDUSTRIAL APPLICABILITY

The polymer compound of the present invention can be used as a component of a light-emitting device, etc.

The invention claimed is:

1. A polymer compound comprising a repeating unit represented by the following formula (I):

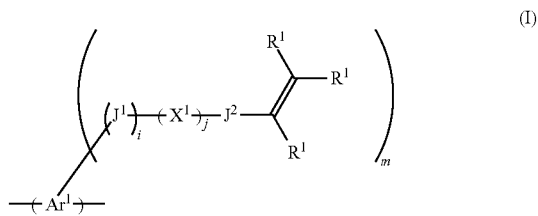

wherein $Ar^1$ represents an arylene group, a divalent heterocyclic group or a divalent aromatic amine; $J^1$ each independently represents a direct bond, an alkylene group or a phenylene group; $J^2$ is an alkylene group; $X^1$ represents an oxygen atom or a sulfur atom; i is an integer of 0 to 3, j is 0 or 1, and m is 1 or 2; $R^1$ represents a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an acid imide group, a monovalent heterocyclic group, a carboxyl group, a substituted carboxyl group, a cyano group or a nitro group; a plurality of $R^1$ may be the same or different; and a plurality of $J^1$, $J^2$, $X^1$, i and j each may be the same or different, and a repeating unit represented by the following formula (II):

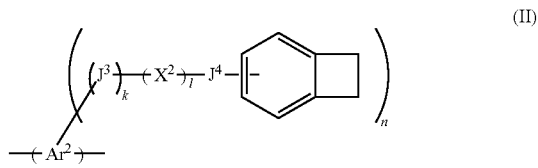

wherein $Ar^2$ represents a fluorene-diyl group; $J^3$ and $J^4$ each independently represent a direct bond, an alkylene group or a phenylene group; $X^2$ represents an oxygen atom or a sulfur atom; k is an integer of 0 to 3, l is 0 or 1, and n is 1 or 2; a plurality of $J^3$, $J^4$, $X^2$, k and l each may be the same or different.

2. The polymer compound according to claim 1, wherein in the above formula (I), $Ar^1$ is a fluorene-diyl group.

3. The polymer compound according to claim 1, wherein in the above formula (I), i and j are 0.

4. The polymer compound according to claim 1, wherein the repeating unit represented by the above formula (I) is a repeating unit represented by the following formula (III):

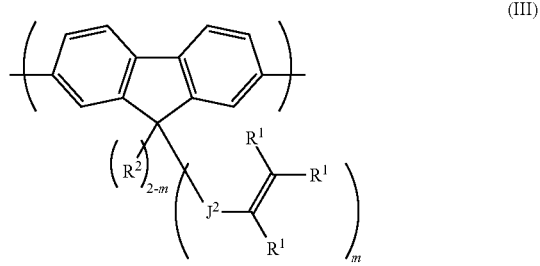

(III)

wherein $J^2$, $R^1$ and m are the same as defined above; and $R^2$ represents an alkyl group, an aryl group, an arylalkyl group or an arylalkoxy group.

5. The polymer compound according to claim 1, wherein m is 2.

6. The polymer compound according to claim 1, wherein in the above formula (II), k and l are 0.

7. The polymer compound according to claim 1, wherein the repeating unit represented by the above formula (II) is a repeating unit represented by the following formula (IV):

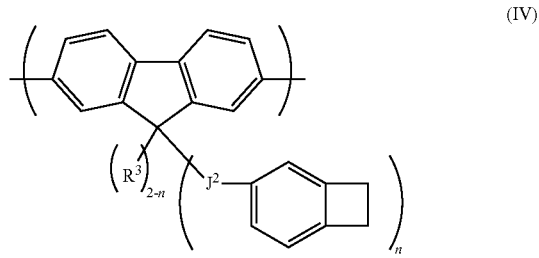

(IV)

wherein $J^4$ and n are the same as defined above; and $R^3$ represents an alkyl group, an aryl group, an arylalkyl group or an arylalkoxy group.

8. The polymer compound according to claim 1, wherein n is 2.

9. The polymer compound according to claim 1, wherein $J^4$ is a direct bond or an alkylene group.

10. The polymer compound according to claim 1, having a polystyrene-equivalent number average molecular weight of $1\times10^3$ to $1\times10^8$.

11. A composition comprising the polymer compound according to claim 1.

12. A liquid composition comprising the polymer compound according claim 1 and a solvent.

13. A film comprising the polymer compound according to claim 1.

14. A film obtained by crosslinking the polymer compound according to claim 1.

15. A light-emitting device having electrodes comprising an anode and a cathode, a light-emitting layer provided between the electrodes and comprising the polymer compound according to claim 1.

16. A light-emitting device having electrodes comprising an anode and a cathode, a light-emitting layer provided between the electrodes and formed by crosslinking the polymer compound according to claim 1.

17. A surface light source comprising the light-emitting device according to claim 15.

18. A display comprising the light-emitting device according to claim 15.

19. An organic transistor formed of the polymer compound according to claim 1.

20. An organic photoelectric transducer formed of the polymer compound according to claim 1.

* * * * *